US007465793B2

(12) United States Patent
Xue et al.

(10) Patent No.: US 7,465,793 B2
(45) Date of Patent: Dec. 16, 2008

(54) SYNTHETIC Δ17 DESATURASE DERIVED FROM *PHYTOPHTHORA RAMOURUM* AND ITS USE IN MAKING POLYUNSATURATED FATTY ACIDS

(75) Inventors: Zhixiong Xue, Chadds Ford, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/787,772

(22) Filed: Apr. 18, 2007

(65) Prior Publication Data

US 2007/0249026 A1 Oct. 25, 2007

Related U.S. Application Data

(60) Provisional application No. 60/793,575, filed on Apr. 20, 2006.

(51) Int. Cl.
*C07H 21/04* (2006.01)
*C12Q 1/68* (2006.01)
*C12P 21/06* (2006.01)
*C12P 7/64* (2006.01)
*C12N 15/70* (2006.01)
*C12N 1/15* (2006.01)

(52) U.S. Cl. ...................... 536/23.2; 435/183; 435/193; 435/6; 435/69.1; 435/320.1; 435/252.3; 435/134

(58) Field of Classification Search ................. 435/183, 435/193, 6, 69.1, 320.1, 252.3, 134; 536/23.2
See application file for complete search history.

(56) References Cited

U.S. PATENT DOCUMENTS

| | | | |
|---|---|---|---|
| 7,125,672 | B2 | 10/2006 | Picataggio et al. |
| 7,189,559 | B2 | 3/2007 | Damude et al. |
| 7,192,762 | B2 | 3/2007 | Macool et al. |
| 2003/0190733 | A1 | 10/2003 | Mukerji et al. |
| 2006/0115881 | A1 | 6/2006 | Damude et al. |
| 2007/0224661 | A1 | 9/2007 | Cirpus et al. |

FOREIGN PATENT DOCUMENTS

| | | | |
|---|---|---|---|
| DE | 102005013779 | A1 | 9/2006 |
| WO | 2004101757 | A2 | 11/2004 |
| WO | WO 2004/101753 | * | 11/2004 |
| WO | WO 2005/012316 | A | 2/2005 |
| WO | WO 2005/083053 | A2 | 9/2005 |
| WO | WO 2005/083093 | A | 9/2005 |
| WO | WO 2006/052870 | A | 5/2006 |
| WO | WO 2006/100241 | A2 | 9/2006 |

OTHER PUBLICATIONS

Seq ID No. 6 sequence alignment data.*

Pereira, Suzette L. et al., A novel Omega3-fatty acid desaturase involved in the biosynthesis of eicosaptentaenoic acid, Biochemistry Journal, 2004, pp. 665-671, vol. 378, Biochemical Society.

Sayanova, Olga V. et al., Eicosapentaenoic acid: biosynthetic routes and the potential for synthesis in transgenic plants, Phytochemistry, 2004, pp. 147-158, vol. 65, Elsevier Ltd.

International Search Report dated Feb. 27, 2008, International Application No. PCT/US2007/009572, International Filing Date: Apr. 19, 2007.

J. Dyerberg et. al., Fatty Acid Composition of the Plasma Lipids in Greenland Eskimos, Amer. J. Clin. Nutr., 1975, vol. 28:958-966.

J. Dyerberg et. al., Eicosapentaenoic Acid and Prevention of Thrombosis and Atherosclerosis?, Lancet., 1978, vol. 2:117-119.

H. Shimokawa, Beneficial Effects of Eicosapetaenoic Acid on Endothelial Vasodilator Functions in Animals and Humans, World Rev. Nurt. Diet, 2001, vol. 88:100-108.

C. Schacky et. al., 3 Fatty Acids From Eskimos to Clinical Cardiology—What Took Us So Long?, World Rev. Nutr. Diet, 2001, vol. 88:90-99.

U.S. Appl. No. 60/855,177, filed Oct. 30, 2006, Zhixiong Xue et al.

U.S. Appl. No. 10/840,579, filed May 6, 2004, Stephen K. Picataggio et al.

U.S. Appl. No. 10/840,325, filed May 6, 2004, Narendra S. Yadav et al.

U.S. Appl. No. 10/869,630, filed Jun. 16, 2004, Stephen K. Picataggio et al.

U.S. Appl. No. 10/882,760, filed Jul. 1, 2004, Narendra S. Yadav et al.

U.S. Appl. No. 10/985,254, filed Nov. 10, 2004, Narendra S. Yadav et al.

U.S. Appl. No. 10/985,691, filed Nov. 10, 2004, Narendra S. Yadav et al.

U.S. Appl. No. 10/987,548, filed Nov. 12, 2004, Dana M. Walters Pollak et al.

U.S. Appl. No. 11/024,545, filed Dec. 29, 2004, Zhixiong Xue et al.

U.S. Appl. No. 11/024,544, filed Dec. 29, 2004, Narendra S. Yadav et al.

U.S. Appl. No. 11/166,993, filed Jun. 24, 2005, Howard Glenn Damude et al.

U.S. Appl. No. 11/183,664, filed Jul. 18, 2005, Stephen K. Picataggio et al.

U.S. Appl. No. 11/185,301, filed Jul. 20, 2005, Zhixiong Xue et al.

U.S. Appl. No. 11/190,750, filed Jul. 27, 2005, Stephen K. Picataggio et al.

U.S. Appl. No. 11/198,975, filed Aug. 8, 2005, Quinn Qun Zhu et al.

U.S. Appl. No. 11/225,354, filed Sep. 13, 2005, Zhixiong Xue et al.

Juretzek, Thomas et al., Vectors for gene expression and amplification in the yeast Yarrowia lipolytica, Yeast, 2001, p. 97-113, vol. 18, John Wiley & Sons, Ltd.

(Continued)

*Primary Examiner*—Tekchand Saidha
*Assistant Examiner*—Iqbal H Chowdhury
(74) *Attorney, Agent, or Firm*—S. Neil Feltham

(57) ABSTRACT

The present invention relates to Δ17 desaturases, which have the ability to convert ω-6 fatty acids into their ω-3 counterparts (i.e., conversion of arachidonic acid [20:4, ARA] to eicosapentaenoic acid [20:5, EPA]). Isolated nucleic acid fragments and recombinant constructs comprising such fragments encoding Δ17 desaturases along with a method of making long chain polyunsaturated fatty acids (PUFAs) using these Δ17 desaturases in plants and oleaginous yeast is disclosed.

3 Claims, 9 Drawing Sheets

OTHER PUBLICATIONS

Figure 1:
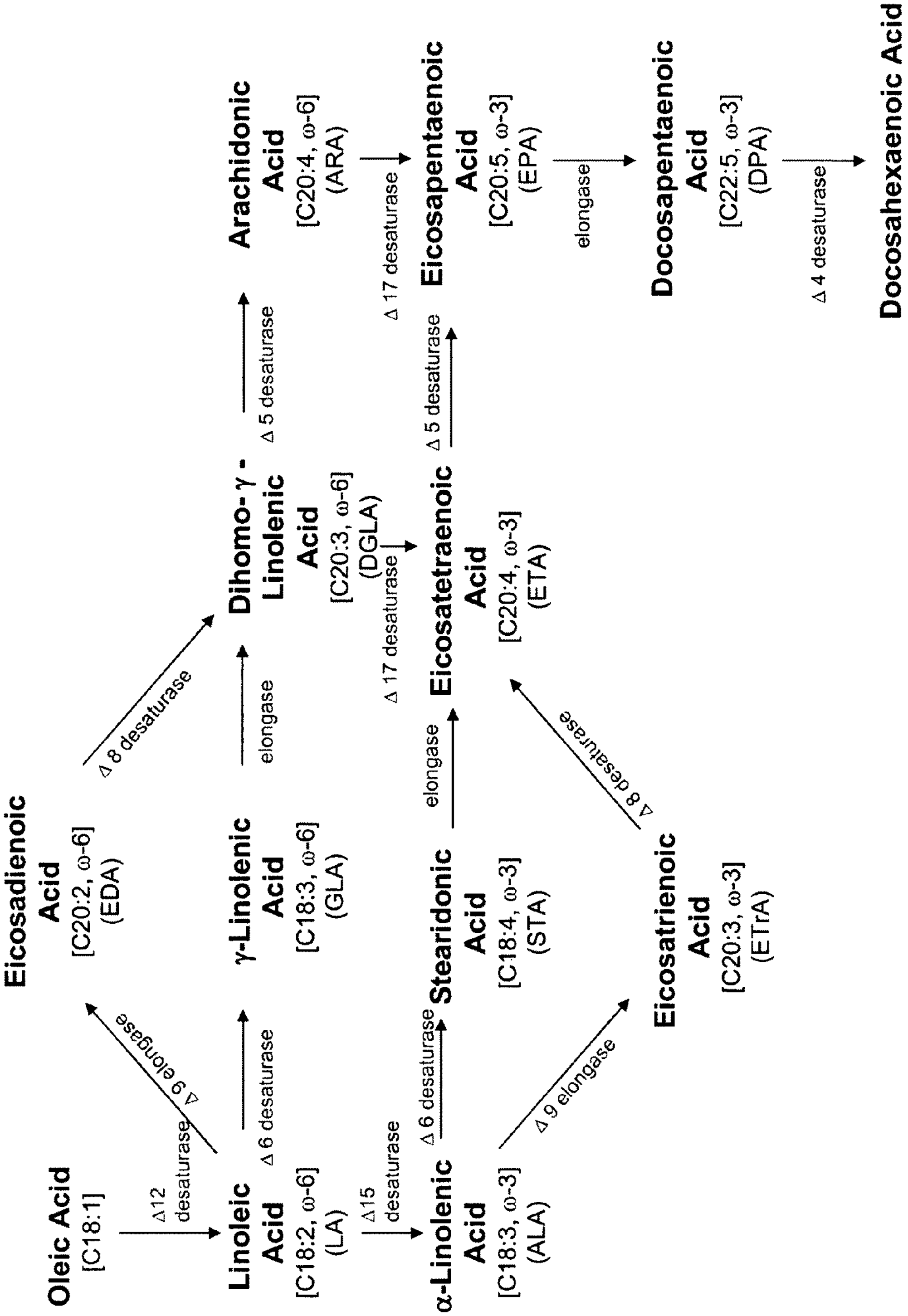

Partial International Search Report, International Application No. PCT/US2007/009572, International Filing Date Apr. 19, 2007.

U.S. Appl. No. 11/253,882, filed Oct. 19, 2005, Daniel Joseph Macool et al.

U.S. Appl. No. 11/264,784, filed Nov. 1, 2005, Howard Glenn Damude et al.

U.S. Appl. No. 11/264,737, filed Nov. 1, 2005, Howard Glenn Damude et al.

U.S. Appl. No. 11/265,761, filed Nov. 2, 2005, Howard Glenn Damude et al.

U.S. Appl. No. 60/795,810, filed Apr. 28, 2006, Howard Glenn Damude et al.

U.S. Appl. No. 60/793,575, filed Apr. 20, 2006, Zhixiong Xue et al.

U.S. Appl. No. 60/796,637, filed May 1, 2006, Narendra S. Yadav et al.

U.S. Appl. No. 60/801,172, filed May 17, 2006, Howard Glenn Damude et al.

U.S. Appl. No. 60/801,119, filed May 17, 2006, Howard Glenn Damude et al.

U.S. Appl. No. 60/853,563, filed Oct. 23, 2006, Howard Glenn Damude et al.

U.S. Appl. No. 60/855,177, filed Oct. 30, 2006, Zhixiong Xue et al.

U.S. Appl. No. 11/601,563, filed Nov. 16, 2006, Howard Glenn Damude et al.

U.S. Appl. No. 11/601,564, filed Nov. 16, 2006, Howard Glenn Damude et al.

U.S. Appl. No. 11/635,258, filed Dec. 7, 2006, Howard Glenn Damude et al.

U.S. Appl. No. 11/613,420, filed Dec. 20, 2006, John E Seip et al.

* cited by examiner

A
PsD17S
pPsD17S
3806 bp
Ori
Amp
B
Ura3-616
Fba1 + Intron
EL1S
Pex20-3'
Ura5-784
pKUNF1-KEA
6619 bp
Amp
C
XPR2
GUS
intron
FBA1 + intron
LEU2
pDMW214
9513 bp
ColE1
amp
f1 ori
ARS 18
D
D17syn-P. sojae
XPR2
LEU2
pFmPs17S
8727 bp
ColE1
Amp
f1 ori
ARS 18

Figure 4
A
pKUNF12T6E
pDMW271
ATCC
#20362
~20% LA
M4
8% DGLA
Y2047
11% ARA
B
pKUNF12T6E
12649 bp
C
pDMW271
13034 bp

Figure 6
A
FOA
pZKLeuN-29E3
pY116
pKO2UF8289
pY116
pZKSL-555R
ATCC #20362
~20%LA
Y2224
Ura-,
Chr. E
Y4001
17% EDA,
Leu-, Chr. C
Y4001U1
17% EDA,
Leu-, Ura-
Y4036
18% DGLA,
Leu-, Chr.B?
Y4036U
Leu-, Ura-
Y4070
12% ARA,
Ura-
B
pZKLeuN-29E3
14655 bp
Lip2
EgD9ES
FBAINm
Exp pro
EgD9E
Lip1-3'
GPD
F.D12
Pex20-3'
Leu-3'
LOXP
Ura3
Loxp
YAT
ME3S
Pex16-3'
Leu-5'
Amp
C
pY116
8739 bp
XPR2
Cre
ColE1
GPAT
Amp
f1 ori
Leu
ARS 18

A
pPrD17S
PrD17S
Ori
Amp
B
pZUFPrD17S
PrD17S
Pex20-3'
ColE1
Amp
f1 ori
ARS 18
Ura3
FBAIN
C
pZUF17
ColE1
Amp
f1 ori
ARS 18
Ura3
FBAIN
D17st
Pex20-3'

SYNTHETIC Δ17 DESATURASE DERIVED FROM *PHYTOPHTHORA RAMOURUM* AND ITS USE IN MAKING POLYUNSATURATED FATTY ACIDS

This application claims the benefit of U.S. Provisional Patent Application 60/793,575, filed Apr. 20, 2006.

FIELD OF THE INVENTION

This invention is in the field of biotechnology. More specifically, this invention pertains to the identification of nucleic acid fragments encoding Δ17 fatty acid desaturase enzymes and the use of these desaturases in making long chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., *Amer. J. Clin. Nutr.,* 28:958-966 (1975); Dyerberg, J. et al., *Lancet,* 2(8081):117-119 (Jul. 15, 1978); Shimokawa, H., *World Rev. Nutr. Diet,* 88:100-108 (2001); von Schacky, C. and Dyerberg, J., *World Rev. Nutr. Diet,* 88:90-99 (2001)). And, numerous other studies document wide-ranging health benefits conferred by administration of ω-3 and/or ω-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high level production of arachidonic acid (ARA; 20:4 ω-6), eicosapentaenoic acid (EPA; 20:5 ω-3) and docosahexaenoic acid (DHA; 22:6 ω-3). Whether ω-3/ω-6 PUFA production is the result of natural abilities or recombinant technology, both strategies may require conversion of ω-6 PUFAs into their ω-3 counterparts. Specifically, a Δ15 desaturase is responsible for the conversion of LA to ALA, while a Δ17 desaturase is responsible for the conversion of ARA to EPA (although some Δ17 desaturases can also use dihomo-γ-linolenic acid (DGLA; 20:3 ω-6) as a substrate to produce eicosatetraenoic acid (ETA; 20:4 ω-3)). Both of these enzymes have a role in the Δ6 desaturase/Δ6 elongase pathway (which is predominantly found in algae, mosses, fungi, nematodes and humans and which is characterized by the production of γ-linoleic acid (GLA; 18:3 ω-6) and/or stearidonic acid (STA; 18:4 ω-3)) and the Δ9 elongase/Δ8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) (FIG. 1).

Based on the role Δ17 desaturase enzymes play to thereby effectively enable the synthesis of ω-3 fatty acids, there has been considerable effort to identify and characterize these enzymes from various sources. However, only a few Δ17 desaturases are presently known. Specifically, U.S. Patent Publication No. 2003/0190733 describes the usoaltion and characterization of a Δ17 desaturase from *Saprolegnia diclina* (see also GenBank Accession No. AY373823). PCT Publication No. WO 2005/083053 provides sequences for a *Phytophthora infestans* "ω3 desaturase" (see also GenBank Accession No. CAJ30870), while PCT Publication No. WO 2006/100241 provides sequences for a *Phytophthora sojae* "ω3 desaturase", both of which appear to encode Δ17 desaturases. Also, commonly owned, co-pending application having Provisional Application No. 60/855,177 (discloses amino acid and nucleic acid sequences for a Δ17 desaturase enzyme from *Pythium aphamidermatum*. Thus, there is need for the identification and isolation of additional genes encoding Δ17 desaturases that will be suitable for heterologous expression in a variety of host organisms for use in the production of ω-3 fatty acids.

Applicants have solved the stated problem by isolating the genes encoding Δ17 desaturase from the oomycetes, *Phytophthora ramorum* and *Phytophthora sojae.*

SUMMARY OF THE INVENTION

The present invention relates to new genetic constructs encoding polypeptides having Δ17 desaturase activity, and their use in plants and yeast for the production of PUFAs and particularly ω-3 fatty acids.

Accordingly the invention provides an isolated nucleic acid molecule selected from the group consisting of:

a.) an isolated nucleotide sequence encoding a Δ17 desaturase enzyme, selected from the group consisting of SEQ ID NO:3 and SEQ ID NO:7; or, b.) an isolated nucleotide sequence that is completely complementary to (a).

In another embodiment the invention provides genetic constructs of the invention that are codon optimized for expression in *Yarrowia sp.* Additionally the invention provides host cells transformed with the genetic constructs of the invention for expression and production of ω-3 fatty acids.

In another embodiment the invention provides a method for the production of eicosapentaenoic acid comprising:

a) providing a host cell comprising:
   - i) an isolated nucleotide molecule encoding a Δ17 desaturase polypeptide, selected from the group consisting of:
     - 1) an isolated nucleotide molecule encoding a Δ17 desaturase polypeptide having at least 90.9% identity when compared to a polypeptide having the amino acid sequence as set forth in SEQ ID NO:2, based on the Clustal method of alignment;
     - 2) an isolated nucleotide molecule encoding a Δ17 desaturase polypeptide having at least 91.4% identity when compared to a polypeptide having the amino acid sequence as set forth in SEQ ID NO:4, based on the Clustal method of alignment; and,
     - 3) an isolated nucleotide molecule encoding a Δ17 desaturase polypeptide having at least 89.5% identity when compared to a polypeptide having an amino acid sequence as set forth in SEQ ID NO:6, based on the Clustal method of alignment; and
   - ii) a source of arachidonic acid;

b) growing the host cell of step (a) under conditions wherein the nucleic acid molecule encoding the Δ17 desaturase polypeptide is expressed and the arachidonic acid is converted to eicosapentaenoic acid; and c) optionally recovering the eicosapentaenoic acid of step (b).

In an alternate embodiment the invention provides a method for the production of eicosatetraenoic acid comprising a) providing a host cell comprising:
   i) an isolated nucleotide molecule encoding a Δ17 desaturase polypeptide, selected from the group consisting of:
      1) an isolated nucleotide molecule encoding a Δ17 desaturase polypeptide having at least 90.9% identity when compared to a polypeptide having the amino acid sequence as set forth in SEQ ID NO:2, based on the Clustal method of alignment;
      2) an isolated nucleotide molecule encoding a Δ17 desaturase polypeptide having at least 91.4% identity when compared to a polypeptide having the amino acid sequence as set forth in SEQ ID NO:4, based on the Clustal method of alignment; and,
      3) an isolated nucleotide molecule encoding a Δ17 desaturase polypeptide having at least 89.5% identity when compared to a polypeptide having an amino acid sequence as set forth in SEQ ID NO:6, based on the Clustal method of alignment; and
   ii) a source of dihomo-γ-linolenic acid;
b) growing the host cell of step (a) under conditions wherein the nucleic acid molecule encoding the Δ17 desaturase polypeptide is expressed and the dihomo-γ-linolenic acid is converted to eicosatetraenoic acid; and
c) optionally recovering the eicosatetraenoic acid of step (b).

In another embodiment the invention provides a method for the production of α-linolenic acid comprising:

a) providing a host cell comprising:
   i) an isolated nucleotide molecule encoding a bifunctional Δ17 desaturase polypeptide, selected from the group consisting of:
      1) an isolated nucleotide molecule encoding a Δ17 desaturase polypeptide having at least 90.9% identity when compared to a polypeptide having the amino acid sequence as set forth in SEQ ID NO:2, based on the Clustal method of alignment; and,
      2) an isolated nucleotide molecule encoding a Δ17 desaturase polypeptide having at least 91.4% identity when compared to a polypeptide having the amino acid sequence as set forth in SEQ ID NO:4, based on the Clustal method of alignment; and
   ii) a source of linoleic acid;
b) growing the host cell of step (a) under conditions wherein the nucleic acid molecule encoding the bifunctional Δ17 desaturase polypeptide is expressed and the linoleic acid is converted to α-linolenic acid; and,
c) optionally recovering the α-linolenic acid of step (b).

BIOLOGICAL DEPOSITS

The following biological material has been deposited with the American Type Culture Collection (ATCC), 10801 University Boulevard, Manassas, Va. 20110-2209, and bears the following designation, accession number and date of deposit.

| Biological Material | Accession No. | Date of Deposit |
|---|---|---|
| *Yarrowia lipolytica* Y2047 | ATCC PTA-7186 | Oct. 26, 2005 |

The biological materials listed above were deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE LISTINGS

FIG. 1 illustrates the ω-3/ω-6 fatty acid biosynthetic pathway.

Figure 2:
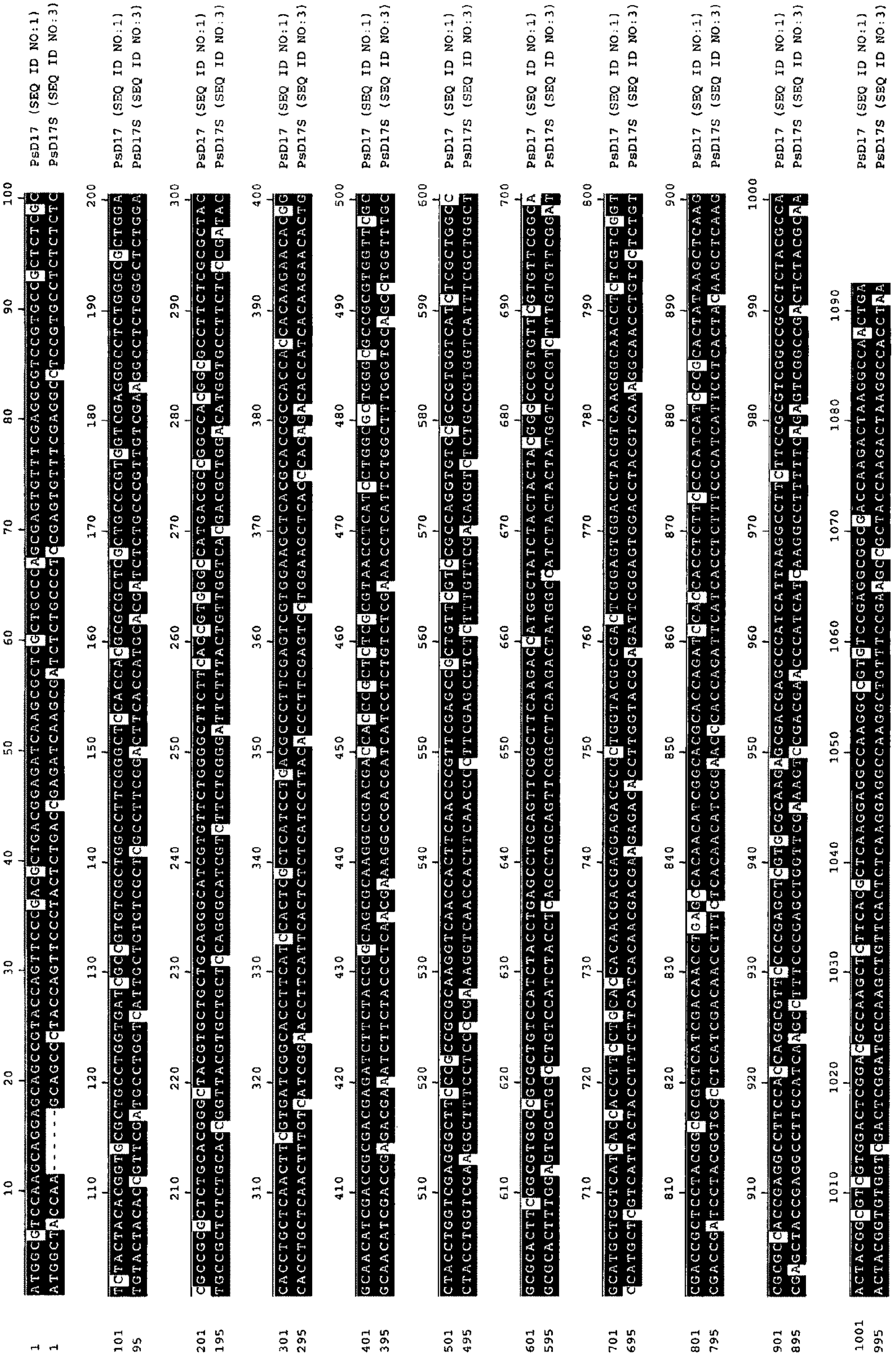

FIG. 2 shows a comparison of the DNA sequence of the *Phytophthora sojae* Δ17 desaturase gene (designated as "PsD17"; SEQ ID NO:1) and the synthetic gene (designated as "PsD17S"; SEQ ID NO:3) codon-optimized for expression in *Y. lipolytica.*

Figure 3:
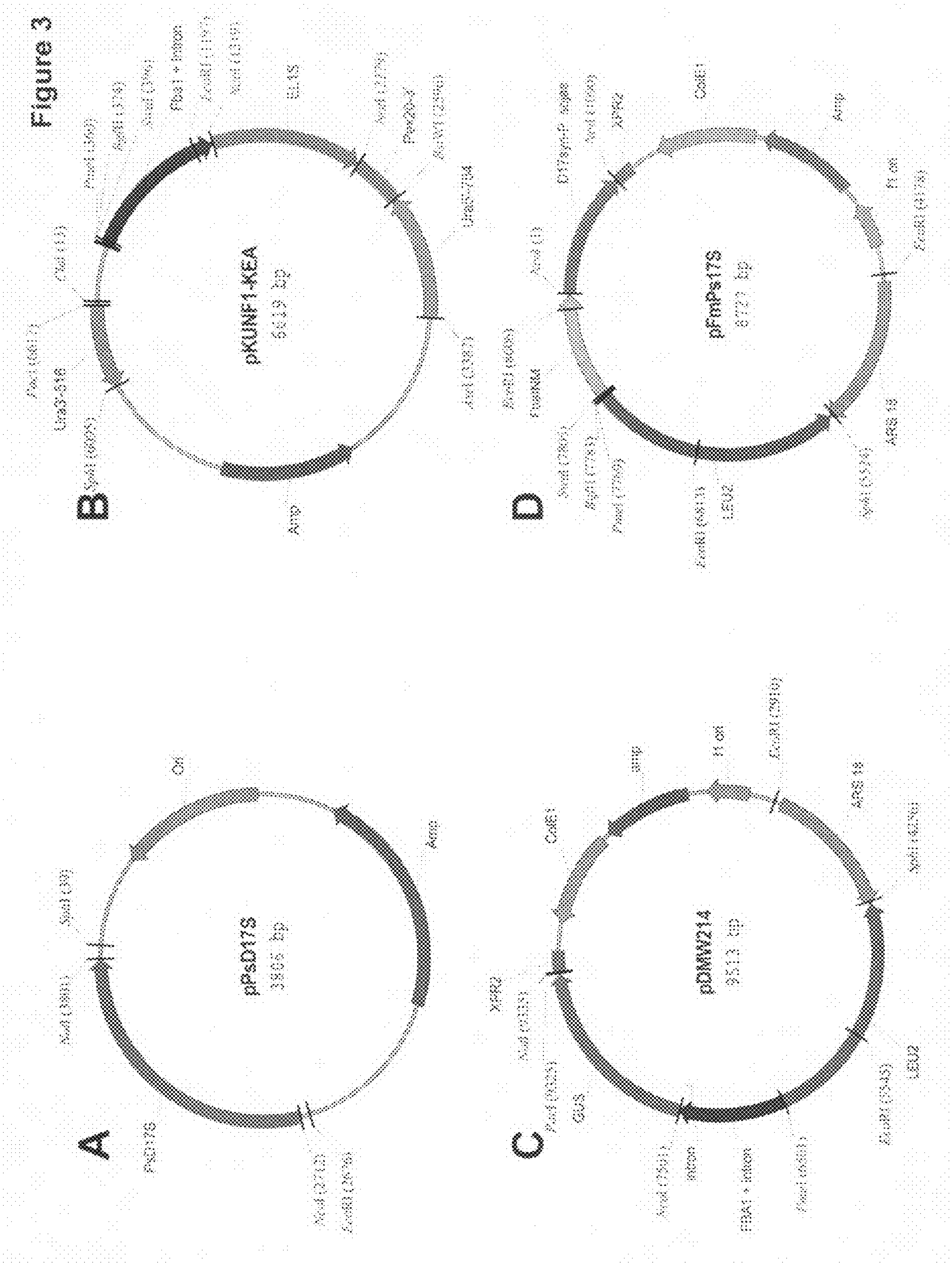

FIG. 3 provides plasmid maps for the following: (A) pPsD17S; (B) pKUNF1-KEA; (C) pDMW214; and (D) pFmPs17S.

Figure 4:

FIG. 4A diagrams the development of *Yarrowia lipolytica* strain Y2047, producing 11% ARA in the total lipid fraction. FIG. 4B provides a plasmid map for pKUNF12T6E, while FIG. 4C provides a plasmid map for pDMW271.

Figure 5:
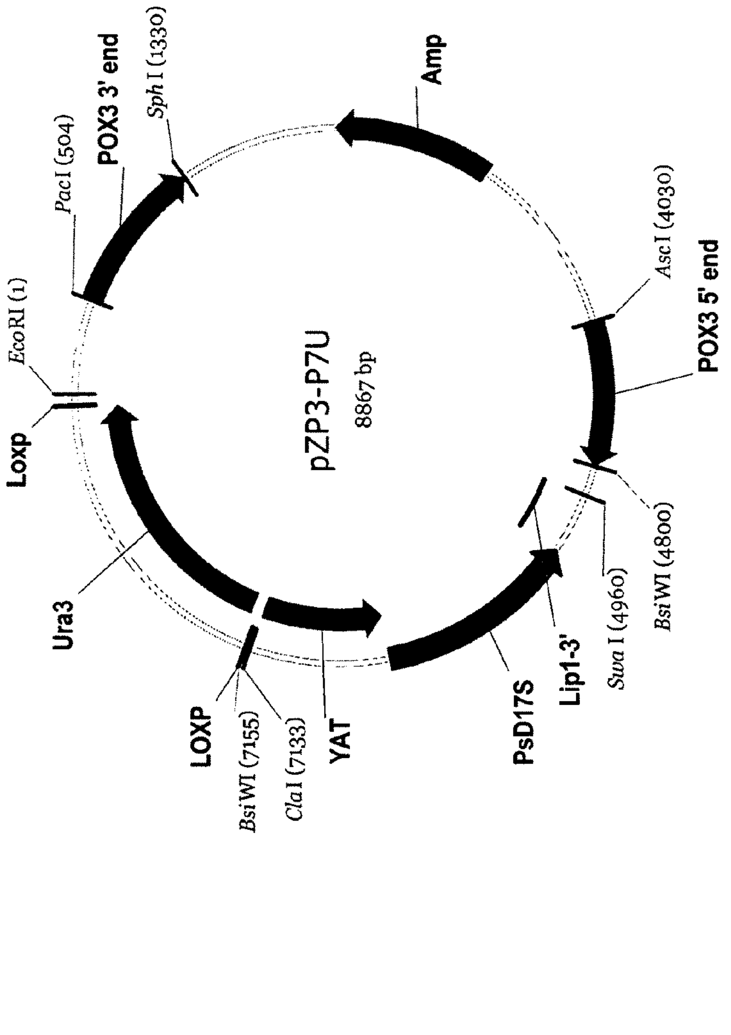

FIG. 5 provides a plasmid map for pZP3-P7U.

Figure 6:

FIG. 6A diagrams the development of *Yarrowia lipolytica* strain Y4070, producing 12% ARA in the total lipid fraction. FIG. 6B provides a plasmid map for pZKLeuN-29E3, while FIG. 6C provides a plasmid map for pY116.

Figure 7:
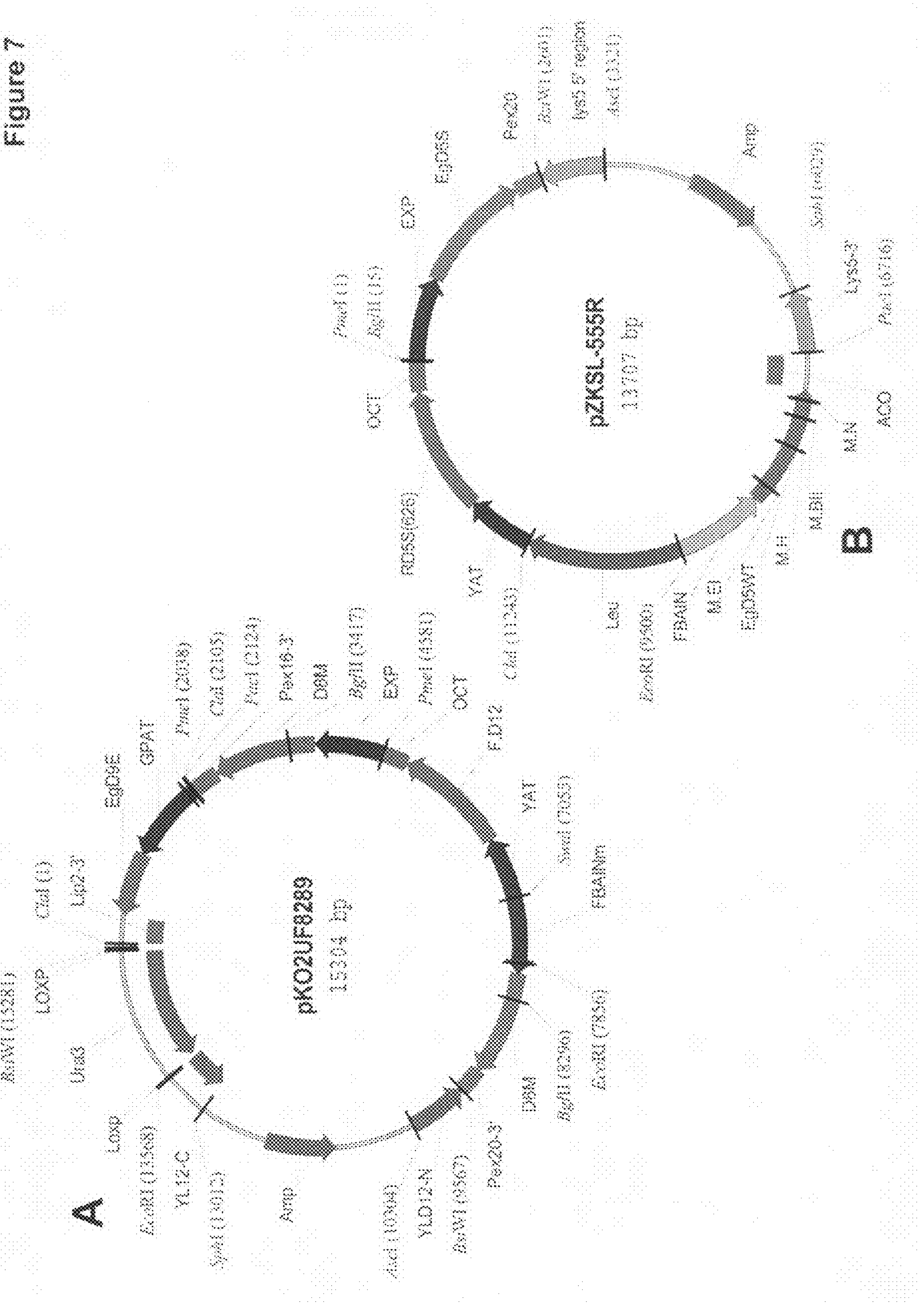

FIG. 7 provides plasmid maps for the following: (A) pKO2UF8289; and, (B) pZKSL-555R.

Figure 8:
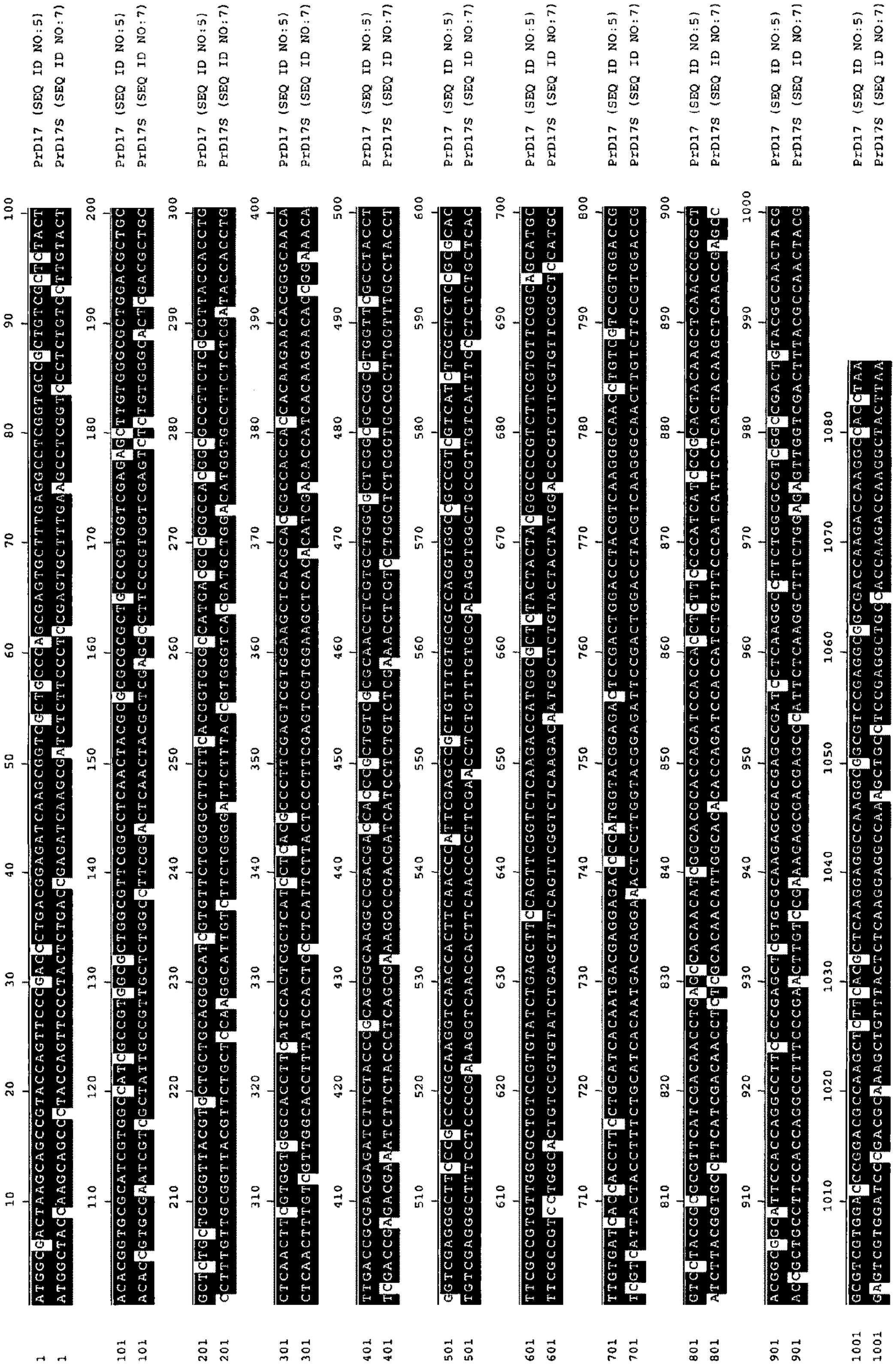

FIG. 8 shows a comparison of the DNA sequence of the *Phytophthora ramorum* Δ17 desaturase gene (designated as "PrD17"; SEQ ID NO:5) and the synthetic gene (designated as "PrD17S"; SEQ ID NO:7) codon-optimized for expression in *Y. lipolytica.*

Figure 9:
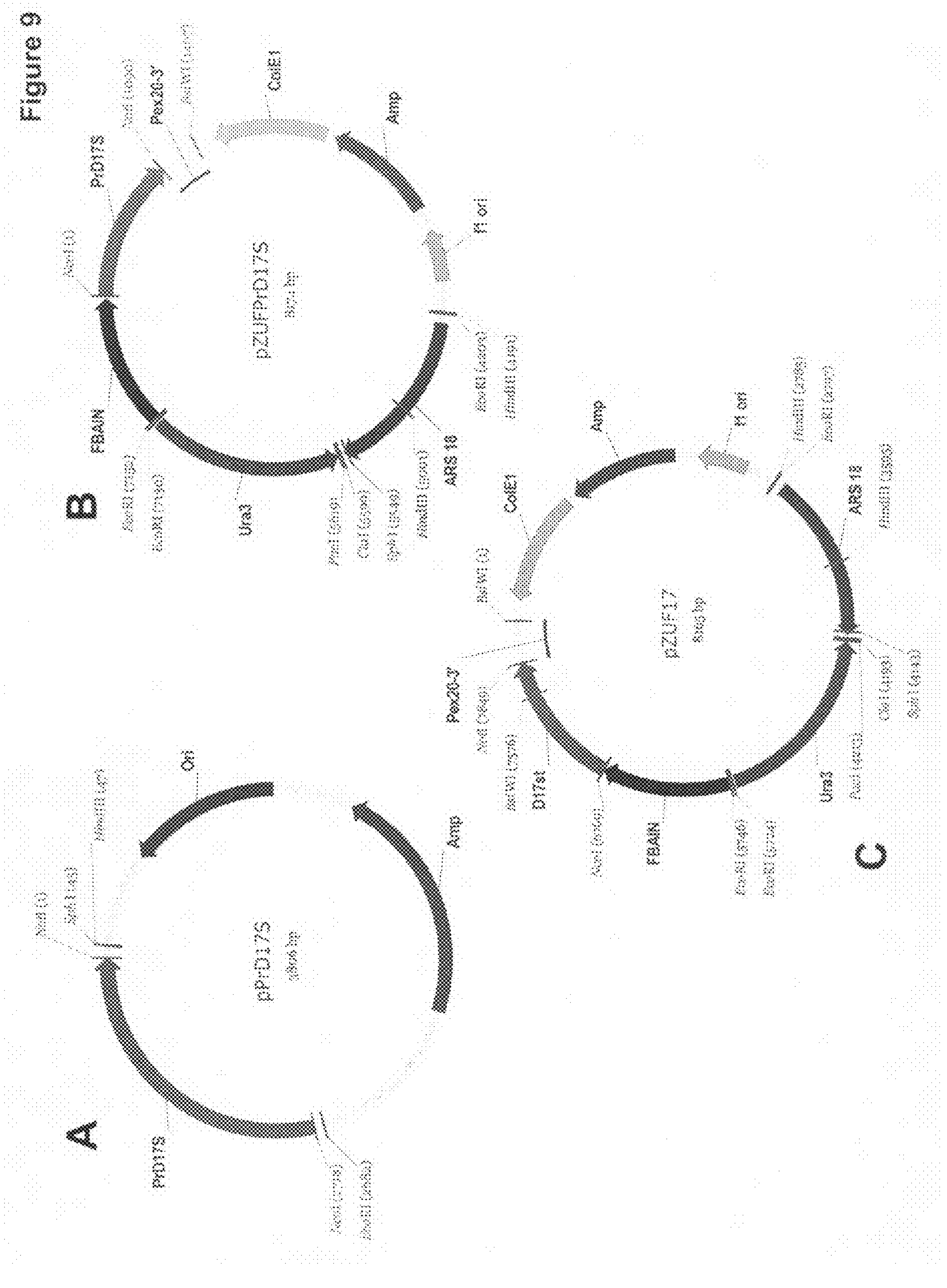

FIG. 9 provides plasmid maps for the following: (A) pPrD17S; (B) pZUFPrD17S; and, (C) pZUF17.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 C.F.R. §1.52(e). The Compact Disks are submitted in triplicate and are identical to one another. The disks are labeled "Copy 1—Sequence Listing"; "Copy 2—Sequence Listing"; and "CRF—Sequence Listing". The disks contain the following file: CL3479 conversion listing_25 having the following size: 230,000 bytes and which was created Apr. 17, 2007.

SEQ ID NOs:1-40 are ORFs encoding genes, proteins or plasmids, as identified in Table 1.

TABLE 1

Summary Of Gene And Protein SEQ ID Numbers

| Description and Abbreviation | Nucleic acid SEQ ID NO. | Protein SEQ ID NO. |
|---|---|---|
| *Phytophthora sojae* Δ17 desaturase ("PsD17") | 1 (1092 bp) | 2 (363 AA) |
| Synthetic Δ17 desaturase derived from *Phytophthora sojae*, codon-optimized for expression in *Yarrowia lipolytica* ("PsD17S") | 3 (1086 bp) | 4 (361 AA) |
| *Phytophthora ramorum* Δ17 desaturase ("PrD17") | 5 (1086 bp) | 6 (361 AA) |
| Synthetic Δ17 desaturase derived from *Phytophthora ramorum*, codon-optimized for expression in *Yarrowia lipolytica* ("PrD17S") | 7 (1086 bp) | 6 (361 AA) |
| *Phytophthora infestans* Δ17 desaturase ("PiD17") | 8 (1086) bp) | 9 (361 AA) |
| Plasmid pPsD17S | 10 (3806 bp) | — |
| Plasmid pKunF1-KEA | 11 (6619 bp) | — |
| Plasmid pDMW214 | 12 (9513 bp) | — |
| Plasmid pFmPsD17S | 13 (8727 bp) | — |
| Plasmid pKUNF12T6E | 14 (12,649 bp) | — |
| Synthetic $C_{18/20}$ elongase derived from *Thraustochytrium aureum* (U.S. Pat. No. 6,677,145), codon-optimized for expression in *Yarrowia lipolytica* ("EL2S") | 15 (819 bp) | 16 (272 AA) |
| Plasmid pDMW271 | 17 (13,034 bp) | — |
| Synthetic Δ5 desaturase derived from *Homo sapiens* (GenBank Accession No. NP_037534), codon-optimized for expression in *Yarrowia lipolytica* | 18 (1335 bp) | 19 (444 AA) |
| Plasmid pZP3-P7U | 20 (8867 bp) | — |
| *Escherichia coli* LoxP recombination site, recognized by a Cre recombinase enzyme | 21 (34 bp) | — |
| Plasmid pZKLeuN-29E3 | 22 (14,655 bp) | — |
| *Euglena gracilis* Δ9 elongase (U.S. patent applications No. 11/601563 and 11/601564) ("EgD9e") | 31 (777 bp) | 24 (258 AA) |
| Synthetic Δ9 elongase derived from *Euglena gracilis* (U.S. patent applications No. 11/601563 and 11/601564), codon-optimized for expression in *Yarrowia lipolytica* ("EgD9eS") | 23 (777 bp) | 24 (258 AA) |
| Synthetic $C_{16/18}$ elongase derived from *Mortierella alpina* ELO3 (U.S. patent application No. 11/253882), codon-optimized for expression in *Yarrowia lipolytica* ("ME3S") | 25 (828 bp) | 26 (275 AA) |
| Plasmid pY116 | 27 (8739 bp) | — |
| Plasmid pKO2UF8289 | 28 (15,304 bp) | — |
| Synthetic mutant Δ8 desaturase, derived from *Euglena gracilis* (U.S. patent application No. 11/635258) ("Mutant EgD8S-23") | 29 (1272 bp) | 30 (422 AA) |
| Plasmid pZKSL-555R | 32 (13,707 bp) | — |

TABLE 1-continued

Summary Of Gene And Protein SEQ ID Numbers

| Description and Abbreviation | Nucleic acid SEQ ID NO. | Protein SEQ ID NO. |
|---|---|---|
| *Euglena gracilis* Δ5 desaturase (U.S. patent application No. 60/801172) ("EgD5") | 37 (1350 bp) | 34 (449 AA) |
| Synthetic Δ5 desaturase derived from *Euglena gracilis* (U.S. patent application No. 60/801172), codon-optimized for expression in *Yarrowia lipolytica* ("EgD5S") | 33 (1350 bp) | 34 (449 AA) |
| Synthetic Δ5 desaturase derived from *Peridinium* sp. CCMP626 (U.S. patent application No. 60/801119), codon-optimized for expression in *Yarrowia lipolytica* ("RD5S") | 35 (1392 bp) | 36 (463 AA) |
| Plasmid pPrD17S | 38 (3806 bp) | — |
| Plasmid pZUF17 | 39 (8165 bp) | — |
| Plasmid pZUFPrD17S | 40 (8174 bp) | — |

DETAILED DESCRIPTION OF THE INVENTION

All patents, patent applications, and publications cited herein are incorporated by reference in their entirety. This specifically includes the following Applicants' Assignee's co-pending applications: U.S. Pat. No. 7,125,672, U.S. Pat. No. 7,189,559, U.S. Pat. No. 7,192,762, U.S. patent application Ser. No. 10/840,579 and Ser. No. 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. No. 10/985,254 and Ser. No. 10/985,691 (filed Nov. 10, 2004), U.S. patent application Ser. No. 10/987,548 (filed Nov. 12, 2004), U.S. patent application Ser. No. 11/024,545 and Ser. No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/253,882 (filed Oct. 19, 2005), U.S. patent application Ser. No. 11/264,784 and Ser. No. 11/264,737 (filed Nov. 1, 2005), U.S. patent application Ser. No. 11/265,761 (filed Nov. 2, 2005), U.S. Patent Application No. 60/795,810 (filed Apr. 28, 2006), U.S. Patent Application No. 60/793,575 (filed Apr. 20, 2006), U.S. Patent Application No. 60/796,637 (filed May 2, 2006), U.S. Patent Applications No. 60/801,172 and No. 60/801,119 (filed May 17, 2006), U.S. Patent Application No. 60/853,563 (filed Oct. 23, 2006), U.S. Patent Application No. 60/855,177 (filed Oct. 30, 2006), U.S. patent application Ser. No. 11/601,563 and Ser. No. 11/601,564 (filed Nov. 16, 2006), U.S. patent application Ser. No. 11/635,258 (filed Dec. 7, 2006) and U.S. patent application Ser. No. 11/613,420 (filed Dec. 20, 2006).

In accordance with the subject invention, Applicants identify novel Oomycota Δ17 desaturase enzymes and genes encoding the same that may be used for the manipulation of biochemical pathways for the production of healthful PUFAs. Thus, the subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

As used herein the term "invention" or "present invention" is intended to refer to all aspects and embodiments of the invention as described in the claims and specification herein and should not be read so as to be limited to any particular embodiment or aspect.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell. "Microbial oils" or "single cell oils" are those oils naturally produced by microorganisms during their lifespan.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A "metabolic pathway", or "biosynthetic pathway", in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane.

More specifically, "PUFA biosynthetic pathway enzymes" refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of interest herein are: 1.) Δ8 desaturases that will catalyze the conversion of EDA to DGLA and/or ETrA to ETA; 2.) Δ5 desaturases that catalyze the conversion of DGLA to ARA and/or ETA to EPA; 3.) Δ6 desaturases that catalyze the conversion of LA to GLA and/or ALA to STA; 4.) Δ4 desaturases that catalyze the conversion of DPA to DHA; 5.) Δ12 desaturases that catalyze the conversion of oleic acid to LA; 6.) Δ15 desaturases that catalyze the conversion of LA to ALA and/or GLA to STA; and 7.) Δ9 desaturases that catalyze the conversion of palmitate to palmitoleic acid (16:1) and/or stearate to oleic acid (18:1).

Of particular interest herein are Δ17 desaturases that desaturate a fatty acid between the $17^{th}$ and $18^{th}$ carbon atom numbered from the carboxyl-terminal end of the molecule and which, for example, catalyze the conversion of ARA to EPA (and optionally DGLA to ETA). In the art, Δ17 desaturases (and also Δ15 desaturases) are also occasionally referred to as "omega-3 desaturases", "w-3 desaturases", and/or "ω-3 desaturases", based on their ability to convert ω-6 fatty acids into their ω-3 counterparts (e.g., conversion of LA into ALA or DGLA into ETA and ARA into EPA, respectively).

Some desaturases have activity on two or more substrates. Based on this ability, these enzymes can be further classified with respect to their desaturase activities as being either "monofunctional" or "bifunctional". In some embodiments, it is most desirable to empirically determine the specificity of a fatty acid desaturase by transforming a suitable host with the gene for the fatty acid desaturase and determining its effect on the fatty acid profile of the host.

More specifically, Δ17 desaturases are defined herein as those fatty acid desaturases having monofunctional or bifunctional Δ17 desaturase activity, wherein Δ17 desaturase activity is the conversion of ARA to EPA and/or DGLA to ETA. The term "monofunctional Δ17 desaturase", "monofunctional Δ17 desaturase activity" or "exclusive Δ17 desaturase activity" refers to a Δ17 desaturase that is capable of converting ARA to EPA and/or DGLA to ETA but not LA to ALA. In contrast, "bifunctional Δ17 desaturase", "bifunctional Δ17 desaturase activity" or "primary Δ17 desaturase activity" refers to a Δ17 desaturase that preferentially converts ARA to EPA and/or DGLA to ETA but additionally has limited ability to convert LA into ALA (thus exhibiting primarily Δ17 desaturase activity and limited Δ15 desaturase activity).

It should be noted that Δ17 desaturases can have specificities other than Δ17 and Δ15 desaturation that are not relevant in this classification. It should also be noted that the distinction between monofunctional and bifunctional Δ17 desaturases is a practical one and not absolute; e.g., the same enzyme may function with either monofunctional or bifunctional Δ17 desaturase activity, depending on the level of its expression or growth condition.

For the purposes herein, the term "PsD17" refers to a Δ17 desaturase enzyme (SEQ ID NO:2) isolated from *Phytophthora sojae*, encoded by SEQ ID NO:1. In contrast, the term "PsD17S" refers to a synthetic Δ17 desaturase derived from *Phytophthora sojae* that is codon-optimized for expression in *Yarrowia lipolytica* (i.e., SEQ ID NOs:3 and 4). Based on analyses described herein, PsD17 and PsD17S are further classified as bifunctional Δ17 desaturases.

Similarly, the term "PrD17" refers to a Δ17 desaturase enzyme (SEQ ID NO:6) isolated from *Phytophthora ramorum*, encoded by SEQ ID NO:5. In contrast, the term "PrD17S" refers to a synthetic Δ17 desaturase derived from *Phytophthora ramorum* that is codon-optimized for expression in *Yarrowia lipolytica* (i.e., SEQ ID NOs:7 and 6). Based on analyses described herein, PrD17 and PrD17S are further classified as monofunctional Δ17 desaturases.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in PCT Publication No. WO 2004/101757. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase).

The term "oomycetes" refers to a group of heterotrophic organisms generally known as the water molds and downy mildews. They are filamentous protists that must absorb their food from the surrounding water or soil, or may invade the body of another organism to feed. As such, oomycetes play an important role in the decomposition and recycling of decaying matter. *Phytophthora* is a genus of the Oomycetes, comprising fifty-nine different species. Although oomycetes have similarities to fungi through convergent evolution, they are not fungi (as previously thought); instead, the oomycetes are part of the kingdom Stramenopiles and are thereby distinct from plants, fungi and animals. Diatoms and golden-brown and brown algae (e.g., kelp) are also included within kingdom Stramenopiles.

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

As used herein, an "isolated nucleic acid fragment" or "isolated nucleic acid molecule" will be used interchangeably and refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular Oomycete proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al. (1992) *Comput. Appl. Biosci.* 8:189-191) and found in the MegAlign program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al. (1992) *Comput. Appl. Biosci.* 8:189-191) and found in the MegAlign v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Indeed, any integer amino acid identity from 70% to 100% may be useful in describing the present invention, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

An Overview: Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ6 desaturase/Δ6 elongase pathway", ω-6 fatty acids are formed as follows: (1) LA is converted to GLA by a Δ6 desaturase; (2) GLA is converted to DGLA by a $C_{18/20}$ elongase; and (3) DGLA is converted to ARA by a Δ5 desaturase. Alternatively, the "Δ6 desaturase/Δ6 elongase pathway" can be utilized for formation of ω-3 fatty acids as follows: (1) LA is converted to ALA, the first of the ω-3 fatty acids, by a Δ15 desaturase; (2) ALA is converted to STA by a Δ6 desaturase; (3) STA is converted to ETA by a $C_{18/20}$ elongase; (4) ETA is converted to EPA by a Δ5 desaturase; (5) EPA is converted to DPA by a $C_{20/22}$ elongase; and, (6) DPA is converted to DHA by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ9 elongase and Δ8 desaturase. More specifically, LA and ALA may be converted to EDA and ETrA, respectively, by a Δ9 elongase; then, a Δ8 desaturase converts EDA to DGLA and/or ETrA to ETA.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, oomycetes, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or, 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, consideration of each enzyme's conversion efficiency is also a variable to consider when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Identification of Δ17 Desaturases

Sequences of the Δ17 desaturases of the invention, isolated from both *Phytophthora sojae* and *P. ramorum* and described herein, were first reported by the U.S. Department of Energy's Joint Genome Institute (JGI; Walnut Creek, Calif.). However, it should be noted that although the sequences were known, their function as a Δ17 desaturase was not elucidated before the findings described herein. Applicants are the first to recognize the specific Δ17 desaturase activity of these polypeptides.

In pursuing the correct activity for these sequences a *P. infestans* desaturase ("PiD17"; SEQ ID NO:9) was used as a query in BLAST searches against the JGI databases. This lead to the identification of two PiD17 homologs; specifically, the *P. sojae* homolog, designated herein as "PsD17" (SEQ ID NOs:1 and 2), and the *P. ramorum* homolog, designated herein as "PrD17" (SEQ ID NOs:5 and 6).

It was desirable to modify the wildtype PsD17 and PrD17 desaturases to optimize the expression of each enzyme for use in an alternate host though codon optimization. Use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Subsequently, the coding sequence for a polypeptide of interest having e.g., desaturase activity can be synthesized in whole or in part using the codons preferred in the host species.

The wildtype PsD17 and PrD17 desaturases were codon-optimized for expression in *Yarrowia lipolytica*, as shown below in Table 3.

reveals that the most similar known sequences (i.e., the *Phytophthora infestans* "ω3 desaturase" of PCT Publication No. WO 2005/083053; see also GenBank Accession No. CAJ30870) are about 91.4% identical to the amino acid sequence of PsD17S (SEQ ID NO:4) reported herein over a length of 361 amino acids using a Clustal W alignment algorithm (MegAlign™, DNASTAR, supra). In contrast, there was 90.9% identity between the amino acid sequences of the *P. infestans* "ω3 desaturase" and PsD17 (SEQ ID NO:2).

Comparison of the PrD17S nucleotide base and deduced amino acid sequences to public databases reveals that the most similar known sequences (i.e., the *P. infestans* "ω3 desaturase", supra) are about 89.5% identical to the amino acid sequence of PrD17S (SEQ ID NO:6) reported herein over a length of 361 amino acids using a Clustal W alignment algorithm (supra).

Within the context of the present invention preferred amino acid fragments are at least about 70%-80% identical to the PsD17S and PrD17S sequences herein, where those sequences that are at least about 85%-90% identical are particularly suitable and those sequences that are at least about 95% identical are most preferred. Preferred PsD17S and PrD17S encoding nucleic acid sequences corresponding to the instant ORFs are those encoding active proteins and which are at least about 70%-80% identical to the nucleic acid sequences of PsD17S and PrD17S reported herein, respectively, where those sequences that are at least 85%-90% identical are particularly suitable and those sequences that are at least about 95% identical are most preferred.

Upon identification of the Oomycete polypeptides described above, the specificity of each codon-optimized fatty acid desaturase was determined by transformation into a

TABLE 3

Codon-Optimized Δ17 Desaturases For ω-3 Biosynthesis In *Y. lipolytica*

| Wildtype (WT) Δ17 | SEQ ID NOs Of WT Δ17 | Total Bases Modified In Codon-Opt. Gene | Total Codons Modified In Codon-Opt. Gene | Change In GC Content From WT to Codon-Opt.Gene | Codon-Opt. Δ17 | SEQ ID NOs Of Codon-Opt. Δ17 |
|---|---|---|---|---|---|---|
| PsD17 (*P. sojae*) | 1, 2 | 175 of 1092 bp (16.0%) | 168 of 364 codons (46.2%) | 65.1% to 54.5% | PsD17S | 3, 4 |
| PrD17 (*P. ramorum*) | 5, 6 | 168 of 1086 bp (15.5%) | 160 of 362 codons (44.2%) | 64.4% to 54.5% | PrD17S | 7, 6 |

One skilled in the art would be able to use the teachings herein to create various other codon-optimized Δ17 desaturases suitable for optimal expression in alternate hosts (i.e., other than *Yarrowia lipolytica*), based on the wildtype PsD17 and PrD17 sequences. Accordingly, the instant invention relates to any codon-optimized Δ17 desaturase that is derived from the wildtype PsD17 and PrD17 (i.e., encoded by SEQ ID NOs:2 and 6, respectively). This includes, but is not limited to, the nucleotide sequences set forth in SEQ ID NOs:3 and 7, which encode synthetic Δ17 desaturase proteins (i.e., PsD17S and PrD17S, as set forth in SEQ ID NOs:4 and 6, respectively) that were codon-optimized for expression in *Yarrowia lipolytica.*

More specifically, comparison of the PsD17S nucleotide base and deduced amino acid sequences to public databases suitable host (i.e., *Yarrowia lipolytica*) and determination of its effect on the fatty acid profile of the host (Examples 5, 8 and 12). As expected, both PsD17S and PrD17S possessed Δ17 desaturase activity, such that the enzymes were capable of catalyzing conversion of ARA to EPA. Specifically, the ARA to EPA conversion efficiency of PsD17S was 40% and 98% (based on determination in two different strains of *Y. lipolytica* and under different growth conditions), while the ARA to EPA conversion efficiency of PrD17S was 49%. Conversion efficiency was measured according to the following formula: ([product]/[substrate+product])*100, where 'product' includes the immediate product and all products in the pathway derived from it.

Unexpectedly, however, PsD17S additionally possessed limited Δ15 desaturase activity (i.e., the LA to ALA conversion efficiency was 15%), while PrD17S did not (i.e., the LA to ALA conversion efficiency was less than 1%). Thus, the *Phytophthora sojae* desaturases are defined herein as bifunctional Δ17 desaturases, while the *Phytophthora ramorum* desaturases are defined herein as monofunctional Δ17 desaturases.

Identification and Isolation of Homologs

Any of the instant desaturase sequences (i.e., PsD17, PrD17, PsD17S, PrD17S) or portions thereof may be used to search for Δ17 desaturase homologs in the same or other bacterial, algal, fungal, Oomycete or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ17 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ17 desaturase nucleic acid fragments described herein (or any homologs identified thereof) may be used to isolate genes encoding homologous proteins from the same or other bacterial, algal, fungal, Oomycete or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. U.S.A.,* 82:1074 (1985); or strand displacement amplification (SDA), Walker, et al., *Proc. Nat. Acad. Sci. U.S.A.,* 89:392 (1992)]; and 3.) methods of library construction and screening by complementation.

For example, genes encoding similar proteins or polypeptides to the Δ17 desaturases described herein could be isolated directly by using all or a portion of the instant nucleic acid fragments as DNA hybridization probes to screen libraries from any desired yeast, fungus or oomycete using methodology well known to those skilled in the art (wherein those yeast or fungus producing EPA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the poly-adenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl. Acad. Sci. U.S.A.,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl. Acad. Sci. U.S.A.,* 86:5673 (1989); Loh et al., *Science,* 243:217 (1989)).

In other embodiments, any of the Δ17 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the Δ17 desaturase nucleic acid fragments described herein are exchanged with a functional domain in an alternate desaturase gene to thereby result in a novel protein.

Methods for Production of Various ω-3 and/or ω-6 Fatty Acids

It is expected that introduction of chimeric genes encoding the Δ17 desaturases described herein (i.e., PsD17, PrD17, PsD17S, PrD17S or other mutant enzymes, codon-optimized enzymes or homologs thereof), under the control of the appropriate promoters will result in increased production of EPA in the transformed host organism, respectively. As such, the present invention encompasses a method for the direct production of PUFAs comprising exposing a fatty acid substrate (i.e., ARA) to the desaturase enzymes described herein (e.g., PsD17, PrD17, PsD17S, PrD17S), such that the substrate is converted to the desired fatty acid product (i.e., EPA).

More specifically, it is an object of the present invention to provide a method for the production of EPA in a host cell (e.g., oleaginous yeast), wherein the host cell comprises:

a.) an isolated nucleotide molecule encoding a Δ17 desaturase polypeptide, selected from the group consisting of:
  i.) an isolated nucleotide molecule encoding a Δ17 desaturase polypeptide having at least 90.9% identity when compared to a polypeptide having the amino acid sequence as set forth in SEQ ID NO:2, based on the Clustal method of alignment;
  ii.) an isolated nucleotide molecule encoding a Δ17 desaturase polypeptide having at least 91.4% identity when compared to a polypeptide having the amino acid sequence as set forth in SEQ ID NO:4, based on the Clustal method of alignment;
  iii.) an isolated nucleotide molecule encoding a Δ17 desaturase polypeptide having at least 89.5% identity when compared to a polypeptide having an amino acid sequence as set forth in SEQ ID NO:6, based on the Clustal method of alignment; and, b) a source of ARA;

wherein the host cell is grown under conditions such that the Δ17 desaturase gene is expressed and the ARA is converted to EPA, and wherein the EPA is optionally recovered.

The person of skill in the art will recognize that the broad substrate range of the Δ17 desaturase will allow for the use of the enzyme for the conversion of dihomo-γ-linolenic acid to eicosatetraenoic acid. Accordingly the invention provides a method for the production of eicosatetraenoic acid comprising providing a host cell comprising:

a.) an isolated nucleotide molecule encoding a Δ17 desaturase polypeptide, selected from the group consisting of:
  i.) an isolated nucleotide molecule encoding a Δ17 desaturase polypeptide having at least 90.9% identity when compared to a polypeptide having the amino acid sequence as set forth in SEQ ID NO:2, based on the Clustal method of alignment;
  ii.) an isolated nucleotide molecule encoding a Δ17 desaturase polypeptide having at least 91.4% identity when compared to a polypeptide having the amino acid sequence as set forth in SEQ ID NO:4, based on the Clustal method of alignment; and,
  iii.) an isolated nucleotide molecule encoding a Δ17 desaturase polypeptide having at least 89.5% identity when compared to a polypeptide having an amino acid sequence as set forth in SEQ ID NO:6, based on the Clustal method of alignment;

b.) a source of dihomo-γ-linolenic acid;

c.) growing the host cell comprising a nucleotide molecule of step (a) under conditions wherein the nucleic acid molecule encoding the Δ17 desaturase polypeptide is expressed and the dihomo-γ-linolenic acid is converted to eicosatetraenoic acid; and, d.) optionally recovering the eicosatetraenoic acid of step (c).

In an alternate embodiment, based on the bifunctionality of the *Phytophthora sojae* Δ17 desaturases, it is an object of the present invention to provide a method for the production of ALA in a host cell (e.g., oleaginous yeast), wherein the host cell comprises:

a.) an isolated nucleotide molecule encoding a bifunctional Δ17 desaturase polypeptide, selected from the group consisting of:
  i.) an isolated nucleotide molecule encoding a Δ17 desaturase polypeptide having at least 90.9% identity when compared to a polypeptide having the amino acid sequence as set forth in SEQ ID NO:2, based on the Clustal method of alignment; and,
  ii.) an isolated nucleotide molecule encoding a Δ17 desaturase polypeptide having at least 91.4% identity when compared to a polypeptide having the amino acid sequence as set forth in SEQ ID NO:4, based on the Clustal method of alignment;

b) a source of LA;

wherein the host cell is grown under conditions such that the bifunctional Δ17 desaturase gene is expressed and the LA is converted to ALA, and wherein the ALA is optionally recovered.

Alternatively, each Δ17 desaturase gene and its corresponding enzyme product described herein can be used indirectly for the production of ω-3 fatty acids (see PCT Publication No. WO 2004/101757). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ17 desaturases described herein (e.g., PsD17, PrD17, PsD17S, PrD17S or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ5 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases, $C_{20/22}$ elongases) to result in higher levels of production of longer-chain ω-3 fatty acids (e.g., EPA, DPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ17 desaturase, based on the complete sequences described herein, the complement of those complete sequences, substantial portions of those sequences, codon-optimized desaturases derived therefrom and those sequences that are substantially homologous thereto. For example, the targeted disruption of the Δ17 desaturase (and optionally a Δ15 desaturase) in a host organism produces a mutant strain that has diminished ability to synthesize ω-3 fatty acids. This mutant strain could be useful for the production of "pure" ω-6 fatty acids (without co-synthesis of ω-3 fatty acids).

Expression Systems, Cassettes and Vectors

The genes and gene products of the instant sequences described herein may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate host cells via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see U.S. patent application Ser. No. 11/265,761, corresponding to PCT Publication No. WO2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and, 6.) the codon usage within the cloned gene, such that its frequency approaches the frequency of preferred codon usage of the host cell. Each of these types of modifications are encompassed in the present invention, as means to further optimize expression of the Δ17 desaturases described herein.

Transformation of Host Cells

Once the DNA encoding a polypeptide suitable for expression in an appropriate host cell has been obtained, it is placed in a plasmid vector capable of autonomous replication in the host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology,* 194:186-187 (1991)]), protoplast fusion, biolistic impact, electroporation, microinjection, or any other method that introduces the gene of interest into the host cell.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in PCT Publication No. WO 2004/101757 and PCT Publication No. WO 2005/003310.

Following transformation, substrates suitable for the instant Δ17 desaturases (and, optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis

Knowledge of the sequences of the present Δ17 desaturases will be useful for manipulating ω-3 and/or ω-6 fatty acid biosynthesis in various host cells. This may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art. For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication No. WO 2006/055322 [U.S. Patent Publication No. 2006-0094092-A1], PCT Publication No. WO 2006/052870 [U.S. Patent Publication No. 2006-0115881-A1] and PCT Publication No. WO 2006/052871 [U.S. Patent Publication No. 2006-0110806-A1], respectively, as are desirable manipulations in the TAG biosynthetic pathway and the TAG degradation pathway (and associated techniques thereof).

Preferred Hosts for Recombinant Expression of Δ17 Desaturases

Host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention were initially isolated for expression in an oleaginous yeast (and in particular *Yarrowia lipolytica*); however, it is contemplated that because transcription, translation and the protein biosynthetic apparatus is highly conserved, any bacteria, yeast, algae, oomycete and/or filamentous fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.,* 82(1):43-9 (2002)).

Specific teachings applicable for engineering EPA and DHA in *Y. lipolytica* are provided in U.S. patent application Ser. No. 11/265,761 and Ser. No. 11/264,737, respectively. Detailed means for the synthesis and transformation of expression vectors comprising Δ17 desaturases in oleaginous yeast (i.e., *Yarrowia lipolytica*) are provided in PCT Publications No. WO 2004/101757 and No. WO 2006/052870. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020) and/or the Lip2 gene locus (GenBank Accession No. AJ012632)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast $Ura^-$ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997).

Other preferred microbial hosts include oleaginous bacteria, algae, Oomycetes and other fungi; and, within this broad group of microbial hosts, of particular interest are microorganisms that synthesize ω-3/ω-6 fatty acids. Thus, for example, transformation of *Mortierella alpina* (which is commercially used for production of ARA) with any of the present Δ17 desaturase genes under the control of inducible or regulated promoters could yield a transformant organism capable of synthesizing EPA. The method of transformation of *M. alpina* is described by Mackenzie et al. (*Appl. Environ. Microbiol.,* 66:4655 (2000)). Similarly, methods for transformation of Thraustochytriales microorganisms are disclosed in U.S. Pat. No. 7,001,772.

In alternate preferred embodiments, the present invention provides a variety of plant hosts for transformation with the Δ17 desaturases described herein. Plants so transformed can be monocotyledonous plants or dicotyledonous plants, and preferably they belong to a class of plants identified as oleaginous (e.g., oilseed plants). Examples of preferred oilseed plant hosts include, but are not limited to: soybean (*Glycine* and *Soja* sp.), corn (*Zea mays*), flax (*Linum* sp.), rapeseed (*Brassica* sp.), primrose, canola, maize, safflower (*Carthamus* sp.) and sunflower (*Helianthus* sp.). Means for overexpression of fatty acid desaturases in oilseed plants (e.g., construction of expression cassettes, transformation, selection, etc.) are described in PCT Publication No. WO 2005/047479.

No matter what particular host is selected for expression of the Δ17 desaturases described herein, multiple transformants must be screened in order to obtain a strain displaying the desired expression level and pattern. Such screening may be accomplished by Southern analysis of DNA blots (Southern, *J. Mol. Biol.,* 98:503 (1975)), Northern analysis of mRNA expression (Kroczek, *J. Chromatogr. Biomed. Appl.,* 618 (1-2):133-145 (1993)), Western and/or Elisa analyses of protein expression, phenotypic analysis or GC analysis of the PUFA products.

Fermentation Processes for Omega Fatty Acid Production

The transformed host cell is grown under conditions that optimize expression of chimeric desaturase genes and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in PCT Publication No. WO 2004/101757, as are various suitable fermentation process designs (i.e., batch, fed-batch and continuous) and considerations during growth.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Comparisons of genetic sequences were accomplished using DNASTAR software (DNA Star, Inc.).

Unless otherwise specified, BLAST (Basic Local Alignment Search Tool; Altschul, S. F., et al., *J. Mol. Biol.,* 215: 403-410 (1993) and *Nucleic Acids Res.,* 25:3389-3402 (1997)) searches were conducted to identity isolated sequences having similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). Sequences were translated in all reading frames and compared for similarity to all publicly available protein sequences contained in the "nr" database, using the BLASTX algorithm (Gish, W. and States, D. J. *Nature Genetics,* 3:266-272 (1993)) provided by the National Center for Biotechnology Information (NCBI). The results of BLAST comparisons summarizing the sequence to which a query sequence had the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol. Biotechnol.,* 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of leucine, lysine and/or uracil were added as appropriate to a final concentration of 0.01% (thereby producing "MMLe", "MMLys" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

High Glucose Media ("HGM") was prepared as follows: 6.3 g/L $KH_2PO_4$, 27 g/L $K_2HPO_4$ and 80 g/L glucose (pH 7.5).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.,* 37:911-917 (1959)). Fatty acid methyl esters were prepared by transesterification of the lipid extract with sodium methoxide (Roughan, G., and Nishida I. *Arch Biochem Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Identification of a *Phytophthora sojae* Gene Encoding Δ17 Desaturase

The U.S. Department of Energy's Joint Genome Institute ("JGI"; Walnut Creek, Calif.) created version 1.0 of the *Phytophthora sojae* genome (estimated genome size is 95 Mbp). This genomic sequence was generated using a whole genome shotgun strategy and comprises a total of 19,276 gene models.

Using the amino acid sequence of the Δ17 desaturase of *Phytophthora infestans* (GenBank Accession No. CAJ30870; designated as "PiD17" herein and corresponding to SEQ ID NO:9) as a query sequence, a TBLASTN (BLAST protein versus translated nucleotide) search was conducted against JGI's *Phytophthora sojae* database (using the default parameters available from JGI). One *P. sojae* ORF located on scaffold 17:338148-339167 was found to share extensive homology with PiD17 (i.e., 91.8% identity and 95.6% similarity, with an Expectation value of 0). Based on this homology, the *P. sojae* ORF was tentatively identified as a Δ17 desaturase and was designated as "PsD17". When the 1092 bp DNA sequence of PsD17 (SEQ ID NO:1) was retrieved from the database, it was found to encode a polypeptide of 363 amino acids in length (SEQ ID NO:2). Amino acid sequence alignment using a ClustalW analysis (MegAlign™ program of DNASTAR software) showed that there was 90.9% identity between PiD17 and PsD17; in contrast, the nucleotide sequences shared only 86.6% identity.

The sequence homology of PsD17 to all publicly available protein sequences contained in the "nr" database (see General Methods) was also determined by conducting protein-protein BLAST searches using PsD17 (SEQ ID NO:2) as the query sequence. Based on this analysis, PsD17 was found to share the most homology with the omega-3 fatty acid desaturase of *Saprolegnia diclina* (GenBank Accession No. AA20444); specifically, PsD17 had 60% identity and 74% similarity with the amino acid sequence of GenBank Accession No. AA20444 with an Expectation value of 7E-117. Additionally, PsD17 had 39% identity and 57% similarity with the amino acid sequence of the fatty acid desaturase of *Anabaena variabilis* ATCC #29413 (GenBank Accession No. ABA23809), with an Expectation value of 4E-57.

Example 2

Synthesis of a Codon-Optimized Δ17 Desaturase Gene ("PsD17S") for *Yarrowia lipolytica*

The codon usage of the Δ17 desaturase gene of *Phytophthora sojae* was optimized for expression in *Yarrowia lipolytica*, in a manner similar to that described in U.S. Pat. No. 7,125,672. Specifically, a codon-optimized Δ17 desaturase gene (designated "PsD17S", SEQ ID NOs:3 and 4) was designed based on the coding sequence of PsD17 (SEQ ID NOs:1 and 2), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 175 bp of the 1092 bp coding region were modified (16.0%) and 168 codons were optimized (46.2%). The GC content was reduced from 65.1% within the wild type gene (i.e., PsD17) to 54.5% within the synthetic gene (i.e., PsD17S). A NcoI site and NotI sites were incorporated around the translation initiation codon and after the stop codon of PsD17S (SEQ ID NO:3), respectively. FIG. 2 shows a comparison of the nucleotide sequences of PsD17 and PsD17S. At the amino acid level, PsD17S lacked the third and forth amino acid, as compared with the wild type PsD17; thus, the total length of PsD17S is 361 amino acids (SEQ ID NO:4). The designed PsD17S gene was synthesized by GenScript Corporation (Piscataway, N.J.) and cloned into pUC57 (GenBank Accession No. Y14837) to generate pPsD17S (SEQ ID NO:10; FIG. 3A).

Example 3

Generation of Construct pFmPsD17S

The present Example describes the construction of plasmid pFmPsD17S comprising a chimeric FBAINm::PsD17S::XPR gene. Plasmid pFmPsD17S (SEQ ID NO:13; FIG. 3D) was constructed by three-way ligation using fragments from plasmids pKUNF1-KEA, pDMW214 and pPsD17S. Plasmid pFmPsD17S was utilized to test functional expression of PsD17S, as described in Example 5, infra.

Plasmid pKUNF1-KEA pKUNF1-KEA (SEQ ID NO:11; FIG. 3B) comprises a chimeric FBAINm::E1S::Pex20 gene. The "FBAINm" promoter within this chimeric gene (PCT Publication No. WO 05/049805; also identified as "Fba1+intron" in FIG. 3B) refers to a synthetic promoter that is derived from the "FBAIN" promoter, wherein the FBAIN promoter refers to the 5' upstream untranslated region in front of the 'ATG' translation initiation codon of a fructose-bisphosphate aldolase enzyme (E.C. 4.1.2.13) encoded by the fba1 gene and that is necessary for expression, plus a portion of 5' coding region that has an intron of the fba1 gene. The FBAINm promoter is modified from FBAIN, in that FBAINm has a 52 bp deletion between the ATG translation initiation codon and the intron of the FBAIN promoter (thereby including only 22 amino acids of the N-terminus) and a new translation consensus motif after the intron. Furthermore, while the FBAIN promoter generates a fusion protein when fused with the coding region of a gene to be expressed, the FBAINm promoter does not generate such a fusion protein.

Table 4 summarizes the components of plasmid pKUNF1-KEA.

TABLE 4

Description Of Plasmid pKUNF1-KEA (SEQ ID NO: 11)

| RE Sites And Nucleotides Within SEQ ID NO: 11 | Description Of Fragment And Chimeric Gene Components |
|---|---|
| PmeI/PacI (360-2596) | FBAINm::EL1S::Pex20, comprising: FBAINm: *Yarrowia lipolytica* FBAINm promoter (PCT Publication No. WO 2005/049805) EL1S: codon-optimized elongase 1 gene (PCT Publication No. WO 2004/101753), derived from *Mortierella alpina* (GenBank Accession No. AX464731) Pex20: Pex20 terminator sequence of *Yarrowia* Pex20 gene (GenBank Accession No. AF054613) |
| AscI/BsiWI 3387-2596 | 5' portion of *Yarrowia* Ura3 gene (GenBank Accession No. AJ306421) |
| PacI/SphI 6617-6095 | 3' portion of *Yarrowia* Ura3 gene (GenBank Accession No. AJ306421) |

Plasmid pDMW214 pDMW214 (SEQ ID NO:12; FIG. 3C) is a shuttle plasmid that replicates both in *E. coli* and *Yarrowia lipolytica*. It contained the following components:

TABLE 5

Description Of Plasmid pDMW214 (SEQ ID NO: 12)

| RE Sites And Nucleotides Within SEQ ID NO: 12 | Description Of Fragment And Chimeric Gene Components |
|---|---|
| 1150-270 | ColE1 plasmid origin of replication |
| 2080-1220 | Ampicillin-resistance gene ($Amp^R$) |
| 2979-4256 | *Yarrowia* autonomous replication sequence (ARS18; GenBank Accession No. A17608) |
| PmeI/SphI 6501-4256 | *Yarrowia* Leu2 gene (GenBank Accession No. AF260230) |
| 6501-1 | FBAIN::GUS::XPR, comprising: FBAIN: *Yarrowia lipolytica* FBAIN promoter (PCT Publication No. WO 2005/049805) GUS: *E. coli* gene encoding β-glucuronidase (Jefferson, R. A. Nature, 14; 342: 837-838 (1989)) XPR: ~100 bp of the 3' region of the *Yarrowia* Xpr gene (GenBank Accession No. M17741) |

Final Construction of Plasmid pFmPsD17S

The PmeI/NcoI fragment of plasmid pKUNF1-KEA (FIG. 3B; comprising the FBAINm promoter) and the NcoI/NotI fragment of plasmid pPsD17S (FIG. 3A; comprising the synthetic Δ17 desaturase gene PsD17S) were used directionally to replace the PmeI/Not I fragment of pDMW214 (FIG. 3C). This resulted in generation of pFmPsD17S (SEQ ID NO:13; FIG. 3D), comprising a chimeric FBAINm::PsD17S::XPR gene. Thus, the components of pFmPsD17S were as described in Table 6 below.

TABLE 6

Description Of Plasmid pFmPsD17S (SEQ ID NO: 13)

| RE Sites And Nucleotides Within SEQ ID NO: 13 | Description Of Fragment And Chimeric Gene Components |
|---|---|
| 5551-1305 | *Yarrowia* autonomous replication sequence (ARS18; GenBank Accession No. A17608) |

TABLE 6-continued

Description Of Plasmid pFmPsD17S (SEQ ID NO: 13)

| RE Sites And Nucleotides Within SEQ ID NO: 13 | Description Of Fragment And Chimeric Gene Components |
|---|---|
| 7769-1269 | FBAINm::PsD17S::XPR, comprising:<br>FBAINm: *Yarrowia lipolytica* FBAINm promoter (PCT Publication No. WO 2005/049805)<br>PsD17S: codon-optimized Δ17 desaturase gene (SEQ ID NO: 3), derived from *P. sojae*<br>XPR: ~100 bp of the 3' region of the *Yarrowia* Xpr gene (GenBank Accession No. M17741) |
| 2418-1538 | ColE1 plasmid origin of replication |
| 3348-2488 | Ampicillin-resistance gene ($Amp^R$) |
| PmeI/SphI 7769-5524 | *Yarrowia* Leu2 gene (GenBank Accession No. AF260230), |

Example 4

Generation of *Yarrowia lipolytica* Strain Y2047 to Produce About 11% ARA of Total Lipids Via the Δ6 Desaturase/Δ6 Elongase Pathway The present Example describes the construction of strain Y2047, derived from *Yarrowia lipolytica* ATCC #20362, capable of producing 11% ARA relative to the total lipids via expression of a Δ6 desaturase/Δ6 elongase pathway (FIG. 4A). Y2047 has been deposited under the terms of the Budapest Treaty and bears the ATCC number PTA-7186. Additionally, construction of Y2047 has been described in co-pending U.S. patent application Ser. No. 11/265,761, herein incorporated by reference.

The development of strain Y2047 first required the construction of strain M4 (producing 8% DGLA).

Generation of M4 Strain to Produce About 8% DGLA of Total Lipids

Construct pKUNF12T6E (FIG. 4B; SEQ ID NO:14) was generated to integrate four chimeric genes (comprising a Δ12 desaturase, a Δ6 desaturase and two $C_{18/20}$ elongases) into the Ura3 loci of wild type *Yarrowia* strain ATCC #20362, to thereby enable production of DGLA. The pKUNF12T6E plasmid contained the following components:

TABLE 7

Description Of Plasmid pKUNF12T6E (SEQ ID NO: 14)

| RE Sites And Nucleotides Within SEQ ID NO: 14 | Description Of Fragment And Chimeric Gene Components |
|---|---|
| AscI/BsiWI (9420-8629) | 784 bp 5' portion of *Yarrowia* Ura3 gene (GenBank Accession No. AJ306421) |
| SphI/PacI 12128-1 | 516 bp 3' portion of *Yarrowia* Ura3 gene (GenBank Accession No. AJ306421) |
| SwaI/BsiWI (6380-8629) | FBAIN::EL1S::Pex20, comprising:<br>FBAIN: *Yarrowia lipolytica* FBAIN promoter (PCT Publication No. WO 2005/049805)<br>EL1S: codon-optimized elongase 1 gene (PCT Publication No. WO 2004/101753), derived from *Mortierella alpina* (GenBank Accession No. AX464731)<br>Pex20: Pex20 terminator sequence from *Yarrowia* Pex20 gene (GenBank Accession No. AF054613) |
| BglII/SwaI (4221-6380) | TEF::Δ6S::Lip1, comprising:<br>TEF: *Yarrowia lipolytica* TEF promoter (GenBank Accession No. AF054508)<br>Δ6S: codon-optimized Δ6 desaturase gene (PCT Publication No. WO 2004/101753), derived from *Mortierella alpina* (GenBank Accession No. AF465281)<br>Lip1: Lip1 terminator sequence from *Yarrowia* Lip1 gene (GenBank Accession No. Z50020) |
| PmeI/ClaI (4207-1459) | FBA::F.Δ12::Lip2, comprising:<br>FBA: *Yarrowia lipolytica* FBA promoter (PCT Publication No. WO 2005/049805)<br>F.Δ12: *Fusarium moniliforme* Δ12 desaturase gene (PCT Publication No. WO 2005/047485)<br>Lip2: Lip2 terminator sequence from *Yarrowia* Lip2 gene (GenBank Accession No. AJ012632) |
| ClaI/PacI (1459-1) | TEF::EL2S::XPR, comprising:<br>TEF: *Yarrowia lipolytica* TEF promoter (GenBank Accession No. AF054508)<br>EL2S: codon-optimized elongase gene (SEQ ID NO: 15), derived from *Thraustochytrium aureum* (U.S. Pat. No. 6,677,145)<br>XPR: ~100 bp of the 3' region of the *Yarrowia* Xpr gene (Gen Bank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura− strains. Single colonies of Ura− strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 $Ura^-$ strains produced about 6% DGLA of total lipids. There were 2 strains (i.e., strains M4 and 13-8) that produced about 8% DGLA of total lipids.

Generation of Y2047 Strain to Produce About 11% ARA of Total Lipids

Construct pDMW271 (FIG. 4C; SEQ ID NO:17) was generated to integrate three Δ5 chimeric genes into the Leu2 gene of *Yarrowia* strain M4. Plasmid pDMW271 contained the following components, as described in Table 8:

TABLE 8

Description Of Plasmid pDMW271 (SEQ ID NO: 17)

| RE Sites And Nucleotides Within SEQ ID NO: 17 | Description Of Fragment And Chimeric Gene Components |
|---|---|
| AscI/BsiWI (5520-6315) | 788 bp 5' portion of *Yarrowia* Leu2 gene (GenBank Accession No. AF260230) |
| SphI/PacI 2820-2109 | 703 bp 3' portion of *Yarrowia* Leu2 gene (GenBank Accession No. AF260230) |
| SwaI/BsiWI (8960-6315) | FBAIN::MAΔ5::Pex20, comprising:<br>FBAIN: *Yarrowia lipolytica* FBAIN promoter (PCT Publication No. WO 2005/049805) |

TABLE 8-continued

Description Of Plasmid pDMW271 (SEQ ID NO: 17)

| RE Sites And Nucleotides Within SEQ ID NO: 17 | Description Of Fragment And Chimeric Gene Components |
|---|---|
| | MAΔ5: *Mortierella alpina* Δ5 desaturase gene (GenBank Accession No. AF067654) |
| | Pex20: Pex20 terminator sequence of *Yarrowia* Pex20 gene (GenBank Accession No. AF054613) |
| SwaI/ClaI (8960-11055) | TEF::MAΔ5::Lip1, comprising: TEF: *Yarrowia lipolytica* TEF promoter (GenBank Accession No. AF054508) |
| | MAΔ5: *Mortierella alpina* Δ5 desaturase gene (GenBank Accession No. AF067654) |
| | Lip1: Lip1 terminator sequence of *Yarrowia* Lip1 gene (GenBank Accession No. Z50020) |
| PmeI/ClaI (12690-11055) | *Yarrowia* Ura3 gene (GenBank Accession No. AJ306421) |
| ClaI/PacI (1-2109) | TEF::HΔ5S::Pex16, comprising: TEF: *Yarrowia lipolytica* TEF promoter (GenBank Accession No. AF054508) |
| | HΔ5S: codon-optimized Δ5 desaturase gene (SEQ ID NO: 18), derived from *Homo sapiens* (GenBank Accession No. NP_037534) |
| | Pex16: Pex16 terminator sequence of *Yarrowia* Pex16 gene (GenBank Accession No. U75433) |

Plasmid pDMW271 was digested with AscI/SphI, and then used to transform strain M4 according to the General Methods. Following transformation, the cells were plated onto MMLe plates and maintained at 30° C. for 2 to 3 days. The individual colonies grown on MMLe plates were picked and streaked onto MM and MMLe plates. Those colonies that could grow on MMLe plates but not on MM plates were selected as Leu2⁻ strains. Single colonies of Leu2⁻ strains were then inoculated into liquid MMLe media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW271 transformants, but not in the parental M4 strain. Specifically, among the 48 selected Leu2⁻ transformants with pDMW271, there were 35 strains that produced less than 5% ARA of total lipids, 12 strains that produced 6-8% ARA, and 1 strain that produced about 11% ARA of total lipids in the engineered *Yarrowia*. The strain that produced 11% ARA was named "Y2047".

Example 5

Expression of the Codon-Optimized Δ17 Desaturase Gene ("PsD17S") in *Yarrowia lipolytica* Strain Y2047

Plasmid pFmPsD17S (FIG. 3D; Example 3) was transformed into *Yarrowia lipolytica* strain Y2047 (Example 4), as described in the General Methods. The transformant cells were plated onto MM selection media plates and maintained at 30° C. for 2 to 3 days. Eight (8) transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

The GC results showed that there were about 3% ARA and 2% EPA of total lipids produced in all 8 transformants. The conversion efficiency whereby PsD17S converted ARA to EPA in these 8 strains was at an average rate of about 40%. The conversion efficiency was measured according to the following formula: ([product]/[substrate+product])*100, where 'product' includes the immediate product and all products in the pathway derived from it. Thus, this experimental data demonstrated that the codon-optimized Δ17 desaturase gene (SEQ ID NO:3) derived from *P. sojae* efficiently desaturated ARA to EPA.

Example 6

Generation of Construct pZP3-P7U

The present Example describes the construction of plasmid pZP3-P7U comprising a chimeric YAT::PsD17S::Lip1 gene, which was designed to integrate into the Pox3 locus (GenBank Accession No. XP_503244) of the *Yarrowia* genome. Plasmid pZP3-P7U was utilized to test functional expression of PsD17S, as described in Example 8, infra. The components of pZP3-P7U were as described in Table 9 below.

TABLE 9

Description Of Plasmid pZP3-P7U (SEQ ID NO: 20)

| RE Sites And Nucleotides Within SEQ ID NO: 20 | Description Of Fragment And Chimeric Gene Components |
|---|---|
| AscI/BsiWI (4030-4800) | 770 bp 5' portion of *Yarrowia* Pox3 gene (GenBank Accession No. AJ001301) |
| PacI/SphI (504-1300) | 826 bp 3' portion of *Yarrowia* Pox3 gene (GenBank Accession No. AJ001301) |
| ClaI/SwaI 7133-4960 | YAT::PsD17S::Lip1, comprising: YAT: *Yarrowia* YAT promoter (PCT Publication No. WO 2006/052754) |
| | PsD17S: codon-optimized Δ17 desaturase gene (SEQ ID NO: 3), derived from *P. sojae* |
| | Lip1: Lip1 terminator sequence of *Yarrowia* Lip1 gene (GenBank Accession No. Z50020) |
| ClaI/EcoRI 7133-1 | LoxP::Ura3::LoxP, comprising: LoxP sequence (SEQ ID NO: 21) |
| | *Yarrowia* Ura3 gene (GenBank Accession No. AJ306421) |
| | LoxP sequence (SEQ ID NO: 21) |

Example 7

Generation of *Yarrowia lipolytica* Strain Y4070 to Produce About 12% ARA of Total Lipids Via the Δ9 Elongase/Δ8 Desaturase Pathway The present Example describes the construction of strain Y4070, derived from *Yarrowia lipolytica* ATCC #20362, capable of producing about 12% ARA relative to the total lipids via expression of a Δ9 elongase/Δ8 desaturase pathway (FIG. 6A). Strain Y4070 was utilized to test the functional expression of PsD17S in Example 8 and PrD17S in Example 12, infra.

The development of strain Y4070 required the construction of strain Y2224 (a FOA resistant mutant from an autonomous mutation of the Ura3 gene of wildtype *Yarrowia* strain ATCC #20362), strain Y4001 (producing 17% EDA with a Leu− phenotype), strain Y4001U (producing 17% EDA with a Leu− and Ura− phenotype), strain Y4036 (producing 18% DGLA with a Leu− phenotype) and strain Y4036U (producing 18% DGLA with a Leu− and Ura− phenotype).

Generation of Strain Y2224

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Generation of Strain Y4001 to Produce about 17% EDA of Total Lipids

Strain Y4001 was created via integration of construct pZKLeuN-29E3 (FIG. 6B). This construct, comprising four chimeric genes (i.e., a Δ12 desaturase, a $C_{16/18}$ elongase and two Δ9 elongases), was integrated into the Leu2 loci of strain Y2224 to thereby enable production of EDA.

Construct pZKLeuN-29E3 contained the components shown in Table 10.

TABLE 10

Description of Plasmid pZKLeuN-29E3 (SEQ ID NO: 22)

| RE Sites And Nucleotides Within SEQ ID NO: 22 | Description Of Fragment And Chimeric Gene Components |
|---|---|
| BsiW I/Asc I (7797-7002) | 788 bp 3' portion of *Yarrowia* Leu2 gene (GenBank Accession No. AF260230) |
| Sph I/Pac I (4302-3591) | 703 bp 5' portion of *Yarrowia* Leu2 gene (GenBank Accession No. AF260230) |
| Swa I/BsiW I (10500-7797) | GPD::F.D12::Pex20, comprising:<br>GPD: *Yarrowia lipolytica* GPD promoter (PCT Publication No. WO 2005/003310)<br>F.D12: *Fusarium moniliforme* Δ12 desaturase gene (PCT Publication No. WO 2005/047485)<br>Pex20: Pex20 terminator sequence from *Yarrowia* Pex20 gene (GenBank Accession No. AF054613) |
| Bgl II/Swa I (12526-10500) | Exp pro::EgD9E::Lip1, comprising:<br>Exp pro: *Yarrowia lipolytica* export protein (EXP1) promoter (PCT Publication No. WO 2006/052870 and U.S. patent application No. 11/265761)<br>EgD9E: codon-optimized Δ9 elongase (SEQ ID NO: 23), derived from *Euglena gracilis* ("EgD9eS"; U.S. patent applications No. 11/601563 and No. 11/601564)<br>Lip1: Lip1 terminator sequence from *Yarrowia* Lip1 gene (GenBank Accession No. Z50020) |
| Pme I/Cla I (12544-1) | FBAINm::EgD9S::Lip2, comprising:<br>FBAINm: *Yarrowia lipolytica* FBAINm promoter (PCT Publication No. WO 2005/049805)<br>EgD9S: codon-optimized Δ9 elongase gene (SEQ ID NO: 23), derived from *Euglena gracilis* ("EgD9eS"; U.S. patent applications No. 11/601563 and No. 11/601564)<br>Lip2: Lip2 terminator sequence from *Yarrowia* Lip2 gene (GenBank Accession No. AJ012632) |
| Cla I/EcoR I (1-1736) | LoxP::Ura3::LoxP, comprising:<br>LoxP sequence (SEQ ID NO: 21)<br>*Yarrowia* Ura3 gene (GenBank Accession No. AJ306421)<br>LoxP sequence (SEQ ID NO: 21) |
| EcoR I/Pac I (1736-3591) | NT::ME3S::Pex16, comprising:<br>NT: *Yarrowia lipolytica* YAT1 promoter (Patent Publication No. U.S. 2006/0094102-A1)<br>ME3S: codon-optimized $C_{16/18}$ elongase gene (SEQ ID NO: 25), derived from *M. alpina* (U.S. patent application No. 11/253882 and also PCT Publication No. WO 2006/052870)<br>Pex16: Pex16 terminator sequence of *Yarrowia* Pex 16 gene (GenBank Accession No. U75433) |

Plasmid pZKLeuN-29E3 was digested with Asc I/Sph I, and then used for transformation of *Y. lipolytica* strain Y2224 (i.e., ATCC #20362 Ura3−) according to the General Methods. The transformant cells were plated onto MMLeu media plates and maintained at 30° C. for 2 to 3 days. The colonies were picked and streaked onto MM and MMLeu selection plates. The colonies that could grow on MMLeu plates but not on MM plates were selected as Leu− strains. Single colonies of Leu− strains were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EDA in the transformants containing the 4 chimeric genes of pZKLeuN-29E3, but not in the *Yarrowia* Y2224 control strain. Most of the selected 36 Leu− strains produced about 12 to 16.9% EDA of total lipids. There were 3 strains (i.e., strains #11, #30 and #34) that produced about 17.4%, 17% and 17.5% EDA of total lipids; they were designated as strains Y4001, Y4002 and Y4003, respectively.

Generation of Strain Y4001U (Leu−, Ura−) to Produce about 17% EDA of Total Lipids Strain Y4001U was created via temporary expression of the Cre recombinase enzyme in plasmid pY116 (FIG. 6C) within strain Y4001 to produce a Leu− and Ura− phenotype. Construct pY116 contained the fo

TABLE 11

Description of Plasmid pY116 (SEQ ID NO: 27)

| RE Sites And Nucleotides Within SEQ ID NO: 27 | Description Of Fragment And Chimeric Gene Components |
|---|---|
| 1328-448 | ColE1 plasmid origin of replication |
| 2258-1398 | Ampicillin-resistance gene ($Amp^R$) for selection in *E. coli* |
| 3157-4461 | *Yarrowia* autonomous replication sequence (ARS18; GenBank Accession No. A17608) |
| PacI/SawI 6667-4504 | *Yarrowia* Leu2 gene (GenBank Accession No. AF260230) |
| Swa I/Pme I (6667-218 | GPAT::Cre::XPR2, comprising:<br>GPAT: *Yarrowia lipolytica* GPAT promoter (PCT Publication No. WO 2006/031937)<br>Cre: *Enterobacteria* phage P1 Cre gene for recombinase protein (GenBank Accession No. X03453)<br>XPR2: ~100 bp of the 3' region of the *Yarrowia* Xpr gene (GenBank Accession No. M17741) |

Plasmid pY116 was used for transformation of freshly grown Y4001 cells according to the General Methods. The transformant cells were plated onto MMLeu+Ura plates (MMU plus Leucine) containing 280 μg/mL sulfonylurea and maintained at 30° C. for 3 to 4 days. Four colonies were picked, inoculated into 3 mL liquid YPD media at 30° C. and shaken at 250 rpm/min for 1 day. The cultures were diluted to 1:50,000 with liquid MMLeu+Ura media, and 100 μL was plated onto new YPD plates and maintained at 30° C. for 2 days. Colonies were picked and streaked onto MMLeu and MMLeu+Ura selection plates. The colonies that could grow on MMLeu+Ura plates but not on MMLeu plates were selected and analyzed by GC to confirm the presence of C20:2 (EDA). One strain, having a Leu− and Ura− phenotype, produced about 17% EDA of total lipids and was designated as Y4001U.

Generation of Y4036 Strain to Produce about 18% DGLA of Total Lipids

Construct pKO2UF8289 (FIG. 7A; SEQ ID NO:28) was generated to integrate four chimeric genes (comprising a Δ12 desaturase, one Δ9 elongase and two mutant Δ8 desaturases)

into the Δ12 loci of strain Y4001U1, to thereby enable production of DGLA. Construct pKO2UF8289 contained the following components:

TABLE 12

Description of Plasmid pKO2UF8289 (SEQ ID NO: 28)

| RE Sites And Nucleotides Within SEQ ID NO: 28 | Description Of Fragment And Chimeric Gene Components |
|---|---|
| AscI/BsiWI (10304-9567) | 5' portion of *Yarrowia* Δ12 desaturase gene (PCT Publication No. WO 2004/104167) |
| EcoRI/SphI (13568-13012) | 3' portion of *Yarrowia* Δ12 desaturase gene (PCT Publication No. WO 2004/104167) |
| SwaI/BsiWI (7055-9567) | FBAINm::EgD8M::Pex20, comprising: FBAINm: *Yarrowia lipolytica* FBAINm promoter (PCT Publication No. WO 2005/049805) EgD8M: Synthetic Δ8 desaturase mutant EgD8S-23 (SEQ ID NO: 29), derived from *Euglena gracilis* (U.S. patent application No. 11/635258) Pex20: Pex20 terminator sequence from *Yarrowia* Pex20 gene (GenBank Accession No. AF054613) |
| SwaI/PmeI (7055-4581) | YAT::F.D12::OCT, comprising: YAT: *Yarrowia lipolytica* YAT1 promoter (Patent Publication No. US 2006/0094102-A1) F.D12: *Fusarium moniliforme* Δ12 desaturase gene (PCT Publication No. WO 2005/047485) OCT terminator sequence of *Yarrowia* OCT gene (GenBank Accession No. X69988) |
| PmeI/PacI (4581-2124) | EXP::EgD8M::Pex16, comprising: EXP: *Yarrowia lipolytica* export protein (EXP1) promoter (PCT Publication No. WO 2006/052870 and U.S. patent application No. 11/265761) EgD8M: Synthetic Δ8 desaturase mutant EgD8S-23 (SEQ ID NO: 29), derived from *Euglena gracilis* (U.S. patent application No. 11/635258) Pex16: Pex16 terminator of *Yarrowia* Pex16 gene (GenBank Accession No. U75433) |
| PmeI/ClaI (2038-1) | GPAT::EgD9e::Lip2, comprising: GPAT: *Yarrowia lipolytica* GPAT promoter (PCT Publication No. WO 2006/031937) EgD9e: *Euglena gracilis* Δ9 elongase gene (SEQ ID NO: 31) (U.S. patent applications No. 11/601563 and 11/601564) Lip2: Lip2 terminator sequence from *Yarrowia* Lip2 gene (GenBank Accession No. AJ012632) |
| ClaI/EcoRI (13568-1) | LoxP::Ura3::LoxP, comprising: LoxP sequence (SEQ ID NO: 21) *Yarrowia* Ura3 gene (GenBank Accession No. AJ306421) LoxP sequence (SEQ ID NO: 21) |

The pKO2UF8289 plasmid was digested with AscI/SphI, and then used for transformation of strain Y4001U1 according to the General Methods. The transformant cells were plated onto MMLeu plates and maintained at 30° C. for 2 to 3 days. The colonies were picked and streaked onto MMLeu selection plates at 30° C. for 2 days. These cells were then inoculated into liquid MMLeu at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKO2UF8289, but not in the parent Y4001U1 strain. Most of the selected 96 strains produced between 7 and 13% DGLA of total lipids. There were 6 strains (i.e., #32, #42, #60, #68, #72 and #94) that produced about 15%, 13.8%, 18.2%, 13.1%, 15.6% and 13.9% DGLA of total lipids. These six strains were designated as Y4034, Y4035, Y4036, Y4037, Y4038 and Y4039, respectively.

Generation of Strain Y4036U (Leu−, Ura3−) to Produce about 18% DGLA of Total Lipids Construct pY116 (FIG. 6C; SEQ ID NO:27) was utilized to temporarily express a Cre recombinase enzyme in strain Y4036. This released the LoxP sandwiched Ura3 gene from the genome.

Plasmid pY116 was used to transform strain Y4036 according to the General Methods. Following transformation, the cells were plated onto MMLeu+Ura plates (MMU plus Leucine) and maintained at 30° C. for 2 to 3 days. The individual colonies grown on MMLeu+Ura plates were picked, and streaked into YPD liquid media at 30° C. and shaken at 250 rpm/min for 1 day to cure the pY116 plasmid. The grown cultures were streaked on MMLeu+Ura u plates. After two days at 30° C., the individual colonies were re-streaked on MMLeu+Ura, MMU and MMLeu plates. Those colonies that could grow on MMLeu+Ura, but not on MMU or MMLeu plates were selected. One of these strains with Leu− and Ura− phenotypes was designated as Y4036U (Ura−, Leu−).

Generation of Y4070 Strain to Produce about 12% ARA of Total Lipids

Construct pZKSL-555R (FIG. 7B; SEQ ID NO:32) was generated to integrate three Δ5 desaturase genes into the Lys loci of strain Y4036U, to thereby enable production of ARA. The pZKSL-555R plasmid contained the following components:

TABLE 13

Description of Plasmid pZKSL-555R (SEQ ID NO: 32)

| RE Sites And Nucleotides Within SEQ ID NO: 32 | Description Of Fragment And Chimeric Gene Components |
|---|---|
| AscI/BsiWI (3321-2601) | 720 bp 5' portion of *Yarrowia* Lys5 gene (GenBank Accession No. M34929) |
| PacI/SphI (6716-6029) | 687 bp 3' portion of *Yarrowia* Lys5 gene (GenBank Accession No. M34929) |
| BglII/BsiWI (15-2601) | EXP::EgD5S::Pex20, comprising: EXP: *Yarrowia lipolytica* export protein (EXP1) promoter (WO 2006/052870 and U.S. patent application No. 11/265761) EgD5S: codon-optimized Δ5 desaturase (SEQ ID NO: 33), derived from *Euglena gracilis* (U.S. Provisional Application No. 60/801172) Pex20: Pex20 terminator sequence from *Yarrowia* Pex20 gene (GenBank Accession No. AF054613) |
| ClaI/PmeI (11243-1) | YAT::RD5S::OCT, comprising: YAT: *Yarrowia lipolytica* YAT1 promoter (Patent Publication US 2006/0094102-A1) RD5S: codon-optimized Δ5 desaturase (SEQ ID NO: 35), derived from *Peridinium* sp. CCMP626 (U.S. Provisional Application No. 60/801119) OCT: OCT terminator sequence of *Yarrowia* OCT gene (GenBank Accession No. X69988) |
| EcoRI/PacI (9500-6716) | FBAIN::EgD5WT::Aco, comprising: FBAIN: *Yarrowia lipolytica* FBAIN promoter (WO 2005/049805) EgD5WT: *Euglena gracilis* Δ5 desaturase (SEQ ID NO: 35; U.S. Provisional Application No. 60/801172) with elimination of internal BglII, HindIII and NcoI restriction enzyme sites Aco: Aco terminator of *Yarrowia* Aco gene (GenBank Accession No. AJ001300), |
| EcoRIClaI (9500-11243) | *Yarrowia* Leu2 gene (GenBank Accession No. M37309) |

The pZKSL-555R plasmid was digested with AscI/SphI, and then used for transformation of strain Y4036U according to the General Methods. The transformant cells were plated onto MMLeuLys plates (MMLeu plus Lysine) and maintained at 30° C. for 2 to 3 days. Single colonies were then re-streaked onto MMLeuLys plates, and then inoculated into liquid MMLeuLys at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in the transformants containing the 3 chimeric genes of pZKSL-555R, but not in the parent Y4036 strain. Most of the selected 96 strains produced ~10% ARA of total lipids. There were 4 strains (i.e., #57, #58, #69 and #75) that produced about 11.7%, 11.8%, 11.9% and 11.7% ARA of total lipids. These four strains were designated as Y4068, Y4069, Y4070 and Y4071, respectively. Further analyses showed that the three chimeric genes of pZKSL-555R were not integrated into the Lys5 site in the Y4068, Y4069, Y4070 and Y4071 strains. All strains possessed a Lys+ phenotype. The final genotype of strain Y4070 with respect to wildtype *Yarrowia lipolytica* ATCC #20362 was Ura3−, Leu+, Lys+, GPD::F.D12::Pex20, YAT::F.D12::OCT, YAT::ME3S::Pex16, GPAT:: EgD9e::Lip2, Exp:: EgD9eS::Lip1, FBAINm::EgD9eS::Lip2, FBAINm:: EgD8M::Pex20, EXP::EgD8M::Pex16, FBAIN::EgD5WT:: Aco, EXP::EgD5S::Pex20, YAT::RD5S::OCT.

Example 8

Expression of the Codon-Optimized Δ17 Desaturase Gene ("PsD17S") in *Yarrowia lipolytica* Strain Y4070

Plasmid pZP3-P7U (FIG. 5; Example 6) was digested with AscI/SphI, and then used to transform *Yarrowia lipolytica* strain Y4070 according to the General Methods. Following transformation, the cells were plated onto MM plates and maintained at 30° C. for 2 to 3 days. Twelve (12) transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in high glucose media, and then grow for 5 days at 30° C. and shaken at 250 rpm/min. The cells were collected by centrifugation, lipids were extracted, and fatty acid methyl esters were prepared by trans-esterification, and subsequently analyzed with a Hewlett-Packard 6890 GC.

The GC results are shown below in Table 14. Fatty acids are identified as 16:0, 16:1, 18:0, 18:1 (oleic acid), LA (18:2), ALA, EDA (20:2), DGLA, ARA, ETrA (20:3), ETA and EPA; and the composition of each is presented as a % of the total fatty acids. "Δ17 Activity" was calculated according to the following formula: ([EPA]/[ARA+EPA])*100 and represents percent substrate conversion to EPA. "Δ15 Activity" was calculated according to the following formula: ([ALA]/[LA+ALA])*100 and represents percent substrate conversion to ALA.

TABLE 14

Functional Analysis Of PsD17S In *Yarrowia lipolytica* Strain Y4070

| pZP3-P7U Transformant in Y4070 | 16:0 | 16:1 | 18:0 | 18:1 | LA | ALA | EDA | DGLA | ARA | ETrA | ETA | EPA | Δ17 Activity % | Δ15 Activity % |
|---|---|---|---|---|---|---|---|---|---|---|---|---|---|---|
| 1 | 5.0 | 1.7 | 5.0 | 25.1 | 26.8 | 4.8 | 5.7 | 0.4 | 0.0 | 3.9 | 1.1 | 11.6 | 100 | 15 |
| 2 | 5.2 | 1.9 | 5.3 | 25.1 | 28.1 | 5.1 | 5.5 | 0.3 | 0.0 | 3.9 | 1.2 | 11.7 | 100 | 15 |
| 3 | 4.8 | 2.0 | 6.7 | 24.4 | 29.6 | 3.5 | 6.2 | 0.5 | 0.5 | 2.5 | 0.9 | 11.8 | 96 | 10 |
| 4 | 5.0 | 2.2 | 5.6 | 24.5 | 28.4 | 5.4 | 5.2 | 0.3 | 0.0 | 3.6 | 1.1 | 11.3 | 100 | 16 |
| 5 | 5.1 | 2.3 | 5.4 | 23.3 | 29.2 | 5.5 | 5.1 | 0.4 | 0.2 | 3.5 | 1.1 | 11.3 | 98 | 16 |
| 6 | 5.8 | 2.1 | 5.8 | 21.1 | 31.0 | 4.1 | 5.8 | 0.5 | 0.6 | 3.1 | 1.0 | 11.5 | 95 | 12 |
| 7 | 4.9 | 2.3 | 5.5 | 23.7 | 29.1 | 5.4 | 5.3 | 0.4 | 0.0 | 3.6 | 1.2 | 11.4 | 100 | 16 |
| 8 | 4.9 | 2.1 | 5.6 | 25.0 | 28.2 | 5.3 | 5.2 | 0.3 | 0.0 | 3.6 | 1.1 | 11.3 | 100 | 16 |
| 9 | 4.9 | 2.0 | 5.7 | 27.0 | 26.9 | 4.9 | 5.6 | 0.3 | 0.0 | 3.9 | 1.1 | 11.3 | 100 | 15 |
| 10 | 4.6 | 2.1 | 5.8 | 23.8 | 29.1 | 5.0 | 5.6 | 0.4 | 0.5 | 3.4 | 1.2 | 11.5 | 96 | 15 |
| 11 | 4.9 | 1.9 | 5.6 | 21.5 | 31.8 | 4.2 | 5.6 | 0.6 | 1.8 | 2.7 | 1.0 | 11.6 | 87 | 12 |
| 12 | 5.0 | 2.7 | 4.8 | 21.1 | 31.1 | 6.4 | 4.8 | 0.4 | 0.0 | 3.7 | 1.4 | 11.5 | 100 | 17 |
| Ave. | 5.0 | 2.1 | 5.6 | 23.8 | 29.1 | 5.0 | 5.5 | 0.4 | 0.3 | 3.5 | 1.1 | 11.5 | 98 | 15 |
| STD | 0.3 | 0.3 | 0.5 | 1.8 | 1.6 | 0.8 | 0.4 | 0.1 | 0.5 | 0.5 | 0.1 | 0.2 | | |

The GC results demonstrated that there were an average of 0.3% ARA and 11.5% EPA of total lipids produced in 12 transformants. The conversion efficiency whereby PsD17S converted ARA to EPA in these 12 strains was at an average rate of about 98%. The conversion efficiency was measured according to the following formula: ([product]/[substrate+product])*100, where 'product' includes the immediate product and all products in the pathway derived from it. Thus, this experimental data demonstrated that the codon-optimized Δ17 desaturase gene (SEQ ID NO:3) derived from *P. sojae* efficiently desaturated ARA to EPA.

There were also an average of 5% ALA and 29.1% LA of total lipids produced in the 12 transformants. The conversion efficiency whereby PsD17S converted LA to ALA in these 12 strains was at an average rate of about 15%. Additionally, there were EtrA and ETA produced in all 12 strains, suggesting that PsD17 might be able to convert EDA to EtrA and DGLA to ETA; however, it is difficult to calculate the conversion efficiency in these two cases, since the Δ9 elongase in strain Y4070 could convert the ALA to EtrA and the Δ8 desaturase could convert the EtrA to ETA.

It is clear that PsD17 had both Δ17 and Δ15 desaturase activities, thus functioning as a bifunctional desaturase as defined herein.

Example 9

Identification of a *Phytophthora ramorum* Gene Encoding Δ17 Desaturase

The U.S. Department of Energy's Joint Genome Institute ("JGI"; Walnut Creek, Calif.) created version 1.0 of the *Phytophthora ramorum* genome (estimated genome size is 65

Mbp). This genomic sequence was generated using a whole genome shotgun strategy and comprises a total of 16,066 gene models.

In a manner similar to that described in Example 1, the amino acid sequence of PiD17 (SEQ ID NO:9) was used as a query sequence to perform a TBLASTN search against JGI's *Phytophthora ramorum* database (using the default parameters available from JGI).

Two ORFs were found to share extensive homology with PiD17 in the genome sequence of *Phytophthora ramorum*. Specifically, ORF 80222 shared 89% identity and 94% similarity with SEQ ID NO:9, with an Expectation value of 0, Similarly, ORF48790 shared up to 40% identity and 61% similarity with SEQ ID NO:9, with an Expectation value of 6E-44. Based on these results, ORF 80222 was tentatively identified as a Δ17 desaturase and was designated as "PrD17".

When the 1086 bp DNA sequence of PrD17 (SEQ ID NO:5) was retrieved from the database, it was found to encode a polypeptide of 361 amino acids in length (SEQ ID NO:6). Amino acid sequence alignment using a ClustalW analysis (MegAlign™ program of DNASTAR software) showed that there was 89.5% identity between PiD17 and PrD17; in contrast, the nucleotide sequences shared only 85.7% identity.

The sequence homology of PrD17 was in turn compared with all publicly available protein sequences contained in the "nr" database (see General Methods) was also determined by conducting protein-protein BLAST searches using PrD17 (SEQ ID NO:6) as the query sequence. The sequence that showed the highest degree of similarity was that of the omega-3 fatty acid desaturase of *Saprolegnia diclina* (GenBank Accession No. AA20444), sharing 59% identity and 74% similarity, with an Expectation value of E-124. Additionally, PrD17 had 38% identity and 57% similarity with the amino acid sequence of the fatty acid desaturase of *Anabaena variabilis* ATCC #29413 (GenBank Accession No. ABA23809), with an Expectation value of 6E-61.

Example 10

Synthesis of a Codon-Optimized Δ17 Desaturase Gene ("PrD17S") for *Yarrowia lipolytica*

The codon usage of the Δ17 desaturase gene of *Phytophthora ramorum* was optimized for expression in *Yarrowia lipolytica*, in a manner similar to that described in Example 2. Specifically, a codon-optimized Δ17 desaturase gene (designated "PrD17S", SEQ ID NO:7) was designed based on the coding sequence of PrD17 (SEQ ID NOs:5 and 6), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 168 bp of the 1086 bp coding region were modified (15.5%) and 160 codons were optimized (44.2%). The GC content was reduced from 64.4% within the wild type gene (i.e., PrD17) to 54.5% within the synthetic gene (i.e., PrD17S). A NcoI site and NotI sites were incorporated around the translation initiation codon and after the stop codon of PrD17S (SEQ ID NO:7), respectively. FIG. 8 shows a comparison of the nucleotide sequences of PrD17 and PrD17S, None of the modifications in the codon-optimized gene changed the amino acid sequence of the encoded protein (SEQ ID NO:6). The designed PrD17S gene was synthesized by GenScript Corporation (Piscataway, N.J.) and cloned into pUC57 (GenBank Accession No. Y14837) to generate pPrD17S (FIG. 9A; SEQ ID NO:38).

Example 11

Generation of Construct pZuFPrD17S

The present Example describes the construction of plasmid pZuFPrD17S (FIG. 9B) comprising a chimeric FBAIN::PrD17S::Pex20 gene. Plasmid pZuFPrD17S was utilized to test functional expression of PrD17S, as described in Example 12, infra.

Specifically, plasmid pZuFPrD17S was constructed by using the NcoI/NotI fragment containing the PrD17S coding region of plasmid pPrD17S to replace the NcoI/NotI fragment of pZuF17 (FIG. 9C; SEQ ID NO:39). Thus, the components of pZuFPrD17S were as described in Table 15 below.

TABLE 15

Description Of Plasmid pZuFPrD17S (SEQ ID NO: 40)

| RE Sites And Nucleotides Within SEQ ID NO: 40 | Description Of Fragment And Chimeric Gene Components |
|---|---|
| EcoRI/ClaI 4203-5599 | *Yarrowia* autonomous replication sequence (ARS18; GenBank Accession No. A17608) |
| EcoRI/BsiWI 7152-1407 | FBAIN::PrD17S::Pex20, comprising:<br>FBAIN: *Yarrowia lipolytica* FBAINm promoter (PCT Publication No. WO 2005/049805)<br>PrD17S: codon-optimized Δ17 desaturase gene (SEQ ID NO: 7), derived from *P. ramorum*<br>Pex20: Pex20 terminator sequence of *Yarrowia* Pex20 gene (GenBank Accession No. AF054613) |
| 2443-1563 | ColE1 plasmid origin of replication |
| 3373-2513 | Ampicillin-resistance gene ($Amp^R$) |
| EcoRI/PacI 7130-5619 | *Yarrowia* Ura3 gene (GenBank Accession No. AJ306421) |

Example 12

Expression of the Codon-Optimized Δ17 Desaturase Gene PrD17S in *Yarrowia lipolytica* Strain Y4070

Plasmid pZuFPrD17S (FIG. 9B; Example 11) was transformed into *Yarrowia lipolytica* strain Y4070 (Example 8), as described in the General Methods. The transformant cells were plated onto MM selection media plates and maintained at 30° C. for 2 to 3 days. Ten (10) transformants grown on MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in high glucose media, and then grow for 5 days at 30° C. and shaken at 250 rpm/min. The cells were collected by centrifugation, lipids were extracted, and fatty acid methyl esters were prepared by trans-esterification, and subsequently analyzed with a Hewlett-Packard 6890 GC.

The GC results are shown below in Table 16. Fatty acids are identified as 16:0, 16:1, 18:0, 18:1 (oleic acid), LA (18:2), ALA, EDA (20:2), DGLA, ARA, ETrA (20:3), ETA and EPA; and the composition of each is presented as a % of the total fatty acids. "Δ17 Activity" was calculated according to the following formula: ([EPA]/[ARA+EPA])*100 and represents percent substrate conversion to EPA. "Δ15 Activity" was calculated according to the following formula: ([ALA]/[LA+ALA])*100 and represents percent substrate conversion to ALA.

TABLE 16

Functional Analysis Of PrD17S In *Yarrowia lipolytica* Strain Y4070

| pZUFPrD17S Transformant in Y4070 | 16:0 | 16:1 | 18:0 | 18:1 | LA | ALA | EDA | DGLA | ARA | ETrA | ETA | EPA | Δ17 Activity % | Δ15 Activity % |
|---|---|---|---|---|---|---|---|---|---|---|---|---|---|---|
| 1 | 6.2 | 2.3 | 5.3 | 15.3 | 38.3 | 0.5 | 7.5 | 2.4 | 7.3 | 0.6 | 0.4 | 7.6 | 51 | 1.3 |
| 2 | 6.5 | 2.3 | 5.0 | 14.0 | 40.2 | 0.5 | 7.2 | 2.5 | 7.6 | 0.5 | 0.4 | 7.7 | 50 | 1.2 |
| 3 | 5.7 | 2.1 | 5.5 | 15.3 | 38.7 | 0.5 | 7.8 | 2.5 | 7.5 | 0.5 | 0.5 | 7.4 | 50 | 1.3 |
| 4 | 7.8 | 2.8 | 3.8 | 13.8 | 40.0 | 0.3 | 7.4 | 2.0 | 7.7 | 0.4 | 0.0 | 6.3 | 45 | 0.7 |
| 5 | 5.5 | 2.0 | 5.6 | 15.7 | 38.0 | 0.5 | 8.0 | 2.5 | 7.1 | 0.5 | 0.5 | 7.3 | 51 | 1.4 |
| 6 | 7.7 | 3.0 | 4.1 | 13.2 | 41.0 | 0.3 | 6.7 | 1.8 | 7.7 | 0.4 | 0.0 | 7.2 | 48 | 0.7 |
| 7 | 6.1 | 1.7 | 4.8 | 15.3 | 38.5 | 0.4 | 7.7 | 2.4 | 7.7 | 0.5 | 0.4 | 7.3 | 49 | 1.1 |
| 8 | 6.9 | 2.2 | 4.6 | 15.5 | 39.7 | 0.5 | 7.2 | 2.4 | 7.1 | 0.5 | 0.4 | 7.2 | 50 | 1.3 |
| 9 | 7.4 | 2.7 | 4.1 | 14.4 | 41.0 | 0.3 | 7.2 | 2.3 | 7.5 | 0.4 | 0.0 | 6.9 | 48 | 0.7 |
| 10 | 7.1 | 2.6 | 4.4 | 13.7 | 40.6 | 0.5 | 6.7 | 2.5 | 7.7 | 0.5 | 0.4 | 7.3 | 48 | 1.2 |
| Ave. | 6.7 | 2.4 | 4.7 | 13.4 | 39.6 | 0.4 | 7.3 | 2.3 | 7.5 | 0.5 | 0.3 | 7.2 | 49 | 1.1 |
| STD | 0.8 | 0.4 | 0.6 | 4.3 | 1.1 | 0.1 | 0.4 | 0.2 | 0.2 | 0.1 | 0.2 | 0.4 | | |

Table 16 showed that there were an average of 7.5% ARA and 7.2% EPA of total lipids produced in the 10 transformants. The conversion efficiency whereby PrD17S converted ARA to EPA in these 10 strains was at an average rate of about 49%. The conversion efficiency was measured as described in Example 8. Thus, this experimental data demonstrated that the codon-optimized Δ17 desaturase gene (SEQ ID NO:5) derived from *P. ramorum* efficiently desaturated ARA to EPA.

There was an average of 0.4% ALA and 39.6% LA (C18:2) of total lipids produced in the 10 transformants. The conversion efficiency whereby PrD17S converted LA to ALA in these 10 strains was at an average rate of about only 1%.

Thus, PrD17S is identified herein as a monofunctional Δ17 desaturase, catalyzing conversion of ARA to EPA.

What is claimed is:

1. An isolated nucleic acid molecule selected from the group consisting of:

a.) an isolated nucleotide sequence encoding a Δ17 desaturase enzyme as set forth in SEQ ID NO:7; or, b.) an isolated nucleotide sequence that is completely complementary to (a).

2. A chimeric gene comprising the isolated nucleic acid molecule of claim 1 operably linked to suitable regulatory sequences.

3. A transformed *Yarrowia* sp. comprising the isolated nucleic acid molecule of claim 1.

* * * * *

SEQUENCE LISTING

```
<160> NUMBER OF SEQ ID NOS: 40

<210> SEQ ID NO 1
<211> LENGTH: 1092
<212> TYPE: DNA
<213> ORGANISM: Phytophthora sojae

<400> SEQUENCE: 1

atggcgtcca agcaggagca gccgtaccag ttcccgacgc tgacggagat caagcgctcg     60

ctgcccagcg agtgtttcga ggcgtccgtg ccgctctcgc tctactacac ggtgcgctgc    120

ctggtgatcg ccgtgtcgct ggccttcggg ctccaccacg cgcgctcgct gcccgtggtc    180

gagggcctct gggcgctgga cgccgcgctc tgcacgggct acgtgctgct gcagggcatc    240

gtgttctggg gcttcttcac cgtgggccat gacgccggcc acggcgcctt ctcgcgctac    300

cacctgctca acttcgtgat cggcaccttc atccactcgc tcatcctgac gcccttcgag    360

tcgtggaagc tcacgcaccg ccaccaccac aagaacacgg gcaacatcga ccgcgacgag    420

atcttctacc cgcagcgcaa ggccgacgac cacccgctct cgcgtaacct catcctggcg    480

ctgggcgccg cgtggttcgc ctacctggtc gagggcttcc cgccgcgcaa ggtcaaccac    540

ttcaacccgt tcgagccgct gttcgtccgc caggtgtccg ccgtggtcat ctcgctggcc    600

gcgcacttcg gcgtggccgc gctgtccatc tacctgagcc tgcagttcgg cttcaagacc    660

atggctatct actactacgg gcccgtgttc gtgttcggca gcatgctggt catcaccacc    720

ttcctgcacc acaacgacga ggagaccccc tggtacgccg actcggagtg gacctacgtc    780

aagggcaacc tctcgtcggt cgaccgctcc tacggcgcgc tcatcgacaa cctgagccac    840

aacatcggca cgcaccagat ccaccacctc ttccccatca tcccgcacta taagctcaag    900

cgcgccaccg aggccttcca ccaggcgttc cccgagctcg tgcgcaagag cgacgagccc    960
```

-continued

```
atcattaagg ccttcttccg cgtcggccgc ctctacgcca actacggcgt cgtggactcg   1020

gacgccaagc tcttcacgct caaggaggcc aaggccgtgt ccgaggcggc gaccaagact   1080

aaggccaact ga                                                        1092


<210> SEQ ID NO 2
<211> LENGTH: 363
<212> TYPE: PRT
<213> ORGANISM: Phytophthora sojae

<400> SEQUENCE: 2

Met Ala Ser Lys Gln Glu Gln Pro Tyr Gln Phe Pro Thr Leu Thr Glu
1               5                   10                  15

Ile Lys Arg Ser Leu Pro Ser Glu Cys Phe Glu Ala Ser Val Pro Leu
            20                  25                  30

Ser Leu Tyr Tyr Thr Val Arg Cys Leu Val Ile Ala Val Ser Leu Ala
        35                  40                  45

Phe Gly Leu His His Ala Arg Ser Leu Pro Val Val Glu Gly Leu Trp
    50                  55                  60

Ala Leu Asp Ala Ala Leu Cys Thr Gly Tyr Val Leu Leu Gln Gly Ile
65                  70                  75                  80

Val Phe Trp Gly Phe Phe Thr Val Gly His Asp Ala Gly His Gly Ala
                85                  90                  95

Phe Ser Arg Tyr His Leu Leu Asn Phe Val Ile Gly Thr Phe Ile His
            100                 105                 110

Ser Leu Ile Leu Thr Pro Phe Glu Ser Trp Lys Leu Thr His Arg His
        115                 120                 125

His His Lys Asn Thr Gly Asn Ile Asp Arg Asp Glu Ile Phe Tyr Pro
    130                 135                 140

Gln Arg Lys Ala Asp Asp His Pro Leu Ser Arg Asn Leu Ile Leu Ala
145                 150                 155                 160

Leu Gly Ala Ala Trp Phe Ala Tyr Leu Val Glu Gly Phe Pro Pro Arg
                165                 170                 175

Lys Val Asn His Phe Asn Pro Phe Glu Pro Leu Phe Val Arg Gln Val
            180                 185                 190

Ser Ala Val Val Ile Ser Leu Ala Ala His Phe Gly Val Ala Ala Leu
        195                 200                 205

Ser Ile Tyr Leu Ser Leu Gln Phe Gly Phe Lys Thr Met Ala Ile Tyr
    210                 215                 220

Tyr Tyr Gly Pro Val Phe Val Phe Gly Ser Met Leu Val Ile Thr Thr
225                 230                 235                 240

Phe Leu His His Asn Asp Glu Glu Thr Pro Trp Tyr Ala Asp Ser Glu
                245                 250                 255

Trp Thr Tyr Val Lys Gly Asn Leu Ser Ser Val Asp Arg Ser Tyr Gly
            260                 265                 270

Ala Leu Ile Asp Asn Leu Ser His Asn Ile Gly Thr His Gln Ile His
        275                 280                 285

His Leu Phe Pro Ile Ile Pro His Tyr Lys Leu Lys Arg Ala Thr Glu
    290                 295                 300

Ala Phe His Gln Ala Phe Pro Glu Leu Val Arg Lys Ser Asp Glu Pro
305                 310                 315                 320

Ile Ile Lys Ala Phe Phe Arg Val Gly Arg Leu Tyr Ala Asn Tyr Gly
                325                 330                 335

Val Val Asp Ser Asp Ala Lys Leu Phe Thr Leu Lys Glu Ala Lys Ala
            340                 345                 350
```

-continued

```
Val Ser Glu Ala Ala Thr Lys Thr Lys Ala Asn
        355                 360


<210> SEQ ID NO 3
<211> LENGTH: 1086
<212> TYPE: DNA
<213> ORGANISM: Phytophthora sojae
<220> FEATURE:
<221> NAME/KEY: misc_feature
<223> OTHER INFORMATION: synthetic delta-17 desaturase (codon-optimized)

<400> SEQUENCE: 3

atggctacca agcagcccta ccagttccct actctgaccg agatcaagcg atctctgccc     60

tccgagtgtt tcgaggcctc cgtgcctctc tctctgtact acaccgttcg atgcctggtc    120

attgctgtgt cgctcgcctt cggacttcac catgcacgat ctctgcccgt tgtcgaaggc    180

ctctgggctc tggatgccgc tctctgcacc ggttacgtgc tgctccaggg catcgtcttc    240

tggggattct ttactgttgg tcacgacgct ggacatggtg ccttctcccg ataccacctg    300

ctcaactttg tcatcggaac cttcattcac tctctcatcc ttacaccctt cgagtcctgg    360

aagctcaccc acagacacca tcacaagaac actggcaaca tcgaccgaga cgaaatcttc    420

taccctcaac gaaaggccga cgatcatcct ctgtctcgaa acctcattct ggctttgggt    480

gcagcctggt ttgcctacct ggtcgaaggc tttcctcccc gaaaggtcaa ccacttcaac    540

cccttcgagc ctctctttgt tcgacaggtc tctgccgtgg tcatttcgct ggctgcgcac    600

tttggagtgg ctgccctgtc catctacctc agcctgcagt tcggcttcaa gactatggcc    660

atctactact atggtcccgt ctttgtgttc ggatccatgc tcgtcattac tacctttctt    720

catcacaacg acgaagagac accttggtac gcagattcgg agtggaccta cgtcaaaggc    780

aacctgtcct ctgtcgaccg atcctacggt gccctcatcg acaacctttc tcacaacatc    840

ggaacccacc agattcatca cctctttccc atcattcctc actacaagct caagcgagct    900

accgaggcct tccatcaagc ctttcccgag ctggttcgaa agtccgacga acccatcatc    960

aaggcctttt tcagagtcgg ccgactctac gcaaactacg gtgtggtcga ctcggatgcc   1020

aagctgttca ctctcaagga ggccaaggct gtttccgaag ccgctaccaa gactaaggcc   1080

acctaa                                                              1086


<210> SEQ ID NO 4
<211> LENGTH: 361
<212> TYPE: PRT
<213> ORGANISM: Phytophthora sojae
<220> FEATURE:
<221> NAME/KEY: MISC_FEATURE
<223> OTHER INFORMATION: synthetic delta-17 desaturase (codon-optimized)

<400> SEQUENCE: 4

Met Ala Thr Lys Gln Pro Tyr Gln Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Cys Leu Val Ile Ala Val Ser Leu Ala Phe Gly
        35                  40                  45

Leu His His Ala Arg Ser Leu Pro Val Val Glu Gly Leu Trp Ala Leu
    50                  55                  60

Asp Ala Ala Leu Cys Thr Gly Tyr Val Leu Leu Gln Gly Ile Val Phe
65                  70                  75                  80
```

-continued

```
Trp Gly Phe Phe Thr Val Gly His Asp Ala Gly His Gly Ala Phe Ser
                85                  90                  95

Arg Tyr His Leu Leu Asn Phe Val Ile Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Phe Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Ala Ala His Phe Gly Val Ala Ala Leu Ser Ile
        195                 200                 205

Tyr Leu Ser Leu Gln Phe Gly Phe Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Arg Ala Thr Glu Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Ser Asp Ala Lys Leu Phe Thr Leu Lys Glu Ala Lys Ala Val Ser
            340                 345                 350

Glu Ala Ala Thr Lys Thr Lys Ala Thr
        355                 360


<210> SEQ ID NO 5
<211> LENGTH: 1086
<212> TYPE: DNA
<213> ORGANISM: Phytophthora ramorum

<400> SEQUENCE: 5

atggcgacta agcagccgta ccagttcccg accctgacgg agatcaagcg gtcgctgccc      60

agcgagtgct ttgaggcctc ggtgccgctg tcgctctact acacggtgcg catcgtggcc     120

atcgccgtgg cgctggcgtt cggcctcaac tacgcgcgcg cgctgcccgt ggtcgagagc     180

ttgtgggcgc tggacgctgc gctctgctgc ggttacgtgc tgctgcaggg catcgtgttc     240

tggggcttct tcacggtggg ccatgacgcc ggccacggcg ccttctcgcg ttaccacctg     300

ctcaacttcg tggtgggcac cttcatccac tcgctcatcc tcacgccctt cgagtcgtgg     360

aagctcacgc accgccacca ccacaagaac acgggcaaca ttgaccgcga cgagatcttc     420

tacccgcagc gcaaggccga cgaccacccg ctgtcgcgca acctcgtgct ggcgctcggc     480

gccgcgtggt tcgcctacct ggtcgagggc ttcccgcccc gcaaggtcaa ccacttcaac     540
```

-continued

```
ccattcgagc cgctgtttgt gcgccaggtg gccgccgtcg tcatctcgct ctccgcgcac    600

ttcgccgtgt tggcgctgtc cgtgtatctg agcttccagt tcggtctcaa gaccatggcg    660

ctctactact acggccccgt cttcgtgttc ggcagcatgc ttgtgatcac caccttcctg    720

catcacaatg acgaggagac cccatggtac ggagactccg actggaccta cgtcaagggc    780

aacctgtcgt ccgtggaccg gtcctacggc gcgttcatcg acaacctgag ccacaacatc    840

ggcacgcacc agatccacca cctcttcccc atcatcccgc actacaagct caaccgcgct    900

acggcggcat tccaccaggc cttccccgag ctcgtgcgca agagcgacga gccgatcctc    960

aaggccttct ggcgcgtcgg ccgactgtac gccaactacg gcgtcgtgga cccggacgcc   1020

aagctcttca cgctcaagga ggccaaggcg gcgtccgagg cggcgaccaa gaccaaggcc   1080

acctaa                                                               1086


<210> SEQ ID NO 6
<211> LENGTH: 361
<212> TYPE: PRT
<213> ORGANISM: Phytophthora ramorum

<400> SEQUENCE: 6

Met Ala Thr Lys Gln Pro Tyr Gln Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Ile Val Ala Ile Ala Val Ala Leu Ala Phe Gly
        35                  40                  45

Leu Asn Tyr Ala Arg Ala Leu Pro Val Val Glu Ser Leu Trp Ala Leu
    50                  55                  60

Asp Ala Ala Leu Cys Cys Gly Tyr Val Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Val Leu Ala Leu Gly
145                 150                 155                 160

Ala Ala Trp Phe Ala Tyr Leu Val Glu Gly Phe Pro Pro Arg Lys Val
                165                 170                 175

Asn His Phe Asn Pro Phe Glu Pro Leu Phe Val Arg Gln Val Ala Ala
            180                 185                 190

Val Val Ile Ser Leu Ser Ala His Phe Ala Val Leu Ala Leu Ser Val
        195                 200                 205

Tyr Leu Ser Phe Gln Phe Gly Leu Lys Thr Met Ala Leu Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Gly Asp Ser Asp Trp Thr
                245                 250                 255

Tyr Val Lys Gly Asn Leu Ser Ser Val Asp Arg Ser Tyr Gly Ala Phe
            260                 265                 270
```

-continued

```
Ile Asp Asn Leu Ser His Asn Ile Gly Thr His Gln Ile His His Leu
        275                 280                 285

Phe Pro Ile Ile Pro His Tyr Lys Leu Asn Arg Ala Thr Ala Ala Phe
    290                 295                 300

His Gln Ala Phe Pro Glu Leu Val Arg Lys Ser Asp Glu Pro Ile Leu
305                 310                 315                 320

Lys Ala Phe Trp Arg Val Gly Arg Leu Tyr Ala Asn Tyr Gly Val Val
                325                 330                 335

Asp Pro Asp Ala Lys Leu Phe Thr Leu Lys Glu Ala Lys Ala Ala Ser
            340                 345                 350

Glu Ala Ala Thr Lys Thr Lys Ala Thr
        355                 360


<210> SEQ ID NO 7
<211> LENGTH: 1086
<212> TYPE: DNA
<213> ORGANISM: Phytophthora ramorum
<220> FEATURE:
<221> NAME/KEY: misc_feature
<223> OTHER INFORMATION: synthetic delta-17 desaturase (codon-optimized)

<400> SEQUENCE: 7

atggctacca agcagcccta ccagttccct actctgaccg agatcaagcg atctcttccc     60

tccgagtgct ttgaagcctc ggtccctctg tccttgtact acaccgtgcg aatcgtcgct    120

attgccgttg ctctggcctt cggactcaac tacgctcgag cccttcccgt ggtcgagtct    180

ctgtgggcac tcgacgctgc cctttgttgc ggttacgttc tgctccaagg cattgtcttc    240

tggggattct ttaccgtggg tcacgatgct ggacatggtg ccttctctcg ataccacctg    300

ctcaactttg tcgttggcac ctttatccac tccctcattc ttactccctt cgagtcgtgg    360

aagctcacac atcgacacca tcacaagaac accggaaaca tcgaccgaga cgaaatcttc    420

taccctcagc gaaaggccga cgatcatcct ctgtctcgaa acctcgtcct ggctctcggt    480

gccgcttggt ttgcctacct tgtcgagggc tttcctcccc gaaaggtcaa ccacttcaac    540

cccttcgaac ctctgtttgt gcgacaggtg gctgccgttg tcatttccct ctctgctcac    600

ttcgccgtcc tggcactgtc cgtgtatctg agctttcagt tcggtctcaa gacaatggct    660

ctgtactact atggacccgt cttcgtgttc ggctccatgc tcgtcattac tacctttctg    720

catcacaatg acgaggaaac tccttggtac ggagattccg actggaccta cgtcaagggc    780

aacttgtctt ccgtggaccg atcttacggt gccttcatcg acaacctctc gcacaacatt    840

ggcacacacc agatccacca tctgtttccc atcattcctc actacaagct caaccgagcc    900

accgctgcct tccaccaggc ctttcccgaa cttgtccgaa agagcgacga gcccattctc    960

aaggctttct ggagagttgg tcgactttac gccaactacg gagtcgtgga tcccgacgca   1020

aagctgttta ctctcaagga ggccaaagct gcctccgagg ctgccaccaa gaccaaggct   1080

acttaa                                                              1086


<210> SEQ ID NO 8
<211> LENGTH: 1086
<212> TYPE: DNA
<213> ORGANISM: Phytophthora infestans (GenBank Accession No. CAJ30870)

<400> SEQUENCE: 8

atggcgacga aggaggcgta tgtgttcccc actctgacgg agatcaagcg gtcgctacct     60

aaagactgtt tcgaggcttc ggtgcctctg tcgctctact acaccgtgcg ttgtctggtg    120
```

```
atcgcggtgg ctctaacctt cggtctcaac tacgctcgcg ctctgcccga ggtcgagagc    180

ttctgggctc tggacgccgc actctgcacg ggctacatct tgctgcaggg catcgtgttc    240

tggggcttct tcacggtggg ccacgatgcc ggccacggcg ccttctcgcg ctaccacctg    300

cttaacttcg tggtgggcac tttcatgcac tcgctcatcc tcacgccctt cgagtcgtgg    360

aagctcacgc accgtcacca ccacaagaac acgggcaaca ttgaccgtga cgaggtcttc    420

tacccgcaac gcaaggccga cgaccacccg ctgtctcgca acctgattct ggcgctcggg    480

gcagcgtggc tcgcctattt ggtcgagggc ttccctcctc gtaaggtcaa ccacttcaac    540

ccgttcgagc ctctgttcgt gcgtcaggtg tcagctgtgg taatctctct tctcgcccac    600

ttcttcgtgg ccggactctc catctatctg agcctccagc tgggccttaa gacgatggca    660

atctactact atggacctgt ttttgtgttc ggcagcatgc tggtcattac caccttccta    720

caccacaatg atgaggagac cccatggtac gccgactcgg agtggacgta cgtcaagggc    780

aacctctcgt ccgtggaccg atcgtacggc gcgctcattg acaacctgag ccacaacatc    840

ggcacgcacc agatccacca ccttttccct atcattccgc actacaaact caagaaagcc    900

actgcggcct tccaccaggc tttccctgag ctcgtgcgca agagcgacga gccaattatc    960

aaggctttct tccgggttgg acgtctctac gcaaactacg gcgttgtgga ccaggaggcg   1020

aagctcttca cgctaaagga agccaaggcg gcgaccgagg cggcggccaa gaccaagtcc   1080

acgtaa                                                              1086
```

```
<210> SEQ ID NO 9
<211> LENGTH: 361
<212> TYPE: PRT
<213> ORGANISM: Phytophthora infestans
<300> PUBLICATION INFORMATION:
<302> TITLE: METHOD FOR PRODUCING UNSATURATED Omega3 FATTY ACIDS IN
      TRANSGENIC
<308> DATABASE ACCESSION NUMBER: CAJ30870
<309> DATABASE ENTRY DATE: 2005-09-21
<310> PATENT DOCUMENT NUMBER: WO 2005083053
<311> PATENT FILING DATE: 2005-02-23
<312> PUBLICATION DATE: 2005-09-09
<313> RELEVANT RESIDUES: (1)..(361)

<400> SEQUENCE: 9

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140
```

-continued

```
Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360
```

<210> SEQ ID NO 10
<211> LENGTH: 3806
<212> TYPE: DNA
<213> ORGANISM: Artificial Sequence
<220> FEATURE:
<223> OTHER INFORMATION: Plasmid pPsD17S

<400> SEQUENCE: 10

```
atcggatccc gggcccgtcg actgcagagg cctgcatgca agcttggcgt aatcatggtc     60

atagctgttt cctgtgtgaa attgttatcc gctcacaatt ccacacaaca tacgagccgg    120

aagcataaag tgtaaagcct ggggtgccta atgagtgagc taactcacat taattgcgtt    180

gcgctcactg cccgctttcc agtcgggaaa cctgtcgtgc cagctgcatt aatgaatcgg    240

ccaacgcgcg gggagaggcg gtttgcgtat tgggcgctct tccgcttcct cgctcactga    300

ctcgctgcgc tcggtcgttc ggctgcggcg agcggtatca gctcactcaa aggcggtaat    360

acggttatcc acagaatcag gggataacgc aggaaagaac atgtgagcaa aaggccagca    420

aaaggccagg aaccgtaaaa aggccgcgtt gctggcgttt ttccataggc tccgcccccc    480

tgacgagcat cacaaaaatc gacgctcaag tcagaggtgg cgaaacccga caggactata    540

aagataccag gcgtttcccc ctggaagctc cctcgtgcgc tctcctgttc cgaccctgcc    600

gcttaccgga tacctgtccg cctttctccc ttcgggaagc gtggcgcttt ctcatagctc    660

acgctgtagg tatctcagtt cggtgtaggt cgttcgctcc aagctgggct gtgtgcacga    720

accccccgtt cagcccgacc gctgcgcctt atccggtaac tatcgtcttg agtccaaccc    780

ggtaagacac gacttatcgc cactggcagc agccactggt aacaggatta gcagagcgag    840
```

-continued

```
gtatgtaggc ggtgctacag agttcttgaa gtggtggcct aactacggct acactagaag    900
aacagtattt ggtatctgcg ctctgctgaa gccagttacc ttcggaaaaa gagttggtag    960
ctcttgatcc ggcaaacaaa ccaccgctgg tagcggtggt ttttttgttt gcaagcagca   1020
gattacgcgc agaaaaaaag gatctcaaga agatcctttg atcttttcta cggggtctga   1080
cgctcagtgg aacgaaaact cacgttaagg gattttggtc atgagattat caaaaaggat   1140
cttcacctag atccttttaa attaaaaatg aagttttaaa tcaatctaaa gtatatatga   1200
gtaaacttgg tctgacagtt accaatgctt aatcagtgag gcacctatct cagcgatctg   1260
tctatttcgt tcatccatag ttgcctgact ccccgtcgtg tagataacta cgatacggga   1320
gggcttacca tctggcccca gtgctgcaat gataccgcga gacccacgct caccggctcc   1380
agatttatca gcaataaacc agccagccgg aagggccgag cgcagaagtg gtcctgcaac   1440
tttatccgcc tccatccagt ctattaattg ttgccgggaa gctagagtaa gtagttcgcc   1500
agttaatagt ttgcgcaacg ttgttgccat tgctacaggc atcgtggtgt cacgctcgtc   1560
gtttggtatg gcttcattca gctccggttc ccaacgatca aggcgagtta catgatcccc   1620
catgttgtgc aaaaaagcgg ttagctcctt cggtcctccg atcgttgtca gaagtaagtt   1680
ggccgcagtg ttatcactca tggttatggc agcactgcat aattctctta ctgtcatgcc   1740
atccgtaaga tgcttttctg tgactggtga gtactcaacc aagtcattct gagaatagtg   1800
tatgcggcga ccgagttgct cttgcccggc gtcaatacgg gataataccg cgccacatag   1860
cagaacttta aaagtgctca tcattggaaa acgttcttcg gggcgaaaac tctcaaggat   1920
cttaccgctg ttgagatcca gttcgatgta acccactcgt gcacccaact gatcttcagc   1980
atcttttact ttcaccagcg tttctgggtg agcaaaaaca ggaaggcaaa atgccgcaaa   2040
aaagggaata agggcgacac ggaaatgttg aatactcata ctcttccttt ttcaatatta   2100
ttgaagcatt tatcagggtt attgtctcat gagcggatac atatttgaat gtatttagaa   2160
aaataaacaa ataggggttc cgcgcacatt tccccgaaaa gtgccacctg acgtctaaga   2220
aaccattatt atcatgacat taacctataa aaataggcgt atcacgaggc cctttcgtct   2280
cgcgcgtttc ggtgatgacg gtgaaaacct ctgacacatg cagctcccgg agacggtcac   2340
agcttgtctg taagcggatg ccgggagcag acaagcccgt cagggcgcgt cagcgggtgt   2400
tggcgggtgt cggggctggc ttaactatgc ggcatcagag cagattgtac tgagagtgca   2460
ccatatgcgg tgtgaaatac cgcacagatg cgtaaggaga aaataccgca tcaggcgcca   2520
ttcgccattc aggctgcgca actgttggga agggcgatcg gtgcgggcct cttcgctatt   2580
acgccagctg gcgaaagggg gatgtgctgc aaggcgatta agttgggtaa cgccagggtt   2640
ttcccagtca cgacgttgta aaacgacggc cagtgaattc gagctcggta cctcgcgaat   2700
gcatctagat ccatggctac caagcagccc taccagttcc ctactctgac cgagatcaag   2760
cgatctctgc cctccgagtg tttcgaggcc tccgtgcctc tctctctgta ctacaccgtt   2820
cgatgcctgg tcattgctgt gtcgctcgcc ttcggacttc accatgcacg atctctgccc   2880
gttgtcgaag gcctctgggc tctggatgcc gctctctgca ccggttacgt gctgctccag   2940
ggcatcgtct tctggggatt ctttactgtt ggtcacgacg ctggacatgg tgccttctcc   3000
cgataccacc tgctcaactt tgtcatcgga accttcattc actctctcat ccttacaccc   3060
ttcgagtcct ggaagctcac ccacagacac catcacaaga acactggcaa catcgaccga   3120
gacgaaatct tctaccctca acgaaaggcc gacgatcatc ctctgtctcg aaacctcatt   3180
```

-continued

```
ctggctttgg gtgcagcctg gtttgcctac ctggtcgaag gctttcctcc ccgaaaggtc   3240

aaccacttca accccttcga gcctctcttt gttcgacagg tctctgccgt ggtcatttcg   3300

ctggctgcgc actttggagt ggctgccctg tccatctacc tcagcctgca gttcggcttc   3360

aagactatgg ccatctacta ctatggtccc gtctttgtgt tcggatccat gctcgtcatt   3420

actacctttc ttcatcacaa cgacgaagag acaccttggt acgcagattc ggagtggacc   3480

tacgtcaaag gcaacctgtc ctctgtcgac cgatcctacg gtgccctcat cgacaacctt   3540

tctcacaaca tcggaaccca ccagattcat cacctctttc ccatcattcc tcactacaag   3600

ctcaagcgag ctaccgaggc cttccatcaa gcctttcccg agctggttcg aaagtccgac   3660

gaacccatca tcaaggcctt tttcagagtc ggccgactct acgcaaacta cggtgtggtc   3720

gactcggatg ccaagctgtt cactctcaag gaggccaagg ctgtttccga agccgctacc   3780

aagactaagg ccacctaagc ggccgc                                         3806
```

```
<210> SEQ ID NO 11
<211> LENGTH: 6619
<212> TYPE: DNA
<213> ORGANISM: Artificial Sequence
<220> FEATURE:
<223> OTHER INFORMATION: Plasmid pKunF1-KEA

<400> SEQUENCE: 11
```

```
tttgaatcga atcgatgagc ctaaaatgaa cccgagtata tctcataaaa ttctcggtga     60

gaggtctgtg actgtcagta caaggtgcct tcattatgcc ctcaacctta ccatacctca    120

ctgaatgtag tgtacctcta aaaatgaaat acagtgccaa aagccaaggc actgagctcg    180

tctaacggac ttgatataca accaattaaa acaaatgaaa agaaatacag ttctttgtat    240

catttgtaac aattaccctg tacaaactaa ggtattgaaa tcccacaata ttcccaaagt    300

ccacccccttt ccaaattgtc atgcctacaa ctcatatacc aagcactaac ctaccgttta   360

aacagtgtac gcagatctac tatagaggaa catttaaatt gccccggaga agacggccag    420

gccgcctaga tgacaaattc aacaactcac agctgacttt ctgccattgc cactaggggg    480

gggcctttttt atatggccaa gccaagctct ccacgtcggt tgggctgcac ccaacaataa   540

atgggtaggg ttgcaccaac aaagggatgg gatgggggt agaagatacg aggataacgg     600

ggctcaatgg cacaaataag aacgaatact gccattaaga ctcgtgatcc agcgactgac    660

accattgcat catctaaggg cctcaaaact acctcggaac tgctgcgctg atctggacac    720

cacagaggtt ccgagcactt taggttgcac caaatgtccc accaggtgca ggcagaaaac    780

gctggaacag cgtgtacagt ttgtcttaac aaaaagtgag ggcgctgagg tcgagcaggg    840

tggtgtgact tgttatagcc tttagagctg cgaaagcgcg tatggatttg gctcatcagg    900

ccagattgag ggtctgtgga cacatgtcat gttagtgtac ttcaatcgcc ccctggatat    960

agccccgaca ataggccgtg gcctcatttt tttgccttcc gcacatttcc attgctcggt   1020

acccacacct tgcttctcct gcacttgcca accttaatac tggtttacat tgaccaacat   1080

cttacaagcg gggggcttgt ctagggtata tataaacagt ggctctccca atcggttgcc   1140

agtctctttt ttcctttctt tccccacaga ttcgaaatct aaactacaca tcacagaatt   1200

ccgagccgtg agtatccacg acaagatcag tgtcgagacg acgcgttttg tgtaatgaca   1260

caatccgaaa gtcgctagca acacacactc tctacacaaa ctaacccagc tctggtacca   1320

tggagtccat tgctcccttc ctgccctcca agatgcctca ggacctgttc atggacctcg   1380

ccagcgctat cggtgtccga gctgctccct acgtcgatcc cctggaggct gccctggttg   1440
```

-continued

```
cccaggccga gaagtacatt cccaccattg tccatcacac tcgaggcttc ctggttgccg   1500
tggagtctcc cctggctcga gagctgcctc tgatgaaccc cttccacgtg ctcctgatcg   1560
tgctcgccta cctggtcacc gtgtttgtgg gtatgcagat catgaagaac tttgaacgat   1620
tcgaggtcaa gaccttctcc ctcctgcaca acttctgtct ggtctccatc tccgcctaca   1680
tgtgcggtgg catcctgtac gaggcttatc aggccaacta tggactgttt gagaacgctg   1740
ccgatcacac cttcaagggt ctccctatgg ctaagatgat ctggctcttc tacttctcca   1800
agatcatgga gtttgtcgac accatgatca tggtcctcaa gaagaacaac cgacagattt   1860
cctttctgca cgtgtaccac cactcttcca tcttcaccat ctggtggctg gtcaccttcg   1920
ttgctcccaa cggtgaagcc tacttctctg ctgccctgaa ctccttcatc cacgtcatca   1980
tgtacggcta ctactttctg tctgccctgg gcttcaagca ggtgtcgttc atcaagttct   2040
acatcactcg atcccagatg acccagttct gcatgatgtc tgtccagtct tcctgggaca   2100
tgtacgccat gaaggtcctt ggccgacctg gatacccctt cttcatcacc gctctgctct   2160
ggttctacat gtggaccatg ctcggtctct tctacaactt ttaccgaaag aacgccaagc   2220
tcgccaagca ggccaaggct gacgctgcca aggagaaggc cagaaagctc cagtaagcgg   2280
ccgcaagtgt ggatggggaa gtgagtgccc ggttctgtgt gcacaattgg caatccaaga   2340
tggatggatt caacacaggg atatagcgag ctacgtggtg gtgcgaggat atagcaacgg   2400
atatttatgt ttgacacttg agaatgtacg atacaagcac tgtccaagta caatactaaa   2460
catactgtac atactcatac tcgtacccgg gcaacggttt cacttgagtg cagtggctag   2520
tgctcttact cgtacagtgt gcaatactgc gtatcatagt ctttgatgta tatcgtattc   2580
attcatgtta gttgcgtacg aagtcgtcaa tgatgtcgat atgggttttg atcatgcaca   2640
cataaggtcc gaccttatcg gcaagctcaa tgagctcctt ggtggtggta acatccagag   2700
aagcacacag gttggttttc ttggctgcca cgagcttgag cactcgagcg gcaaaggcgg   2760
acttgtggac gttagctcga gcttcgtagg agggcatttt ggtggtgaag aggagactga   2820
aataaattta gtctgcagaa ctttttatcg gaaccttatc tggggcagtg aagtatatgt   2880
tatggtaata gttacgagtt agttgaactt atagatagac tggactatac ggctatcggt   2940
ccaaattaga aagaacgtca atggctctct gggcgtcgcc tttgccgaca aaaatgtgat   3000
catgatgaaa gccagcaatg acgttgcagc tgatattgtt gtcggccaac cgcgccgaaa   3060
acgcagctgt cagacccaca gcctccaacg aagaatgtat cgtcaaagtg atccaagcac   3120
actcatagtt ggagtcgtac tccaaaggcg gcaatgacga gtcagacaga tactcgtcga   3180
ccttttcctt gggaaccacc accgtcagcc cttctgactc acgtattgta gccaccgaca   3240
caggcaacag tccgtggata gcagaatatg tcttgtcggt ccatttctca ccaactttag   3300
gcgtcaagtg aatgttgcag aagaagtatg tgccttcatt gagaatcggt gttgctgatt   3360
tcaataaagt cttgagatca gtttggcgcg ccagctgcat taatgaatcg gccaacgcgc   3420
ggggagaggc ggtttgcgta ttgggcgctc ttccgcttcc tcgctcactg actcgctgcg   3480
ctcggtcgtt cggctgcggc gagcggtatc agctcactca aaggcggtaa tacggttatc   3540
cacagaatca ggggataacg caggaaagaa catgtgagca aaaggccagc aaaaggccag   3600
gaaccgtaaa aaggccgcgt tgctggcgtt tttccatagg ctccgccccc ctgacgagca   3660
tcacaaaaat cgacgctcaa gtcagaggtg gcgaaacccg acaggactat aaagatacca   3720
ggcgtttccc cctggaagct ccctcgtgcg ctctcctgtt ccgaccctgc cgcttaccgg   3780
```

-continued

```
atacctgtcc gcctttctcc cttcgggaag cgtggcgctt tctcatagct cacgctgtag   3840
gtatctcagt tcggtgtagg tcgttcgctc caagctgggc tgtgtgcacg aaccccccgt   3900
tcagcccgac cgctgcgcct tatccggtaa ctatcgtctt gagtccaacc cggtaagaca   3960
cgacttatcg ccactggcag cagccactgg taacaggatt agcagagcga ggtatgtagg   4020
cggtgctaca gagttcttga agtggtggcc taactacggc tacactagaa gaacagtatt   4080
tggtatctgc gctctgctga agccagttac cttcggaaaa agagttggta gctcttgatc   4140
cggcaaacaa accaccgctg gtagcggtgg tttttttgtt tgcaagcagc agattacgcg   4200
cagaaaaaaa ggatctcaag aagatccttt gatcttttct acggggtctg acgctcagtg   4260
gaacgaaaac tcacgttaag ggattttggt catgagatta tcaaaaagga tcttcaccta   4320
gatcctttta aattaaaaat gaagttttaa atcaatctaa agtatatatg agtaaacttg   4380
gtctgacagt taccaatgct taatcagtga ggcacctatc tcagcgatct gtctatttcg   4440
ttcatccata gttgcctgac tccccgtcgt gtagataact acgatacggg agggcttacc   4500
atctggcccc agtgctgcaa tgataccgcg agacccacgc tcaccggctc cagatttatc   4560
agcaataaac cagccagccg gaagggccga gcgcagaagt ggtcctgcaa ctttatccgc   4620
ctccatccag tctattaatt gttgccggga agctagagta agtagttcgc cagttaatag   4680
tttgcgcaac gttgttgcca ttgctacagg catcgtggtg tcacgctcgt cgtttggtat   4740
ggcttcattc agctccggtt cccaacgatc aaggcgagtt acatgatccc ccatgttgtg   4800
caaaaaagcg gttagctcct tcggtcctcc gatcgttgtc agaagtaagt tggccgcagt   4860
gttatcactc atggttatgg cagcactgca taattctctt actgtcatgc catccgtaag   4920
atgcttttct gtgactggtg agtactcaac caagtcattc tgagaatagt gtatgcggcg   4980
accgagttgc tcttgcccgg cgtcaatacg ggataatacc gcgccacata gcagaacttt   5040
aaaagtgctc atcattggaa aacgttcttc ggggcgaaaa ctctcaagga tcttaccgct   5100
gttgagatcc agttcgatgt aacccactcg tgcacccaac tgatcttcag catcttttac   5160
tttcaccagc gtttctgggt gagcaaaaac aggaaggcaa aatgccgcaa aaaagggaat   5220
aagggcgaca cggaaatgtt gaatactcat actcttcctt tttcaatatt attgaagcat   5280
ttatcagggt tattgtctca tgagcggata catatttgaa tgtatttaga aaaataaaca   5340
aataggggtt ccgcgcacat ttccccgaaa agtgccacct gatgcggtgt gaaataccgc   5400
acagatgcgt aaggagaaaa taccgcatca ggaaattgta agcgttaata ttttgttaaa   5460
attcgcgtta aatttttgtt aaatcagctc attttttaac caataggccg aaatcggcaa   5520
aatcccttat aaatcaaaag aatagaccga gatagggttg agtgttgttc cagtttggaa   5580
caagagtcca ctattaaaga acgtggactc caacgtcaaa gggcgaaaaa ccgtctatca   5640
gggcgatggc ccactacgtg aaccatcacc ctaatcaagt tttttggggt cgaggtgccg   5700
taaagcacta aatcggaacc ctaaagggag cccccgattt agagcttgac ggggaaagcc   5760
ggcgaacgtg gcgagaaagg aagggaagaa agcgaaagga gcgggcgcta gggcgctggc   5820
aagtgtagcg gtcacgctgc gcgtaaccac cacacccgcc gcgcttaatg cgccgctaca   5880
gggcgcgtcc attcgccatt caggctgcgc aactgttggg aagggcgatc ggtgcgggcc   5940
tcttcgctat tacgccagct ggcgaaaggg ggatgtgctg caaggcgatt aagttgggta   6000
acgccagggt tttcccagtc acgacgttgt aaaacgacgg ccagtgaatt gtaatacgac   6060
tcactatagg gcgaattggg cccgacgtcg catgcagtgg tggtattgtg actggggatg   6120
tagttgagaa taagtcatac acaagtcagc tttcttcgag cctcatataa gtataagtag   6180
```

ttcaacgtat tagcactgta cccagcatct ccgtatcgag aaacacaaca acatgcccca 6240
ttggacagat catgcggata cacaggttgt gcagtatcat acatactcga tcagacaggt 6300
cgtctgacca tcatacaagc tgaacaagcg ctccatactt gcacgctctc tatatacaca 6360
gttaaattac atatccatag tctaacctct aacagttaat cttctggtaa gcctcccagc 6420
cagccttctg gtatcgcttg gcctcctcaa taggatctcg gttctggccg tacagacctc 6480
ggccgacaat tatgatatcc gttccggtag acatgacatc ctcaacagtt cggtactgct 6540
gtccgagagc gtctcccttg tcgtcaagac ccaccccggg ggtcagaata agccagtcct 6600
cagagtcgcc cttaattaa 6619

<210> SEQ ID NO 12
<211> LENGTH: 9513
<212> TYPE: DNA
<213> ORGANISM: Artificial Sequence
<220> FEATURE:
<223> OTHER INFORMATION: Plasmid pDMW214

<400> SEQUENCE: 12
ggtggagctc cagcttttgt tccctttagt gagggttaat ttcgagcttg gcgtaatcat 60
ggtcatagct gtttcctgtg tgaaattgtt atccgctcac aattccacac aacatacgag 120
ccggaagcat aaagtgtaaa gcctggggtg cctaatgagt gagctaactc acattaattg 180
cgttgcgctc actgcccgct ttccagtcgg gaaacctgtc gtgccagctg cattaatgaa 240
tcggccaacg cgcggggaga ggcggtttgc gtattgggcg ctcttccgct tcctcgctca 300
ctgactcgct gcgctcggtc gttcggctgc ggcgagcggt atcagctcac tcaaaggcgg 360
taatacggtt atccacagaa tcaggggata acgcaggaaa gaacatgtga gcaaaaggcc 420
agcaaaaggc caggaaccgt aaaaaggccg cgttgctggc gtttttccat aggctccgcc 480
cccctgacga gcatcacaaa aatcgacgct caagtcagag gtggcgaaac ccgacaggac 540
tataaagata ccaggcgttt ccccctggaa gctccctcgt gcgctctcct gttccgaccc 600
tgccgcttac cggatacctg tccgcctttc tcccttcggg aagcgtggcg ctttctcata 660
gctcacgctg taggtatctc agttcggtgt aggtcgttcg ctccaagctg ggctgtgtgc 720
acgaaccccc cgttcagccc gaccgctgcg ccttatccgg taactatcgt cttgagtcca 780
acccggtaag acacgactta tcgccactgg cagcagccac tggtaacagg attagcagag 840
cgaggtatgt aggcggtgct acagagttct tgaagtggtg gcctaactac ggctacacta 900
gaaggacagt atttggtatc tgcgctctgc tgaagccagt taccttcgga aaaagagttg 960
gtagctcttg atccggcaaa caaaccaccg ctggtagcgg tggttttttt gtttgcaagc 1020
agcagattac gcgcagaaaa aaaggatctc aagaagatcc tttgatcttt tctacggggt 1080
ctgacgctca gtggaacgaa aactcacgtt aagggatttt ggtcatgaga ttatcaaaaa 1140
ggatcttcac ctagatcctt ttaaattaaa aatgaagttt taaatcaatc taaagtatat 1200
atgagtaaac ttggtctgac agttaccaat gcttaatcag tgaggcacct atctcagcga 1260
tctgtctatt tcgttcatcc atagttgcct gactccccgt cgtgtagata actacgatac 1320
gggagggctt accatctggc cccagtgctg caatgatacc gcgagaccca cgctcaccgg 1380
ctccagattt atcagcaata aaccagccag ccggaagggc cgagcgcaga agtggtcctg 1440
caactttatc cgcctccatc cagtctatta attgttgccg ggaagctaga gtaagtagtt 1500
cgccagttaa tagtttgcgc aacgttgttg ccattgctac aggcatcgtg gtgtcacgct 1560

-continued

```
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
```

-continued

```
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt ttttttttct aatgattcat   4140
taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg gggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg gggaattcg tccttgagga ctcgagtgac agtctttcgc   5580
caaagtcgag aggaggccag cacgttggcc ttgtcaagag accacacggg aagaggggg   5640
ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
```

-continued

```
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aataaatgat gtcgacgttt aaacagtgta cgcagtacta tagaggaaca attgccccgg   6540
agaagacggc caggccgcct agatgacaaa ttcaacaact cacagctgac tttctgccat   6600
tgccactagg ggggggcctt tttatatggc caagccaagc tctccacgtc ggttgggctg   6660
cacccaacaa taaatgggta gggttgcacc aacaaaggga tgggatgggg ggtagaagat   6720
acgaggataa cggggctcaa tggcacaaat aagaacgaat actgccatta agactcgtga   6780
tccagcgact gacaccattg catcatctaa gggcctcaaa actacctcgg aactgctgcg   6840
ctgatctgga caccacagag gttccgagca ctttaggttg caccaaatgt cccaccaggt   6900
gcaggcagaa aacgctggaa cagcgtgtac agtttgtctt aacaaaaagt gagggcgctg   6960
aggtcgagca gggtggtgtg acttgttata gcctttagag ctgcgaaagc gcgtatggat   7020
ttggctcatc aggccagatt gagggtctgt ggacacatgt catgttagtg tacttcaatc   7080
gccccctgga tatagccccg acaataggcc gtggcctcat ttttttgcct tccgcacatt   7140
tccattgctc ggtacccaca ccttgcttct cctgcacttg ccaaccttaa tactggttta   7200
cattgaccaa catcttacaa gcgggggggct tgtctagggt atatataaac agtggctctc   7260
ccaatcggtt gccagtctct tttttccttt ctttccccac agattcgaaa tctaaactac   7320
acatcacaca atgcctgtta ctgacgtcct taagcgaaag tccggtgtca tcgtcggcga   7380
cgatgtccga gccgtgagta tccacgacaa gatcagtgtc gagacgacgc gttttgtgta   7440
atgacacaat ccgaaagtcg ctagcaacac acactctcta cacaaactaa cccagctctc   7500
catggcatgg atggtacgtc ctgtagaaac cccaacccgt gaaatcaaaa aactcgacgg   7560
cctgtgggca ttcagtctgg atcgcgaaaa ctgtggaatt gatcagcgtt ggtgggaaag   7620
cgcgttacaa gaaagccggg caattgctgt gccaggcagt tttaacgatc agttcgccga   7680
tgcagatatt cgtaattatg cgggcaacgt ctggtatcag cgcgaagtct ttataccgaa   7740
aggttgggca ggccagcgta tcgtgctgcg tttcgatgcg gtcactcatt acggcaaagt   7800
gtgggtcaat aatcaggaag tgatggagca tcagggcggc tatacgccat ttgaagccga   7860
tgtcacgccg tatgttattg ccgggaaaag tgtacgtatc accgtttgtg tgaacaacga   7920
actgaactgg cagactatcc cgccgggaat ggtgattacc gacgaaaacg gcaagaaaaa   7980
gcagtcttac ttccatgatt tctttaacta tgccgggatc catcgcagcg taatgctcta   8040
caccacgccg aacacctggg tggacgatat caccgtggtg acgcatgtcg cgcaagactg   8100
taaccacgcg tctgttgact ggcaggtggt ggccaatggt gatgtcagcg ttgaactgcg   8160
tgatgcggat caacaggtgg ttgcaactgg acaaggcact agcgggactt tgcaagtggt   8220
gaatccgcac ctctggcaac cgggtgaagg ttatctctat gaactgtgcg tcacagccaa   8280
aagccagaca gagtgtgata tctacccgct tcgcgtcggc atccggtcag tggcagtgaa   8340
gggcgaacag ttcctgatta accacaaacc gttctacttt actggctttg gtcgtcatga   8400
agatgcggac ttacgtggca aaggattcga taacgtgctg atggtgcacg accacgcatt   8460
aatggactgg attggggcca actcctaccg tacctcgcat tacccttacg ctgaagagat   8520
gctcgactgg gcagatgaac atggcatcgt ggtgattgat gaaactgctg ctgtcggctt   8580
taacctctct ttaggcattg gtttcgaagc gggcaacaag ccgaaagaac tgtacagcga   8640
agaggcagtc aacggggaaa ctcagcaagc gcacttacag gcgattaaag agctgatagc   8700
```

-continued gcgtgacaaa aaccacccaa gcgtggtgat gtggagtatt gccaacgaac cggatacccg 8760
tccgcaagtg cacgggaata tttcgccact ggcggaagca acgcgtaaac tcgacccgac 8820
gcgtccgatc acctgcgtca atgtaatgtt ctgcgacgct cacaccgata ccatcagcga 8880
tctctttgat gtgctgtgcc tgaaccgtta ttacggatgg tatgtccaaa gcggcgattt 8940
ggaaacggca gagaaggtac tggaaaaaga acttctggcc tggcaggaga aactgcatca 9000
gccgattatc atcaccgaat acggcgtgga tacgttagcc gggctgcact caatgtacac 9060
cgacatgtgg agtgaagagt atcagtgtgc atggctggat atgtatcacc gcgtctttga 9120
tcgcgtcagc gccgtcgtcg gtgaacaggt atggaatttc gccgattttg cgacctcgca 9180
aggcatattg cgcgttggcg gtaacaagaa agggatcttc actcgcgacc gcaaaccgaa 9240
gtcggcggct tttctgctgc aaaaacgctg gactggcatg aacttcggtg aaaaaccgca 9300
gcagggaggc aaacaatgat taattaacta gagcggccgc caccgcggcc cgagattccg 9360
gcctcttcgg ccgccaagcg acccgggtgg acgtctagag gtacctagca attaacagat 9420
agtttgccgg tgataattct cttaacctcc cacactcctt tgacataacg atttatgtaa 9480
cgaaactgaa atttgaccag atattgtgtc cgc 9513

<210> SEQ ID NO 13
<211> LENGTH: 8727
<212> TYPE: DNA
<213> ORGANISM: Artificial Sequence
<220> FEATURE:
<223> OTHER INFORMATION: Plasmid pFmPsD17S

<400> SEQUENCE: 13
catggctacc aagcagccct accagttccc tactctgacc gagatcaagc gatctctgcc 60
ctccgagtgt ttcgaggcct ccgtgcctct ctctctgtac tacaccgttc gatgcctggt 120
cattgctgtg tcgctcgcct tcggacttca ccatgcacga tctctgcccg ttgtcgaagg 180
cctctgggct ctggatgccg ctctctgcac cggttacgtg ctgctccagg gcatcgtctt 240
ctggggattc tttactgttg gtcacgacgc tggacatggt gccttctccc gataccacct 300
gctcaacttt gtcatcggaa ccttcattca ctctctcatc cttacaccct tcgagtcctg 360
gaagctcacc cacagacacc atcacaagaa cactggcaac atcgaccgag acgaaatctt 420
ctaccctcaa cgaaaggccg acgatcatcc tctgtctcga aacctcattc tggctttggg 480
tgcagcctgg tttgcctacc tggtcgaagg ctttcctccc cgaaaggtca accacttcaa 540
ccccttcgag cctctctttg ttcgacaggt ctctgccgtg gtcatttcgc tggctgcgca 600
ctttggagtg gctgccctgt ccatctacct cagcctgcag ttcggcttca agactatggc 660
catctactac tatggtcccg tctttgtgtt cggatccatg ctcgtcatta ctacctttct 720
tcatcacaac gacgaagaga caccttggta cgcagattcg gagtggacct acgtcaaagg 780
caacctgtcc tctgtcgacc gatcctacgg tgccctcatc gacaaccttt ctcacaacat 840
cggaacccac cagattcatc acctctttcc catcattcct cactacaagc tcaagcgagc 900
taccgaggcc ttccatcaag cctttcccga gctggttcga aagtccgacg aacccatcat 960
caaggccttt ttcagagtcg gccgactcta cgcaaactac ggtgtggtcg actcggatgc 1020
caagctgttc actctcaagg aggccaaggc tgtttccgaa gccgctacca agactaaggc 1080
cacctaagcg gccgccaccg cggcccgaga ttccggcctc ttcggccgcc aagcgacccg 1140
ggtggacgtc tagaggtacc tagcaattaa cagatagttt gccggtgata attctcttaa 1200

-continued

```
cctcccacac tcctttgaca taacgattta tgtaacgaaa ctgaaatttg accagatatt   1260
gtgtccgcgg tggagctcca gcttttgttc cctttagtga gggttaattt cgagcttggc   1320
gtaatcatgg tcatagctgt ttcctgtgtg aaattgttat ccgctcacaa ttccacacaa   1380
catacgagcc ggaagcataa agtgtaaagc ctggggtgcc taatgagtga gctaactcac   1440
attaattgcg ttgcgctcac tgcccgcttt ccagtcggga aacctgtcgt gccagctgca   1500
ttaatgaatc ggccaacgcg cggggagagg cggtttgcgt attgggcgct cttccgcttc   1560
ctcgctcact gactcgctgc gctcggtcgt tcggctgcgg cgagcggtat cagctcactc   1620
aaaggcggta atacggttat ccacagaatc aggggataac gcaggaaaga acatgtgagc   1680
aaaaggccag caaaaggcca ggaaccgtaa aaaggccgcg ttgctggcgt ttttccatag   1740
gctccgcccc cctgacgagc atcacaaaaa tcgacgctca agtcagaggt ggcgaaaccc   1800
gacaggacta taaagatacc aggcgtttcc ccctggaagc tccctcgtgc gctctcctgt   1860
tccgaccctg ccgcttaccg gatacctgtc cgcctttctc ccttcgggaa gcgtggcgct   1920
ttctcatagc tcacgctgta ggtatctcag ttcggtgtag gtcgttcgct ccaagctggg   1980
ctgtgtgcac gaaccccccg ttcagcccga ccgctgcgcc ttatccggta actatcgtct   2040
tgagtccaac ccggtaagac acgacttatc gccactggca gcagccactg gtaacaggat   2100
tagcagagcg aggtatgtag gcggtgctac agagttcttg aagtggtggc ctaactacgg   2160
ctacactaga aggacagtat ttggtatctg cgctctgctg aagccagtta ccttcggaaa   2220
aagagttggt agctcttgat ccggcaaaca aaccaccgct ggtagcggtg gtttttttgt   2280
ttgcaagcag cagattacgc gcagaaaaaa aggatctcaa gaagatcctt tgatcttttc   2340
tacggggtct gacgctcagt ggaacgaaaa ctcacgttaa gggattttgg tcatgagatt   2400
atcaaaaagg atcttcacct agatcctttt aaattaaaaa tgaagtttta aatcaatcta   2460
aagtatatat gagtaaactt ggtctgacag ttaccaatgc ttaatcagtg aggcacctat   2520
ctcagcgatc tgtctatttc gttcatccat agttgcctga ctccccgtcg tgtagataac   2580
tacgatacgg gagggcttac catctggccc cagtgctgca atgataccgc gagacccacg   2640
ctcaccggct ccagatttat cagcaataaa ccagccagcc ggaagggccg agcgcagaag   2700
tggtcctgca actttatccg cctccatcca gtctattaat tgttgccggg aagctagagt   2760
aagtagttcg ccagttaata gtttgcgcaa cgttgttgcc attgctacag gcatcgtggt   2820
gtcacgctcg tcgtttggta tggcttcatt cagctccggt tcccaacgat caaggcgagt   2880
tacatgatcc cccatgttgt gcaaaaaagc ggttagctcc ttcggtcctc cgatcgttgt   2940
cagaagtaag ttggccgcag tgttatcact catggttatg gcagcactgc ataattctct   3000
tactgtcatg ccatccgtaa gatgcttttc tgtgactggt gagtactcaa ccaagtcatt   3060
ctgagaatag tgtatgcggc gaccgagttg ctcttgcccg gcgtcaatac gggataatac   3120
cgcgccacat agcagaactt taaaagtgct catcattgga aaacgttctt cggggcgaaa   3180
actctcaagg atcttaccgc tgttgagatc cagttcgatg taacccactc gtgcacccaa   3240
ctgatcttca gcatctttta ctttcaccag cgtttctggg tgagcaaaaa caggaaggca   3300
aaatgccgca aaaaagggaa taagggcgac acggaaatgt tgaatactca tactcttcct   3360
ttttcaatat tattgaagca tttatcaggg ttattgtctc atgagcggat acatatttga   3420
atgtatttag aaaaataaac aaataggggt tccgcgcaca tttccccgaa aagtgccacc   3480
tgacgcgccc tgtagcggcg cattaagcgc ggcgggtgtg gtggttacgc gcagcgtgac   3540
cgctacactt gccagcgccc tagcgcccgc tcctttcgct ttcttccctt cctttctcgc   3600
```

-continued

```
cacgttcgcc ggctttcccc gtcaagctct aaatcggggg ctccctttag ggttccgatt   3660
tagtgcttta cggcacctcg accccaaaaa acttgattag ggtgatggtt cacgtagtgg   3720
gccatcgccc tgatagacgg tttttcgccc tttgacgttg gagtccacgt tctttaatag   3780
tggactcttg ttccaaactg gaacaacact caaccctatc tcggtctatt cttttgattt   3840
ataagggatt ttgccgattt cggcctattg gttaaaaaat gagctgattt aacaaaaatt   3900
taacgcgaat tttaacaaaa tattaacgct tacaatttcc attcgccatt caggctgcgc   3960
aactgttggg aagggcgatc ggtgcgggcc tcttcgctat tacgccagct ggcgaaaggg   4020
ggatgtgctg caaggcgatt aagttgggta acgccagggt tttcccagtc acgacgttgt   4080
aaaacgacgg ccagtgaatt gtaatacgac tcactatagg gcgaattggg taccgggccc   4140
cccctcgagg tcgatggtgt cgataagctt gatatcgaat tcatgtcaca caaaccgatc   4200
ttcgcctcaa ggaaacctaa ttctacatcc gagagactgc cgagatccag tctacactga   4260
ttaattttcg ggccaataat ttaaaaaaat cgtgttatat aatattatat gtattatata   4320
tatacatcat gatgatactg acagtcatgt cccattgcta aatagacaga ctccatctgc   4380
cgcctccaac tgatgttctc aatatttaag ggtcatctc gcattgttta ataataaaca   4440
gactccatct accgcctcca aatgatgttc tcaaaatata ttgtatgaac ttatttttat   4500
tacttagtat tattagacaa cttacttgct ttatgaaaaa cacttcctat ttaggaaaca   4560
atttataatg gcagttcgtt catttaacaa tttatgtaga ataaatgtta taaatgcgta   4620
tgggaaatct taaatatgga tagcataaat gatatctgca ttgcctaatt cgaaatcaac   4680
agcaacgaaa aaaatccctt gtacaacata aatagtcatc gagaaatatc aactatcaaa   4740
gaacagctat tcacacgtta ctattgagat tattattgga cgagaatcac acactcaact   4800
gtctttctct cttctagaaa tacaggtaca agtatgtact attctcattg ttcatacttc   4860
tagtcatttc atcccacata ttccttggat ttctctccaa tgaatgacat tctatcttgc   4920
aaattcaaca attataataa gatataccaa agtagcggta tagtggcaat caaaaagctt   4980
ctctggtgtg cttctcgtat ttatttttat tctaatgatc cattaaaggt atatatttat   5040
ttcttgttat ataatccttt tgtttattac atgggctgga tacataaagg tattttgatt   5100
taattttttg cttaaattca atcccccctc gttcagtgtc aactgtaatg gtaggaaatt   5160
accatacttt tgaagaagca aaaaaaatga aagaaaaaaa aaatcgtatt tccaggttag   5220
acgttccgca gaatctagaa tgcggtatgc ggtacattgt tcttcgaacg taaaagttgc   5280
gctccctgag atattgtaca tttttgcttt tacaagtaca agtacatcgt acaactatgt   5340
actactgttg atgcatccac aacagtttgt tttgtttttt tttgtttttt tttttctaa    5400
tgattcatta ccgctatgta tacctacttg tacttgtagt aagccgggtt attggcgttc   5460
aattaatcat agacttatga atctgcacgg tgtgcgctgc gagttacttt tagcttatgc   5520
atgctacttg ggtgtaatat tgggatctgt tcggaaatca acggatgctc aaccgatttc   5580
gacagtaata atttgaatcg aatcggagcc taaaatgaac ccgagtatat ctcataaaat   5640
tctcggtgag aggtctgtga ctgtcagtac aaggtgcctt cattatgccc tcaaccttac   5700
catacctcac tgaatgtagt gtacctctaa aaatgaaata cagtgccaaa agccaaggca   5760
ctgagctcgt ctaacggact tgatatacaa ccaattaaaa caaatgaaaa gaaatacagt   5820
tctttgtatc atttgtaaca attaccctgt acaaactaag gtattgaaat cccacaatat   5880
tcccaaagtc cacccctttc caaattgtca tgcctacaac tcatatacca agcactaacc   5940
```

-continued

```
taccaaacac cactaaaacc ccacaaaata tatcttaccg aatatacagt aacaagctac   6000
caccacactc gttgggtgca gtcgccagct taaagatatc tatccacatc agccacaact   6060
cccttccttt aataaaccga ctacaccctt ggctattgag gttatgagtg aatatactgt   6120
agacaagaca ctttcaagaa gactgtttcc aaaacgtacc actgtcctcc actacaaaca   6180
cacccaatct gcttcttcta gtcaaggttg ctacaccggt aaattataaa tcatcatttc   6240
attagcaggg cagggccctt tttatagagt cttatacact agcggaccct gccggtagac   6300
caacccgcag gcgcgtcagt ttgctccttc catcaatgcg tcgtagaaac gacttactcc   6360
ttcttgagca gctccttgac cttgttggca acaagtctcc gacctcggag gtggaggaag   6420
agcctccgat atcggcggta gtgataccag cctcgacgga ctccttgacg gcagcctcaa   6480
cagcgtcacc ggcgggcttc atgttaagag agaacttgag catcatggcg gcagacagaa   6540
tggtggcaat ggggttgacc ttctgcttgc cgagatcggg ggcagatccg tgacagggct   6600
cgtacagacc gaacgcctcg ttggtgtcgg gcagagaagc cagagaggcg gagggcagca   6660
gacccagaga accggggatg acggaggcct cgtcggagat gatatcgcca aacatgttgg   6720
tggtgatgat gataccattc atcttggagg gctgcttgat gaggatcatg gcggccgagt   6780
cgatcagctg gtggttgagc tcgagctggg ggaattcgtc cttgaggact cgagtgacag   6840
tctttcgcca aagtcgagag gaggccagca cgttggcctt gtcaagagac cacacgggaa   6900
gaggggggtt gtgctgaagg gccaggaagg cggccattcg ggcaattcgc tcaacctcag   6960
gaacggagta ggtctcggtg tcggaagcga cgccagatcc gtcatcctcc tttcgctctc   7020
caaagtagat acctccgacg agctctcgga caatgatgaa gtcggtgccc tcaacgtttc   7080
ggatgggggga gagatcggcg agcttgggcg acagcagctg gcagggtcgc aggttggcgt   7140
acaggttcag gtcctttcgc agcttgagga gaccctgctc gggtcgcacg tcggttcgtc   7200
cgtcgggagt ggtccatacg gtgttggcag cgcctccgac agcaccgagc ataatagagt   7260
cagcctttcg gcagatgtcg agagtagcgt cggtgatggg ctcgccctcc ttctcaatgg   7320
cagctcctcc aatgagtcgg tcctcaaaca caaactcggt gccggaggcc tcagcaacag   7380
acttgagcac cttgacggcc tcggcaatca cctcggggcc acagaagtcg ccgccgagaa   7440
gaacaatctt cttggagtca gtcttggtct tcttagtttc gggttccatt gtggatgtgt   7500
gtggttgtat gtgtgatgtg gtgtgtggag tgaaaatctg tggctggcaa acgctcttgt   7560
atatatacgc acttttgccc gtgctatgtg gaagactaaa cctccgaaga ttgtgactca   7620
ggtagtgcgg tatcggctag ggacccaaac cttgtcgatg ccgatagcgc tatcgaacgt   7680
accccagccg gccgggagta tgtcggaggg gacatacgag atcgtcaagg gtttgtggcc   7740
aactggtaaa taaatgatgt cgacgtttaa acagtgtacg cagatctact atagaggaac   7800
atttaaattg ccccggagaa gacggccagg ccgcctagat gacaaattca acaactcaca   7860
gctgactttc tgccattgcc actagggggg ggcctttta tatggccaag ccaagctctc   7920
cacgtcggtt gggctgcacc caacaataaa tgggtagggt tgcaccaaca aagggatggg   7980
atggggggta gaagatacga ggataacggg gctcaatggc acaaataaga acgaatactg   8040
ccattaagac tcgtgatcca gcgactgaca ccattgcatc atctaagggc ctcaaaacta   8100
cctcggaact gctgcgctga tctggacacc acagaggttc cgagcacttt aggttgcacc   8160
aaatgtccca ccaggtgcag gcagaaaacg ctggaacagc gtgtacagtt tgtcttaaca   8220
aaaagtgagg gcgctgaggt cgagcagggt ggtgtgactt gttatagcct ttagagctgc   8280
gaaagcgcgt atggatttgg ctcatcaggc cagattgagg gtctgtggac acatgtcatg   8340
```

-continued

```
ttagtgtact tcaatcgccc cctggatata gccccgacaa taggccgtgg cctcattttt   8400

ttgccttccg cacatttcca ttgctcggta cccacacctt gcttctcctg cacttgccaa   8460

ccttaatact ggtttacatt gaccaacatc ttacaagcgg ggggcttgtc tagggtatat   8520

ataaacagtg gctctcccaa tcggttgcca gtctcttttt tcctttcttt ccccacagat   8580

tcgaaatcta aactacacat cacagaattc cgagccgtga gtatccacga caagatcagt   8640

gtcgagacga cgcgttttgt gtaatgacac aatccgaaag tcgctagcaa cacacactct   8700

ctacacaaac taacccagct ctggtac                                       8727
```

<210> SEQ ID NO 14
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 14

```
taaccctcac taaagggaac aaaagctgga gctccaccgc ggacacaata tctggtcaaa     60

tttcagtttc gttacataaa tcgttatgtc aaaggagtgt gggaggttaa gagaattatc    120

accggcaaac tatctgttaa ttgctaggta cctctagacg tccacccggg tcgcttggcg    180

gccgaagagg ccggaatctc gggccgcggt ggcggccgct tagttggtct tggacttctt    240

gggcttcttc aggtaggact ggacaaagaa gttgccgaac agagcgagca gggtgatcat    300

gtacacgccg agcagctgga ccagagcctg agggtagtcg caggggaaga ggtagtcgta    360

cagggactgc accagcatag ccatgaactg ggtcatctgc agagtggtga tgtagggctt    420

gatgggcttg acgaagccga agccctgaga ggaaaagaag tagtaggcgt acatgacggt    480

gtggacgaag gagttgagga tgacggagaa gtaggcgtcg ccaccaggag cgtacttggc    540

aatagcccac cagatggcga agatggtggc atggtggtac acgtgcagga aggagacctg    600

gttgaacttc ttgcacagga tcatgatagc ggtgtccagg aactcgtagg ccttggagac    660

gtagaacacg tagacgattc gggacatgcc ctgagcgtgg gactcgttgc ccttctccat    720

gtcgttgccg aagaccttgt agccacccag gatagcctgt cggatggtct cgacgcacat    780

gtagagggac agtccgaaga ggaacaggtt gtggagcagc ttgatggtct tcagctcgaa    840

gggcttctcc atctgcttca tgatgggaat gccgaagagc agcatggcca tgtagccgac    900

ctcgaaggcg agcatggtgg agacgtccat catgggcaga ccgtcggtca gagcgtaggg    960

cttagctccg tccatccact ggtcgacacc ggtctcgact cgtccgacca cgtcgtccca   1020

gacagaggag ttggccatgg tgaatgattc ttatactcag aaggaaatgc ttaacgattt   1080

cgggtgtgag ttgacaagga gagagagaaa agaagaggaa aggtaattcg gggacggtgg   1140

tcttttatac ccttggctaa agtcccaacc acaaagcaaa aaaattttca gtagtctatt   1200

ttgcgtccgg catgggttac ccggatggcc agacaaagaa actagtacaa agtctgaaca   1260

agcgtagatt ccagactgca gtaccctacg cccttaacgg caagtgtggg aaccggggga   1320

ggtttgatat gtggggtgaa gggggctctc gccggggttg ggcccgctac tgggtcaatt   1380
```

-continued

```
tggggtcaat tggggcaatt ggggctgttt tttgggacac aaatacgccg ccaacccggt   1440
ctctcctgaa ttctgcatcg atcgaggaag aggacaagcg gctgcttctt aagtttgtga   1500
catcagtatc caaggcacca ttgcaaggat tcaaggcttt gaacccgtca tttgccattc   1560
gtaacgctgg tagacaggtt gatcggttcc ctacggcctc cacctgtgtc aatcttctca   1620
agctgcctga ctatcaggac attgatcaac ttcggaagaa acttttgtat gccattcgat   1680
cacatgctgg tttcgatttg tcttagagga acgcatatac agtaatcata gagaataaac   1740
gatattcatt tattaaagta gatagttgag gtagaagttg taaagagtga taaatagcgg   1800
ccgcgcctac ttaagcaacg ggcttgataa cagcgggggg ggtgcccacg ttgttgcggt   1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
taacaccacc gccgaggccg ttatgcttgc ccttgccgcg accctcacgc tggcgctcgt   2460
ggtagttgtg gccggtaaca ttggtgatga ggtagttggg ccagccnacg annnnctcag   2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
agatttgcca gctgaagtag gggacaagga gggaagagtg aagaacccag ccagtaatgt   2700
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcgg   2820
gggtggaggg gatatattcg gggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
cgtaggtgtc gagcatgaca ccatactcgg acttgggctt ggcgatatca acctcggaca   3060
tggacgagag cgatgtggaa gaggccgagt ggcggggaga gtctgaagga gagacggcgg   3120
cagactcaga atccgtcaca gtagttgagg tgacggtgcg tctaagcgca gggttctgct   3180
tgggcagagc cgaagtggac gccatggaga gctgggttag tttgtgtaga gagtgtgtgt   3240
tgctagcgac tttcggattg tgtcattaca caaaacgcgt cgtctcgaca ctgatcttgt   3300
cgtggatact cacggctcgg acatcgtcgc cgacgatgac accggacttt cgcttaagga   3360
cgtcagtaac aggcattgtg tgatgtgtag tttagatttc gaatctgtgg ggaaagaaag   3420
gaaaaaagag actggcaacc gattgggaga gccactgttt atatataccc tagacaagcc   3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt tcgcagctct aaaggctata   3720
acaagtcaca ccaccctgct cgacctcagc gccctcactt tttgttaaga caaactgtac   3780
```

-continued

```
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttattt   3960
gtgccattga gccccgttat cctcgtatct tctacccccc atcccatccc tttgttggtg   4020
caaccctacc catttattgt tgggtgcagc ccaaccgacg tggagagctt ggcttggcca   4080
tataaaaagg ccccccccta gtggcaatgg cagaaagtca gctgtgagtt gttgaatttg   4140
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagcccccct tcaccccaca   4380
tatcaaacct cccccggttc ccacacttgc cgttaagggc gtagggtact gcagtctgga   4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctggggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccaccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
```

-continued

```
cggagagaag ccaagacgag tactcaaagg ggattacacc atccatatcc acagacacaa   6180

gctggggaaa ggttctatat acactttccg gaataccgta gtttccgatg ttatcaatgg   6240

gggcagccag gatttcaggc acttcggtgt ctcggggtga aatggcgttc ttggcctcca   6300

tcaagtcgta ccatgtcttc atttgcctgt caaagtaaaa cagaagcaga tgaagaatga   6360

acttgaagtg aaggaattta aattgccccg gagaagacgg ccaggccgcc tagatgacaa   6420

attcaacaac tcacagctga ctttctgcca ttgccactag gggggggcct ttttatatgg   6480

ccaagccaag ctctccacgt cggttgggct gcacccaaca ataaatgggt agggttgcac   6540

caacaaaggg atgggatggg gggtagaaga tacgaggata acggggctca atggcacaaa   6600

taagaacgaa tactgccatt aagactcgtg atccagcgac tgacaccatt gcatcatcta   6660

agggcctcaa aactacctcg gaactgctgc gctgatctgg acaccacaga ggttccgagc   6720

actttaggtt gcaccaaatg tcccaccagg tgcaggcaga aaacgctgga acagcgtgta   6780

cagtttgtct taacaaaaag tgagggcgct gaggtcgagc agggtggtgt gacttgttat   6840

agcctttaga gctgcgaaag cgcgtatgga tttggctcat caggccagat tgagggtctg   6900

tggacacatg tcatgttagt gtacttcaat cgccccctgg atatagcccc gacaataggc   6960

cgtggcctca tttttttgcc ttccgcacat ttccattgct cggtacccac accttgcttc   7020

tcctgcactt gccaacctta atactggttt acattgacca acatcttaca agcgggggc   7080

ttgtctaggg tatatataaa cagtggctct cccaatcggt tgccagtctc tttttccctt   7140

tctttcccca cagattcgaa atctaaacta cacatcacac aatgcctgtt actgacgtcc   7200

ttaagcgaaa gtccggtgtc atcgtcggcg acgatgtccg agccgtgagt atccacgaca   7260

agatcagtgt cgagacgacg cgttttgtgt aatgacacaa tccgaaagtc gctagcaaca   7320

cacactctct acacaaacta acccagctct ccatggagtc cattgctccc ttcctgccct   7380

ccaagatgcc tcaggacctg ttcatggacc tcgccagcgc tatcggtgtc cgagctgctc   7440

cctacgtcga tcccctggag gctgccctgg ttgcccaggc cgagaagtac attcccacca   7500

ttgtccatca cactcgaggc ttcctggttg ccgtggagtc tcccctggct cgagagctgc   7560

ctctgatgaa ccccttccac gtgctcctga tcgtgctcgc ctacctggtc accgtgtttg   7620

tgggtatgca gatcatgaag aactttgaac gattcgaggt caagaccttc tccctcctgc   7680

acaacttctg tctggtctcc atctccgcct acatgtgcgg tggcatcctg tacgaggctt   7740

atcaggccaa ctatggactg tttgagaacg ctgccgatca caccttcaag ggtctcccta   7800

tggctaagat gatctggctc ttctacttct ccaagatcat ggagtttgtc gacaccatga   7860

tcatggtcct caagaagaac aaccgacaga tttcctttct gcacgtgtac caccactctt   7920

ccatcttcac catctggtgg ctggtcacct tcgttgctcc caacggtgaa gcctacttct   7980

ctgctgccct gaactccttc atccacgtca tcatgtacgg ctactacttt ctgtctgccc   8040

tgggcttcaa gcaggtgtcg ttcatcaagt tctacatcac tcgatcccag atgacccagt   8100

tctgcatgat gtctgtccag tcttcctggg acatgtacgc catgaaggtc cttggccgac   8160

ctggataccc cttcttcatc accgctctgc tctggttcta catgtggacc atgctcggtc   8220

tcttctacaa cttttaccga aagaacgcca agctcgccaa gcaggccaag gctgacgctg   8280

ccaaggagaa ggccagaaag ctccagtaag cggccgcaag tgtggatggg gaagtgagtg   8340

cccggttctg tgtgcacaat tggcaatcca agatggatgg attcaacaca gggatatagc   8400

gagctacgtg gtggtgcgag gatatagcaa cggatattta tgtttgacac ttgagaatgt   8460

acgatacaag cactgtccaa gtacaatact aaacatactg tacatactca tactcgtacc   8520
```

-continued

```
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt ttgatcatgc acacataagg tccgacctta tcggcaagct   8700
caatgagctc cttggtggtg gtaacatcca gagaagcaca caggttggtt ttcttggctg   8760
ccacgagctt gagcactcga gcggcaaagg cggacttgtg gacgttagct cgagcttcgt   8820
aggagggcat tttggtggtg aagaggagac tgaaataaat ttagtctgca gaactttta   8880
tcggaacctt atctggggca gtgaagtata tgttatggta atagttacga gttagttgaa   8940
cttatagata gactggacta tacggctatc ggtccaaatt agaaagaacg tcaatggctc   9000
tctgggcgtc gcctttgccg acaaaaatgt gatcatgatg aaagccagca atgacgttgc   9060
agctgatatt gttgtcggcc aaccgcgccg aaaacgcagc tgtcagaccc acagcctcca   9120
acgaagaatg tatcgtcaaa gtgatccaag cacactcata gttggagtcg tactccaaag   9180
gcggcaatga cgagtcagac agatactcgt cgacctttc cttgggaacc accaccgtca   9240
gcccttctga ctcacgtatt gtagccaccg acacaggcaa cagtccgtgg atagcagaat   9300
atgtcttgtc ggtccatttc tcaccaactt taggcgtcaa gtgaatgttg cagaagaagt   9360
atgtgccttc attgagaatc ggtgttgctg atttcaataa agtcttgaga tcagtttggc   9420
gcgccagctg cattaatgaa tcggccaacg cgcggggaga ggcggtttgc gtattgggcg   9480
ctcttccgct tcctcgctca ctgactcgct gcgctcggtc gttcggctgc ggcgagcggt   9540
atcagctcac tcaaaggcgg taatacggtt atccacagaa tcaggggata acgcaggaaa   9600
gaacatgtga gcaaaaggcc agcaaaaggc caggaaccgt aaaaaggccg cgttgctggc   9660
gtttttccat aggctccgcc cccctgacga gcatcacaaa aatcgacgct caagtcagag   9720
gtggcgaaac ccgacaggac tataaagata ccaggcgttt ccccctggaa gctccctcgt   9780
gcgctctcct gttccgaccc tgccgcttac cggatacctg tccgcctttc tcccttcggg   9840
aagcgtggcg ctttctcata gctcacgctg taggtatctc agttcggtgt aggtcgttcg   9900
ctccaagctg ggctgtgtgc acgaaccccc cgttcagccc gaccgctgcg ccttatccgg   9960
taactatcgt cttgagtcca acccggtaag acacgactta tcgccactgg cagcagccac  10020
tggtaacagg attagcagag cgaggtatgt aggcggtgct acagagttct tgaagtggtg  10080
gcctaactac ggctacacta gaagaacagt atttggtatc tgcgctctgc tgaagccagt  10140
taccttcgga aaaagagttg gtagctcttg atccggcaaa caaaccaccg ctggtagcgg  10200
tggttttttt gtttgcaagc agcagattac gcgcagaaaa aaaggatctc aagaagatcc  10260
tttgatcttt tctacggggt ctgacgctca gtggaacgaa aactcacgtt aagggatttt  10320
ggtcatgaga ttatcaaaaa ggatcttcac ctagatcctt ttaaattaaa aatgaagttt  10380
taaatcaatc taaagtatat atgagtaaac ttggtctgac agttaccaat gcttaatcag  10440
tgaggcacct atctcagcga tctgtctatt tcgttcatcc atagttgcct gactccccgt  10500
cgtgtagata actacgatac gggagggctt accatctggc cccagtgctg caatgatacc  10560
gcgagaccca cgctcaccgg ctccagattt atcagcaata aaccagccag ccggaagggc  10620
cgagcgcaga agtggtcctg caactttatc cgcctccatc cagtctatta attgttgccg  10680
ggaagctaga gtaagtagtt cgccagttaa tagtttgcgc aacgttgttg ccattgctac  10740
aggcatcgtg gtgtcacgct cgtcgtttgg tatggcttca ttcagctccg gttcccaacg  10800
atcaaggcga gttacatgat cccccatgtt gtgcaaaaaa gcggttagct ccttcggtcc  10860
```

-continued

```
tccgatcgtt gtcagaagta agttggccgc agtgttatca ctcatggtta tggcagcact  10920

gcataattct cttactgtca tgccatccgt aagatgcttt tctgtgactg gtgagtactc  10980

aaccaagtca ttctgagaat agtgtatgcg gcgaccgagt tgctcttgcc cggcgtcaat  11040

acgggataat accgcgccac atagcagaac tttaaaagtg ctcatcattg gaaaacgttc  11100

ttcggggcga aaactctcaa ggatcttacc gctgttgaga tccagttcga tgtaacccac  11160

tcgtgcaccc aactgatctt cagcatcttt tactttcacc agcgtttctg ggtgagcaaa  11220

aacaggaagg caaaatgccg caaaaaaggg aataagggcg acacggaaat gttgaatact  11280

catactcttc ctttttcaat attattgaag catttatcag ggttattgtc tcatgagcgg  11340

atacatattt gaatgtattt agaaaaataa acaaataggg gttccgcgca catttccccg  11400

aaaagtgcca cctgatgcgg tgtgaaatac cgcacagatg cgtaaggaga aaataccgca  11460

tcaggaaatt gtaagcgtta atattttgtt aaaattcgcg ttaaattttt gttaaatcag  11520

ctcatttttt aaccaatagg ccgaaatcgg caaaatccct tataaatcaa aagaatagac  11580

cgagataggg ttgagtgttg ttccagtttg gaacaagagt ccactattaa agaacgtgga  11640

ctccaacgtc aaagggcgaa aaaccgtcta tcagggcgat ggcccactac gtgaaccatc  11700

accctaatca agttttttgg ggtcgaggtg ccgtaaagca ctaaatcgga accctaaagg  11760

gagcccccga tttagagctt gacggggaaa gccggcgaac gtggcgagaa aggaagggaa  11820

gaaagcgaaa ggagcgggcg ctagggcgct ggcaagtgta gcggtcacgc tgcgcgtaac  11880

caccacaccc gccgcgctta atgcgccgct acagggcgcg tccattcgcc attcaggctg  11940

cgcaactgtt gggaagggcg atcggtgcgg gcctcttcgc tattacgcca gctggcgaaa  12000

gggggatgtg ctgcaaggcg attaagttgg gtaacgccag ggttttccca gtcacgacgt  12060

tgtaaaacga cggccagtga attgtaatac gactcactat agggcgaatt gggcccgacg  12120

tcgcatgcag tggtggtatt gtgactgggg atgtagttga gaataagtca tacacaagtc  12180

agctttcttc gagcctcata taagtataag tagttcaacg tattagcact gtacccagca  12240

tctccgtatc gagaaacaca acaacatgcc ccattggaca gatcatgcgg atacacaggt  12300

tgtgcagtat catacatact cgatcagaca ggtcgtctga ccatcataca agctgaacaa  12360

gcgctccata cttgcacgct ctctatatac acagttaaat tacatatcca tagtctaacc  12420

tctaacagtt aatcttctgg taagcctccc agccagcctt ctggtatcgc ttggcctcct  12480

caataggatc tcggttctgg ccgtacagac ctcggccgac aattatgata tccgttccgg  12540

tagacatgac atcctcaaca gttcggtact gctgtccgag agcgtctccc ttgtcgtcaa  12600

gacccacccc gggggtcaga ataagccagt cctcagagtc gcccttaat              12649
```

<210> SEQ ID NO 15
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 15

```
atggccaact cctctgtctg ggacgacgtg gtcggacgag tcgagaccgg tgtcgaccag     60

tggatggacg gagctaagcc ctacgctctg accgacggtc tgcccatgat ggacgtctcc    120

accatgctcg ccttcgaggt cggctacatg gccatgctgc tcttcggcat tcccatcatg    180

aagcagatgg agaagccctt cgagctgaag accatcaagc tgctccacaa cctgttcctc    240
```

-continued

```
ttcggactgt ccctctacat gtgcgtcgag accatccgac aggctatcct gggtggctac    300

aaggtcttcg gcaacgacat ggagaagggc aacgagtccc acgctcaggg catgtcccga    360

atcgtctacg tgttctacgt ctccaaggcc tacgagttcc tggacaccgc tatcatgatc    420

ctgtgcaaga agttcaacca ggtctccttc ctgcacgtgt accaccatgc caccatcttc    480

gccatctggt gggctattgc caagtacgct cctggtggcg acgcctactt ctccgtcatc    540

ctcaactcct tcgtccacac cgtcatgtac gcctactact tcttttcctc tcagggcttc    600

ggcttcgtca agcccatcaa gccctacatc accactctgc agatgaccca gttcatggct    660

atgctggtgc agtccctgta cgactacctc ttcccctgcg actaccctca ggctctggtc    720

cagctgctcg gcgtgtacat gatcaccctg ctcgctctgt tcggcaactt ctttgtccag    780

tcctacctga agaagcccaa gaagtccaag accaactaa                           819
```

```
<210> SEQ ID NO 16
<211> LENGTH: 272
<212> TYPE: PRT
<213> ORGANISM: Thraustochytrium aureum

<400> SEQUENCE: 16

Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270
```

-continued

<210> SEQ ID NO 17
<211> LENGTH: 13034
<212> TYPE: DNA
<213> ORGANISM: Artificial Sequence
<220> FEATURE:
<223> OTHER INFORMATION: Plasmid pDMW271

<400> SEQUENCE: 17
cgatgcagaa ttcaggagag accgggttgg cggcgtattt gtgtcccaaa aaacagcccc 60
aattgcccca attgacccca aattgaccca gtagcgggcc caaccccggc gagagccccc 120
ttcaccccac atatcaaacc tcccccggtt cccacacttg ccgttaaggg cgtagggtac 180
tgcagtctgg aatctacgct tgttcagact ttgtactagt ttctttgtct ggccatccgg 240
gtaacccatg ccggacgcaa aatagactac tgaaaatttt tttgctttgt ggttgggact 300
ttagccaagg gtataaaaga ccaccgtccc cgaattacct ttcctcttct tttctctctc 360
tccttgtcaa ctcacacccg aaatcgttaa gcatttcctt ctgagtataa gaatcattca 420
ccatggatgg ctcccgaccc tgtcgctgcc gagaccgctg cccagggtcc cactccccga 480
tacttcacct gggacgaggt cgcccagcga tccggttgcg aggaacgatg gctggtcatc 540
gaccgaaagg tgtacaacat ctctgagttc acccgacgac atcccggtgg ctcccgagtg 600
atctcgcact acgctggaca ggacgccact gaccccttcg ttgcctttca cattaacaag 660
ggcctggtta agaagtacat gaactccctg ctcattggag agctgtctcc cgaacagcct 720
tcgtttgagc ctaccaagaa caaggagctg accgacgagt ttcgagagct ccgagccacc 780
gttgagcgaa tgggactgat gaaggccaac catgtcttct ttctgctcta cctgctccac 840
attcttctcc ttgacggagc tgcctggctt accctgtggg tcttcggcac ttcctttctg 900
ccctttcttc tctgcgccgt cctgctctct gccgtgcagg ctcaggctgg ttggcttcag 960
catgactttg gtcacctttc cgtgttctct acctccaagt ggaaccacct gctccatcac 1020
ttcgtgatcg gccacctcaa gggtgctcct gcctcgtggt ggaaccacat gcatttccag 1080
caccatgcca agcccaactg ttttcgaaag gatcccgaca tcaacatgca ccccttcttt 1140
ttcgctcttg gcaagatcct gtccgtcgag ctcggaaagc agaagaagaa gtacatgccc 1200
tacaaccacc agcacaagta cttcttcctg attggacctc ccgctctcct gcctctttac 1260
tttcagtggt acatctttta ctttgttatt cagcgaaaga agtgggttga tcttgcctgg 1320
atgatcacct tctacgtccg attcttcctg acctacgtcc ctctccttgg actgaaggcc 1380
tttctcggtc tgttctttat cgtccgattc ctggagtcca actggttcgt gtgggtgacc 1440
cagatgaacc acattcccat gcacattgac catgatcgaa acatggactg ggtgtcgact 1500
cagctgcagg ccacctgcaa cgttcacaag tctgctttca acgactggtt ttccggtcac 1560
ctcaactttc agattgagca ccatctgttt cccaccatgc ctcgacacaa ctaccacaag 1620
gttgctcccc tggtccagtc gctctgtgcc aagcatggca tcgagtacca gtccaagccc 1680
ctgctctctg ccttcgctga catcattcac tcgctgaagg aatctggcca gctctggctc 1740
gatgcctacc tgcaccagta agcggccgca ttgatgattg gaaacacaca catgggttat 1800
atctaggtga gagttagttg gacagttata tattaaatca gctatgccaa cggtaacttc 1860
attcatgtca acgaggaacc agtgactgca agtaatatag aatttgacca ccttgccatt 1920
ctcttgcact cctttactat atctcattta tttcttatat acaaatcact tcttcttccc 1980
agcatcgagc tcggaaacct catgagcaat aacatcgtgg atctcgtcaa tagagggctt 2040
tttggactcc ttgctgttgg ccaccttgtc cttgctgtct ggctcattct gtttcaacgc 2100

-continued

```
cttttaatta acggagtagg tctcggtgtc ggaagcgacg ccagatccgt catcctcctt   2160
tcgctctcca aagtagatac ctccgacgag ctctcggaca atgatgaagt cggtgccctc   2220
aacgtttcgg atgggggaga gatcggcgag cttgggcgac agcagctggc agggtcgcag   2280
gttggcgtac aggttcaggt cctttcgcag cttgaggaga ccctgctcgg gtcgcacgtc   2340
ggttcgtccg tcgggagtgg tccatacggt gttggcagcg cctccgacag caccgagcat   2400
aatagagtca gcctttcggc agatgtcgag agtagcgtcg gtgatgggct cgccctcctt   2460
ctcaatggca gctcctccaa tgagtcggtc ctcaaacaca aactcggtgc cggaggcctc   2520
agcaacagac ttgagcacct tgacggcctc ggcaatcacc tcggggccac agaagtcgcc   2580
gccgagaaga acaatcttct tggagtcagt cttggtcttc ttagtttcgg gttccattgt   2640
ggatgtgtgt ggttgtatgt gtgatgtggt gtgtggagtg aaaatctgtg gctggcaaac   2700
gctcttgtat atatacgcac ttttgcccgt gctatgtgga agactaaacc tccgaagatt   2760
gtgactcagg tagtgcggta tcggctaggg acccaaacct tgtcgatgcc gatagcatgc   2820
gacgtcgggc ccaattcgcc ctatagtgag tcgtattaca attcactggc cgtcgtttta   2880
caacgtcgtg actgggaaaa ccctggcgtt acccaactta atcgccttgc agcacatccc   2940
cctttcgcca gctggcgtaa tagcgaagag gcccgcaccg atcgcccttc ccaacagttg   3000
cgcagcctga atggcgaatg gacgcgccct gtagcggcgc attaagcgcg gcgggtgtgg   3060
tggttacgcg cagcgtgacc gctacacttg ccagcgccct agcgcccgct cctttcgctt   3120
tcttcccttc ctttctcgcc acgttcgccg gctttccccg tcaagctcta aatcgggggc   3180
tccctttagg gttccgattt agtgctttac ggcacctcga ccccaaaaaa cttgattagg   3240
gtgatggttc acgtagtggg ccatcgccct gatagacggt ttttcgccct ttgacgttgg   3300
agtccacgtt ctttaatagt ggactcttgt tccaaactgg aacaacactc aaccctatct   3360
cggtctattc ttttgattta taagggattt tgccgatttc ggcctattgg ttaaaaaatg   3420
agctgattta acaaaaattt aacgcgaatt ttaacaaaat attaacgctt acaatttcct   3480
gatgcggtat tttctcctta cgcatctgtg cggtatttca caccgcatca ggtggcactt   3540
ttcggggaaa tgtgcgcgga acccctattt gtttattttt ctaaatacat tcaaatatgt   3600
atccgctcat gagacaataa ccctgataaa tgcttcaata atattgaaaa aggaagagta   3660
tgagtattca acatttccgt gtcgccctta ttcccttttt tgcggcattt tgccttcctg   3720
tttttgctca cccagaaacg ctggtgaaag taaaagatgc tgaagatcag ttgggtgcac   3780
gagtgggtta catcgaactg gatctcaaca gcggtaagat ccttgagagt tttcgccccg   3840
aagaacgttt tccaatgatg agcactttta aagttctgct atgtggcgcg gtattatccc   3900
gtattgacgc cgggcaagag caactcggtc gccgcataca ctattctcag aatgacttgg   3960
ttgagtactc accagtcaca gaaaagcatc ttacggatgg catgacagta agagaattat   4020
gcagtgctgc cataaccatg agtgataaca ctgcggccaa cttacttctg acaacgatcg   4080
gaggaccgaa ggagctaacc gcttttttgc acaacatggg ggatcatgta actcgccttg   4140
atcgttggga accggagctg aatgaagcca taccaaacga cgagcgtgac accacgatgc   4200
ctgtagcaat ggcaacaacg ttgcgcaaac tattaactgg cgaactactt actctagctt   4260
cccggcaaca attaatagac tggatggagg cggataaagt tgcaggacca cttctgcgct   4320
cggcccttcc ggctggctgg tttattgctg ataaatctgg agccggtgag cgtgggtctc   4380
gcggtatcat tgcagcactg gggccagatg gtaagccctc ccgtatcgta gttatctaca   4440
```

-continued

```
cgacggggag tcaggcaact atggatgaac gaaatagaca gatcgctgag ataggtgcct   4500
cactgattaa gcattggtaa ctgtcagacc aagtttactc atatatactt tagattgatt   4560
taaaacttca tttttaattt aaaaggatct aggtgaagat cctttttgat aatctcatga   4620
ccaaaatccc ttaacgtgag ttttcgttcc actgagcgtc agaccccgta gaaaagatca   4680
aaggatcttc ttgagatcct ttttttctgc gcgtaatctg ctgcttgcaa acaaaaaaac   4740
caccgctacc agcggtggtt tgtttgccgg atcaagagct accaactctt tttccgaagg   4800
taactggctt cagcagagcg cagataccaa atactgttct tctagtgtag ccgtagttag   4860
gccaccactt caagaactct gtagcaccgc ctacatacct cgctctgcta atcctgttac   4920
cagtggctgc tgccagtggc gataagtcgt gtcttaccgg gttggactca agacgatagt   4980
taccggataa ggcgcagcgg tcgggctgaa cggggggttc gtgcacacag cccagcttgg   5040
agcgaacgac ctacaccgaa ctgagatacc tacagcgtga gctatgagaa agcgccacgc   5100
ttcccgaagg gagaaaggcg gacaggtatc cggtaagcgg cagggtcgga acaggagagc   5160
gcacgaggga gcttccaggg ggaaacgcct ggtatcttta tagtcctgtc gggtttcgcc   5220
acctctgact tgagcgtcga tttttgtgat gctcgtcagg ggggcggagc ctatggaaaa   5280
acgccagcaa cgcggccttt ttacggttcc tggccttttg ctggcctttt gctcacatgt   5340
tctttcctgc gttatcccct gattctgtgg ataaccgtat taccgccttt gagtgagctg   5400
ataccgctcg ccgcagccga acgaccgagc gcagcgagtc agtgagcgag gaagcggaag   5460
agcgcccaat acgcaaaccg cctctccccg cgcgttggcc gattcattaa tgcagctggc   5520
gcgcccactg agctcgtcta acggacttga tatacaacca attaaaacaa atgaaaagaa   5580
atacagttct ttgtatcatt tgtaacaatt accctgtaca aactaaggta ttgaaatccc   5640
acaatattcc caaagtccac ccctttccaa attgtcatgc ctacaactca tataccaagc   5700
actaacctac caaacaccac taaaacccca caaaatatat cttaccgaat atacagtaac   5760
aagctaccac cacactcgtt gggtgcagtc gccagcttaa agatatctat ccacatcagc   5820
cacaactccc ttcctttaat aaaccgacta cacccttggc tattgaggtt atgagtgaat   5880
atactgtaga caagacactt tcaagaagac tgtttccaaa acgtaccact gtcctccact   5940
acaaacacac ccaatctgct tcttctagtc aaggttgcta caccggtaaa ttataaatca   6000
tcatttcatt agcagggcag ggcccttttt atagagtctt atacactagc ggaccctgcc   6060
ggtagaccaa cccgcaggcg cgtcagtttg ctccttccat caatgcgtcg tagaaacgac   6120
ttactccttc ttgagcagct ccttgacctt gttggcaaca agtctccgac ctcggaggtg   6180
gaggaagagc ctccgatatc ggcggtagtg ataccagcct cgacggactc cttgacggca   6240
gcctcaacag cgtcaccggc gggcttcatg ttaagagaga acttgagcat catggcggca   6300
gacagaatgg tggcgtacgc aactaacatg aatgaatacg atatacatca aagactatga   6360
tacgcagtat tgcacactgt acgagtaaga gcactagcca ctgcactcaa gtgaaaccgt   6420
tgcccgggta cgagtatgag tatgtacagt atgtttagta ttgtacttgg acagtgcttg   6480
tatcgtacat tctcaagtgt caaacataaa tatccgttgc tatatcctcg caccaccacg   6540
tagctcgcta tatccctgtg ttgaatccat ccatcttgga ttgccaattg tgcacacaga   6600
accgggcact cacttcccca tccacacttg cggccgctta gctgcctact cttccttggg   6660
acggagtcca agaacacgca agtgctccaa atgtgaagca aatgcttgcc aaaacgtatc   6720
cttgacaagg tatggaacct tgtactcgct gcaggtgttc ttgatgatgg ccagaatatc   6780
gggataatgg tgctgcgaca cgttggggaa cagatggtgc acagcctggt agttcaagct   6840
```

-continued

```
gccagtgatg ctggtccaga ggtgcgaatc gtgtgcgtaa tcctgcgtag tctcgacctg   6900
catagctgcc cagtcctttt ggatgatccc gttctcgtca ggcaacggcc actgaacttc   6960
ctcaacaacg tggttcgcct ggaaggtcag cgccagccag taagacgaca ccatgtccgc   7020
gaccgtgaac aagagcagca ccttgcccag gggcagatac tgcaggggaa caatcaggcg   7080
ataccagaca aagaaagcct tgccgcccca gaacatcaca gtgtgccatg tcgagatggg   7140
attgacacga atagcgtcat tggtcttgac aaagtacaaa atgttgatgt cctgaatgcg   7200
caccttgaac gccagcagtc cgtacaggaa aggaacaaac atgtgctggt tgatgtggtt   7260
gacaaaccac ttttggttgg gcttgatacg acgaacatcg ggctcagacg tcgacacgtc   7320
gggatctgct ccagcaatgt tggtgtaggg gtgatggccg agcatatgtt ggtacatcca   7380
caccaggtac gatgctccgt tgaaaaagtc gtgcgtggct cccagaatct tccagacagt   7440
ggggttgtgg gtcactgaaa agtgagacgc atcatgaaga gggttgagtc cgacttgtgc   7500
gcacgcaaat cccatgatga ttgcaaacac cacctgaagc catgtgcgtt cgacaacgaa   7560
aggcacaaag agctgcgcgt agtaggaagc gatcaaggat ccaaagataa gagcgtatcg   7620
tccccagatc tctggtctat tcttgggatc aatgttccga tccgtaaagt agccctcgac   7680
tctcgtcttg atggttttgt ggaacaccgt tggctccggg aagatgggca gctcattcga   7740
gaccagtgta ccgacatagt acttcttcat aatggcatct gcagccccaa acgcgtgata   7800
catctcaaag accggagtaa catctcggcc agctccgagc aggagagtgt ccactccacc   7860
aggatggcgg ctcaagaact ttgtgacatc gtacaccctg ccgcggatgg ccaagagtag   7920
gtcgtccttg gtgttatggg ccgccagctc ttcccaggtg aaggtttttc cttggtccgt   7980
tcccatggag agctgggtta gtttgtgtag agagtgtgtg ttgctagcga ctttcggatt   8040
gtgtcattac acaaaacgcg tcgtctcgac actgatcttg tcgtggatac tcacggctcg   8100
gacatcgtcg ccgacgatga caccggactt tcgcttaagg acgtcagtaa caggcattgt   8160
gtgatgtgta gtttagattt cgaatctgtg gggaaagaaa ggaaaaaaga gactggcaac   8220
cgattgggag agccactgtt tatatatacc ctagacaagc cccccgcttg taagatgttg   8280
gtcaatgtaa accagtatta aggttggcaa gtgcaggaga agcaaggtgt gggtaccgag   8340
caatggaaat gtgcggaagg caaaaaaatg aggccacggc ctattgtcgg ggctatatcc   8400
agggggcgat tgaagtacac taacatgaca tgtgtccaca gaccctcaat ctggcctgat   8460
gagccaaatc catacgcgct ttcgcagctc taaaggctat aacaagtcac accaccctgc   8520
tcgacctcag cgccctcact ttttgttaag acaaactgta cacgctgttc cagcgttttc   8580
tgcctgcacc tggtgggaca tttggtgcaa cctaaagtgc tcggaacctc tgtggtgtcc   8640
agatcagcgc agcagttccg aggtagtttt gaggccctta gatgatgcaa tggtgtcagt   8700
cgctggatca cgagtcttaa tggcagtatt cgttcttatt tgtgccattg agccccgtta   8760
tcctcgtatc ttctaccccc catcccatcc ctttgttggt gcaaccctac ccatttattg   8820
ttgggtgcag cccaaccgac gtggagagct tggcttggcc atataaaaag gcccccccct   8880
agtggcaatg gcagaaagtc agctgtgagt tgttgaattt gtcatctagg cggcctggcc   8940
gtcttctccg gggcaattta aattccttca cttcaagttc attcttcatc tgcttctgtt   9000
ttactttgac aggcaaatga agacatggta cgacttgatg gaggccaaga acgccatttc   9060
accccgagac accgaagtgc ctgaaatcct ggctgccccc attgataaca tcggaaacta   9120
cggtattccg gaaagtgtat atagaacctt tccccagctt gtgtctgtgg atatggatgg   9180
```

-continued

```
tgtaatcccc tttgagtact cgtcttggct tctctccgag cagtatgagg ctctctaatc   9240
tagcgcattt aatatctcaa tgtatttata tatttatctt ctcatgcggc cgcttagctg   9300
cctactcttc cttgggacgg agtccaagaa cacgcaagtg ctccaaatgt gaagcaaatg   9360
cttgccaaaa cgtatccttg acaaggtatg gaaccttgta ctcgctgcag gtgttcttga   9420
tgatggccag aatatcggga taatggtgct gcgacacgtt ggggaacaga tggtgcacag   9480
cctggtagtt caagctgcca gtgatgctgg tccagaggtg cgaatcgtgt gcgtaatcct   9540
gcgtagtctc gacctgcata gctgcccagt ccttttggat gatcccgttc tcgtcaggca   9600
acggccactg aacttcctca acaacgtggt tcgcctggaa ggtcagcgcc agccagtaag   9660
acgacaccat gtccgcgacc gtgaacaaga gcagcacctt gcccaggggc agatactgca   9720
ggggaacaat caggcgatac cagacaaaga aagccttgcc gccccagaac atcacagtgt   9780
gccatgtcga gatgggattg acacgaatag cgtcattggt cttgacaaag tacaaaatgt   9840
tgatgtcctg aatgcgcacc ttgaacgcca gcagtccgta caggaaagga acaaacatgt   9900
gctggttgat gtggttgaca aaccactttt ggttgggctt gatacgacga acatcgggct   9960
cagacgtcga cacgtcggga tctgctccag caatgttggt gtaggggtga tggccgagca  10020
tatgttggta catccacacc aggtacgatg ctccgttgaa aaagtcgtgc gtggctccca  10080
gaatcttcca gacagtgggg ttgtgggtca ctgaaaagtg agacgcatca tgaagagggt  10140
tgagtccgac ttgtgcgcac gcaaatccca tgatgattgc aaacaccacc tgaagccatg  10200
tgcgttcgac aacgaaaggc acaaagagct gcgcgtagta ggaagcgatc aaggatccaa  10260
agataagagc gtatcgtccc cagatctctg gtctattctt gggatcaatg ttccgatccg  10320
taaagtagcc ctcgactctc gtcttgatgg ttttgtggaa caccgttggc tccgggaaga  10380
tgggcagctc attcgagacc agtgtaccga catagtactt cttcataatg gcatctgcag  10440
ccccaaacgc gtgatacatc tcaaagaccg gagtaacatc tcggccagct ccgagcagga  10500
gagtgtccac tccaccagga tggcggctca agaactttgt gacatcgtac accctgccgc  10560
ggatggccaa gagtaggtcg tccttggtgt tatgggccgc cagctcttcc caggtgaagg  10620
tttttccttg gtccgttccc atggtgaatg attcttatac tcagaaggaa atgcttaacg  10680
atttcgggtg tgagttgaca aggagagaga gaaaagaaga ggaaaggtaa ttcggggacg  10740
gtggtctttt atacccttgg ctaaagtccc aaccacaaag caaaaaaatt ttcagtagtc  10800
tattttgcgt ccggcatggg ttacccggat ggccagacaa agaaactagt acaaagtctg  10860
aacaagcgta gattccagac tgcagtaccc tacgccctta acggcaagtg tgggaaccgg  10920
gggaggtttg atatgtgggg tgaagggggc tctcgccggg gttgggcccg ctactgggtc  10980
aatttggggt caattggggc aattggggct gtttttttggg acacaaatac gccgccaacc  11040
cggtctctcc tgatcgatgg gctgcaggaa ttctacaata cgtgagtcag aagggctgac  11100
ggtggtggtt cccaaggaaa aggtcgacga gtatctgtct gactcgtcat tgccgccttt  11160
ggagtacgac tccaactatg agtgtgcttg gatcactttg acgatacatt cttcgttgga  11220
ggctgtgggt ctgacagctg cgttttcggc gcggttggcc gacaacaata tcagctgcaa  11280
cgtcattgct ggctttcatc atgatcacat ttttgtcggc aaaggcgacg cccagagagc  11340
cattgacgtt ctttctaatt tggaccgata gccgtatagt ccagtctatc tataagttca  11400
actaactcgt aactattacc ataacatata cttcactgcc ccagataagg ttccgataaa  11460
aagttctgca gactaaattt atttcagtct cctcttcacc accaaaatgc cctcctacga  11520
agctcgagct aacgtccaca agtccgcctt tgccgctcga gtgctcaagc tcgtggcagc  11580
```

-continued caagaaaacc aacctgtgtg cttctctgga tgttaccacc accaaggagc tcattgagct 11640
tgccgataag gtcggacctt atgtgtgcat gatcaaaacc catatcgaca tcattgacga 11700
cttcacctac gccggcactg tgctccccct caaggaactt gctcttaagc acggtttctt 11760
cctgttcgag gacagaaagt tcgcagatat tggcaacact gtcaagcacc agtaccggtg 11820
tcaccgaatc gccgagtggt ccgatatcac caacgcccac ggtgtacccg gaaccggaat 11880
cattgctggc ctgcgagctg gtgccgagga aactgtctct gaacagaaga aggaggacgt 11940
ctctgactac gagaactccc agtacaagga gttcctagtc ccctctccca acgagaagct 12000
ggccagaggt ctgctcatgc tggccgagct gtcttgcaag ggctctctgg ccactggcga 12060
gtactccaag cagaccattg agcttgcccg atccgacccc gagtttgtgg ttggcttcat 12120
tgcccagaac cgacctaagg gcgactctga ggactggctt attctgaccc ccggggtggg 12180
tcttgacgac aagggagacg ctctcggaca gcagtaccga actgttgagg atgtcatgtc 12240
taccggaacg gatatcataa ttgtcggccg aggtctgtac ggccagaacc gagatcctat 12300
tgaggaggcc aagcgatacc agaaggctgg ctgggaggct taccagaaga ttaactgtta 12360
gaggttagac tatggatatg taatttaact gtgtatatag agagcgtgca agtatggagc 12420
gcttgttcag cttgtatgat ggtcagacga cctgtctgat cgagtatgta tgatactgca 12480
caacctgtgt atccgcatga tctgtccaat ggggcatgtt gttgtgtttc tcgatacgga 12540
gatgctgggt acagtgctaa tacgttgaac tacttatact tatatgaggc tcgaagaaag 12600
ctgacttgtg tatgacttat tctcaactac atccccagtc acaataccac cactgcacta 12660
ccactacacc agatctgcgt acactgttta aacggtaggt tagtgcttgg tatatgagtt 12720
gtaggcatga caatttggaa aggggtggac tttgggaata ttgtgggatt tcaatacctt 12780
agtttgtaca gggtaattgt tacaaatgat acaaagaact gtatttcttt tcatttgttt 12840
taattggttg tatatcaagt ccgttagacg agctcagtgc cttggctttt ggcactgtat 12900
ttcattttta gaggtacact acattcagtg aggtatggta aggttgaggg cataatgaag 12960
gcaccttgta ctgacagtca cagacctctc accgagaatt ttatgagata tactcgggtt 13020
cattttaggc tcat 13034

<210> SEQ ID NO 18
<211> LENGTH: 1335
<212> TYPE: DNA
<213> ORGANISM: Homo sapiens
<220> FEATURE:
<221> NAME/KEY: misc_feature
<223> OTHER INFORMATION: synthetic delta-5 desaturase (codon-optimized)

<400> SEQUENCE: 18
atggctcccg accctgtcgc tgccgagacc gctgcccagg gtcccactcc ccgatacttc 60
acctgggacg aggtcgccca gcgatccggt tgcgaggaac gatggctggt catcgaccga 120
aaggtgtaca acatctctga gttcacccga cgacatcccg gtggctcccg agtgatctcg 180
cactacgctg gacaggacgc cactgacccc ttcgttgcct ttcacattaa caagggcctg 240
gttaagaagt acatgaactc cctgctcatt ggagagctgt ctcccgaaca gccttcgttt 300
gagcctacca agaacaagga gctgaccgac gagtttcgag agctccgagc caccgttgag 360
cgaatgggac tgatgaaggc caaccatgtc ttctttctgc tctacctgct ccacattctt 420
ctccttgacg gagctgcctg gcttaccctg tgggtcttcg gcacttcctt tctgcccttt 480
cttctctgcg ccgtcctgct ctctgccgtg caggctcagg ctggttggct tcagcatgac 540

-continued

```
tttggtcacc tttccgtgtt ctctacctcc aagtggaacc acctgctcca tcacttcgtg    600

atcggccacc tcaagggtgc tcctgcctcg tggtggaacc acatgcattt ccagcaccat    660

gccaagccca actgttttcg aaaggatccc gacatcaaca tgcacccctt ctttttcgct    720

cttggcaaga tcctgtccgt cgagctcgga aagcagaaga agaagtacat gccctacaac    780

caccagcaca agtacttctt cctgattgga cctcccgctc tcctgcctct ttactttcag    840

tggtacatct tttactttgt tattcagcga aagaagtggg ttgatcttgc ctggatgatc    900

accttctacg tccgattctt cctgacctac gtccctctcc ttggactgaa ggcctttctc    960

ggtctgttct ttatcgtccg attcctggag tccaactggt tcgtgtgggt gacccagatg   1020

aaccacattc ccatgcacat tgaccatgat cgaaacatgg actgggtgtc gactcagctg   1080

caggccacct gcaacgttca caagtctgct ttcaacgact ggttttccgg tcacctcaac   1140

tttcagattg agcaccatct gtttcccacc atgcctcgac acaactacca caaggttgct   1200

cccctggtcc agtcgctctg tgccaagcat ggcatcgagt accagtccaa gcccctgctc   1260

tctgccttcg ctgacatcat tcactcgctg aaggaatctg gccagctctg gctcgatgcc   1320

tacctgcacc agtaa                                                    1335
```

```
<210> SEQ ID NO 19
<211> LENGTH: 444
<212> TYPE: PRT
<213> ORGANISM: Homo sapiens

<400> SEQUENCE: 19

Met Ala Pro Asp Pro Val Ala Ala Glu Thr Ala Ala Gln Gly Pro Thr
1               5                   10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220
```

-continued

```
Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
            340                 345                 350

Met Asp Trp Val Ser Thr Gln Leu Gln Ala Thr Cys Asn Val His Lys
        355                 360                 365

Ser Ala Phe Asn Asp Trp Phe Ser Gly His Leu Asn Phe Gln Ile Glu
    370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
                405                 410                 415

Lys Pro Leu Leu Ser Ala Phe Ala Asp Ile Ile His Ser Leu Lys Glu
            420                 425                 430

Ser Gly Gln Leu Trp Leu Asp Ala Tyr Leu His Gln
        435                 440
```

<210> SEQ ID NO 20
<211> LENGTH: 8867
<212> TYPE: DNA
<213> ORGANISM: Artificial Sequencec
<220> FEATURE:
<223> OTHER INFORMATION: Plasmid pZP3-P7U

<400> SEQUENCE: 20

```
aattcaggag agaccgggtt ggcggcgtat ttgtgtccca aaaaacagcc ccaattgccc      60

caattgaccc caaattgacc cagtagcggg cccaaccccg gcgagagccc ccttcacccc     120

acatatcaaa cctcccccgg ttcccacact tgccgttaag ggcgtagggt actgcagtct     180

ggaatctacg cttgttcaga ctttgtacta gtttctttgt ctggccatcc gggtaaccca     240

tgccggacgc aaaatagact actgaaaatt tttttgcttt gtggttggga ctttagccaa     300

gggtataaaa gaccaccgtc cccgaattac ctttcctctt cttttctctc tctccttgtc     360

aactcacacc cgaaatcgtt aagcatttcc ttctgagtat aagaatcatt caccatggac     420

ttcctggagg cagaagaact tgttatggaa aagctcaaga gagagaagcc aagatactat     480

caagacatgt gtcgcaactt aattaagatg acgacatttg cgagctggac gaggaataga     540

tggagcgtgt gttctgagtc gatgttttct atggagttgt gagtgttagt agacatgatg     600

ggtttatata tgatgaatga atagatgtga ttttgatttg cacgatggaa ttgagaactt     660

tgtaaacgta catgggaatg tatgaatgtg ggggttttgt gactggataa ctgacggtca     720

gtggacgccg ttgttcaaat atccaagaga tgcgagaaac tttgggtcaa gtgaacatgt     780

cctctctgtt caagtaaacc atcaactatg ggtagtatat ttagtaagga caagagttga     840
```

-continued

```
gattctttgg agtcctagaa acgtattttc gcgttccaag atcaaattag tagagtaata    900
cgggcacggg aatccattca tagtctcaat tttcccatag gtgtgctaca aggtgttgag    960
atgtggtaca gtaccaccat gattcgaggt aaagagccca gaagtcattg atgaggtcaa   1020
gaaatacaca gatctacagc tcaatacaat gaatatcttc tttcatattc ttcaggtgac   1080
accaagggtg tctattttcc ccagaaatgc gtgaaaaggc gcgtgtgtag cgtggagtat   1140
gggttcggtt ggcgtatcct tcatatatcg acgaaatagt agggcaagag atgacaaaaa   1200
gtatctatat gtagacagcg tagaatatgg atttgattgg tataaattca tttattgcgt   1260
gtctcacaaa tactctcgat aagttggggt taaactggag atggaacaat gtcgatatct   1320
cgacgcatgc gacgtcgggc ccaattcgcc ctatagtgag tcgtattaca attcactggc   1380
cgtcgtttta caacgtcgtg actgggaaaa ccctggcgtt acccaactta atcgccttgc   1440
agcacatccc cctttcgcca gctggcgtaa tagcgaagag gcccgcaccg atcgcccttc   1500
ccaacagttg cgcagcctga atggcgaatg gacgcgccct gtagcggcgc attaagcgcg   1560
gcgggtgtgg tggttacgcg cagcgtgacc gctacacttg ccagcgccct agcgcccgct   1620
cctttcgctt tcttcccttc ctttctcgcc acgttcgccg gctttccccg tcaagctcta   1680
aatcgggggc tccctttagg gttccgattt agtgctttac ggcacctcga ccccaaaaaa   1740
cttgattagg gtgatggttc acgtagtggg ccatcgccct gatagacggt ttttcgccct   1800
ttgacgttgg agtccacgtt ctttaatagt ggactcttgt tccaaactgg aacaacactc   1860
aaccctatct cggtctattc ttttgattta taagggattt tgccgatttc ggcctattgg   1920
ttaaaaaatg agctgattta acaaaaattt aacgcgaatt ttaacaaaat attaacgctt   1980
acaatttcct gatgcggtat tttctcctta cgcatctgtg cggtatttca caccgcatca   2040
ggtggcactt ttcggggaaa tgtgcgcgga acccctattt gtttattttt ctaaatacat   2100
tcaaatatgt atccgctcat gagacaataa ccctgataaa tgcttcaata atattgaaaa   2160
aggaagagta tgagtattca acatttccgt gtcgccctta ttcccttttt tgcggcattt   2220
tgccttcctg tttttgctca cccagaaacg ctggtgaaag taaaagatgc tgaagatcag   2280
ttgggtgcac gagtgggtta catcgaactg gatctcaaca gcggtaagat ccttgagagt   2340
tttcgccccg aagaacgttt tccaatgatg agcactttta aagttctgct atgtggcgcg   2400
gtattatccc gtattgacgc cgggcaagag caactcggtc gccgcataca ctattctcag   2460
aatgacttgg ttgagtactc accagtcaca gaaaagcatc ttacggatgg catgacagta   2520
agagaattat gcagtgctgc cataaccatg agtgataaca ctgcggccaa cttacttctg   2580
acaacgatcg gaggaccgaa ggagctaacc gcttttttgc acaacatggg ggatcatgta   2640
actcgccttg atcgttggga accggagctg aatgaagcca taccaaacga cgagcgtgac   2700
accacgatgc ctgtagcaat ggcaacaacg ttgcgcaaac tattaactgg cgaactactt   2760
actctagctt cccggcaaca attaatagac tggatggagg cggataaagt tgcaggacca   2820
cttctgcgct cggcccttcc ggctggctgg tttattgctg ataaatctgg agccggtgag   2880
cgtgggtctc gcggtatcat tgcagcactg gggccagatg gtaagccctc ccgtatcgta   2940
gttatctaca cgacggggag tcaggcaact atggatgaac gaaatagaca gatcgctgag   3000
ataggtgcct cactgattaa gcattggtaa ctgtcagacc aagtttactc atatatactt   3060
tagattgatt taaaacttca tttttaattt aaaaggatct aggtgaagat cctttttgat   3120
aatctcatga ccaaaatccc ttaacgtgag ttttcgttcc actgagcgtc agaccccgta   3180
```

-continued

```
gaaaagatca aaggatcttc ttgagatcct ttttttctgc gcgtaatctg ctgcttgcaa   3240
acaaaaaaac caccgctacc agcggtggtt tgtttgccgg atcaagagct accaactctt   3300
tttccgaagg taactggctt cagcagagcg cagataccaa atactgttct tctagtgtag   3360
ccgtagttag gccaccactt caagaactct gtagcaccgc ctacatacct cgctctgcta   3420
atcctgttac cagtggctgc tgccagtggc gataagtcgt gtcttaccgg gttggactca   3480
agacgatagt taccggataa ggcgcagcgg tcgggctgaa cggggggttc gtgcacacag   3540
cccagcttgg agcgaacgac ctacaccgaa ctgagatacc tacagcgtga gctatgagaa   3600
agcgccacgc ttcccgaagg gagaaaggcg gacaggtatc cggtaagcgg cagggtcgga   3660
acaggagagc gcacgaggga gcttccaggg ggaaacgcct ggtatcttta tagtcctgtc   3720
gggtttcgcc acctctgact tgagcgtcga tttttgtgat gctcgtcagg ggggcggagc   3780
ctatggaaaa acgccagcaa cgcggccttt ttacggttcc tggccttttg ctggcctttt   3840
gctcacatgt tctttcctgc gttatcccct gattctgtgg ataaccgtat taccgccttt   3900
gagtgagctg ataccgctcg ccgcagccga acgaccgagc gcagcgagtc agtgagcgag   3960
gaagcggaag agcgcccaat acgcaaaccg cctctccccg cgcgttggcc gattcattaa   4020
tgcagctggc gcgccaccaa tcacaattct gaaaagcaca tcttgatctc ctcattgcgg   4080
ggagtccaac ggtggtctta ttccccccgaa tttcccgctc aatctcgttc cagaccgacc   4140
cggacacagt gcttaacgcc gttccgaaac tctaccgcag atatgctcca acggactggg   4200
ctgcatagat gtgatcctcg gcttggagaa atggataaaa gccggccaaa aaaaaagcgg   4260
aaaaaagcgg aaaaaaagag aaaaaaaatc gcaaaattg aaaaataggg ggaaaagacg   4320
caaaaacgca aggagggggg agtatatgac actgataagc aagctcacaa cggttcctct   4380
tattttttc ctcatcttct gcctaggttc ccaaaatccc agatgcttct ctccagtgcc   4440
aaaagtaagt accccacagg ttttcggccg aaaattccac gtgcagcaac gtcgtgtggg   4500
gtgttaaaat gtggggggg ggaaccagga caagaggctc ttgtgggagc cgaatgagag   4560
cacaaagcgg gcgggtgtga taagggcatt tttgcccatt ttcccttctc ctgtctctcc   4620
gacggtgatg gcgttgtgcg tcctctattt ctttttattt ctttttgttt tatttctctg   4680
actaccgatt tggtttgatt tcctcaaccc cacacaaata agctcgggcc gaggaatata   4740
tatatacacg gacacagtcg ccctgtggac aacacgtcac tacctctacg atacacaccg   4800
tacgttgtgt ggaagcttgt gagcggataa caatttcaca caggaaacag ctatgaccat   4860
gattacgcca agctcgaaat taaccctcac taaagggaac aaaagctgga gctccaccgc   4920
ggacacaata tctggtcaaa tttcagtttc gttacattta aattccttca cttcaagttc   4980
attcttcatc tgcttctgtt ttactttgac aggcaaatga agacatggta cgacttgatg   5040
gaggccaaga acgccatttc accccgagac accgaagtgc ctgaaatcct ggctgccccc   5100
attgataaca tcggaaacta cggtattccg gaaagtgtat atagaacctt tccccagctt   5160
gtgtctgtgg atatggatgg tgtaatcccc tttgagtact cgtcttggct tctctccgag   5220
cagtatgagg ctctctaatc tagcgcattt aatatctcaa tgtatttata tatttatctt   5280
ctcatgcggc cgcttaggtg gccttagtct tggtagcggc ttcggaaaca gccttggcct   5340
ccttgagagt gaacagcttg gcatccgagt cgaccacacc gtagtttgcg tagagtcggc   5400
cgactctgaa aaaggccttg atgatgggtt cgtcggactt tcgaaccagc tcgggaaagg   5460
cttgatggaa ggcctcggta gctcgcttga gcttgtagtg aggaatgatg ggaaagaggt   5520
gatgaatctg gtgggttccg atgttgtgag aaaggttgtc gatgagggca ccgtaggatc   5580
```

-continued

```
ggtcgacaga ggacaggttg cctttgacgt aggtccactc cgaatctgcg taccaaggtg   5640
tctcttcgtc gttgtgatga agaaaggtag taatgacgag catggatccg aacacaaaga   5700
cgggaccata gtagtagatg gccatagtct tgaagccgaa ctgcaggctg aggtagatgg   5760
acagggcagc cactccaaag tgcgcagcca gcgaaatgac cacggcagag acctgtcgaa   5820
caaagagagg ctcgaagggg ttgaagtggt tgacctttcg gggaggaaag ccttcgacca   5880
ggtaggcaaa ccaggctgca cccaaagcca gaatgaggtt tcgagacaga ggatgatcgt   5940
cggcctttcg ttgagggtag aagatttcgt ctcggtcgat gttgccagtg ttcttgtgat   6000
ggtgtctgtg ggtgagcttc caggactcga agggtgtaag gatgagagag tgaatgaagg   6060
ttccgatgac aaagttgagc aggtggtatc gggagaaggc accatgtcca gcgtcgtgac   6120
caacagtaaa gaatccccag aagacgatgc cctggagcag cacgtaaccg gtgcagagag   6180
cggcatccag agcccagagg ccttcgacaa cgggcagaga tcgtgcatgg tgaagtccga   6240
aggcgagcga cacagcaatg accaggcatc gaacggtgta gtacagagag agaggcacgg   6300
aggcctcgaa acactcggag ggcagagatc gcttgatctc ggtcagagta gggaactggt   6360
agggctgctt ggtagccatg gttgtgaatt agggtggtga gaatggttgg ttgtagggaa   6420
gaatcaaagg ccggtctcgg gatccgtggg tatatatata tatatatata tatacgatcc   6480
ttcgttacct ccctgttctc aaaactgtgg tttttcgttt ttcgtttttt gctttttttg   6540
atttttttag ggccaactaa gcttccagat ttcgctaatc acctttgtac taattacaag   6600
aaaggaagaa gctgattaga gttgggcttt ttatgcaact gtgctactcc ttatctctga   6660
tatgaaagtg tagacccaat cacatcatgt catttagagt tggtaatact gggaggatag   6720
ataaggcacg aaaacgagcc atagcagaca tgctgggtgt agccaagcag aagaaagtag   6780
atgggagcca attgacgagc gagggagcta cgccaatccg acatacgaca cgctgagatc   6840
gtcttggccg gggggtacct acagatgtcc aagggtaagt gcttgactgt aattgtatgt   6900
ctgaggacaa atatgtagtc agccgtataa agtcatacca ggcaccagtg ccatcatcga   6960
accactaact ctctatgata catgcctccg gtattattgt accatgcgtc gctttgttac   7020
atacgtatct tgcctttttc tctcagaaac tccagacttt ggctattggt cgagataagc   7080
ccggaccata gtgagtcttt cacactctac atttctccct tgctccaact atcgattgtt   7140
gtctactaac tatcgtacga taacttcgta tagcatacat tatacgaagt tatcgcgtcg   7200
acgagtatct gtctgactcg tcattgccgc ctttggagta cgactccaac tatgagtgtg   7260
cttggatcac tttgacgata cattcttcgt tggaggctgt gggtctgaca gctgcgtttt   7320
cggcgcggtt ggccgacaac aatatcagct gcaacgtcat tgctggcttt catcatgatc   7380
acatttttgt cggcaaaggc gacgcccaga gagccattga cgttctttct aatttggacc   7440
gatagccgta tagtccagtc tatctataag ttcaactaac tcgtaactat taccataaca   7500
tatacttcac tgccccagat aaggttccga taaaaagttc tgcagactaa atttatttca   7560
gtctcctctt caccaccaaa atgccctcct acgaagctcg agctaacgtc cacaagtccg   7620
cctttgccgc tcgagtgctc aagctcgtgg cagccaagaa aaccaacctg tgtgcttctc   7680
tggatgttac caccaccaag gagctcattg agcttgccga taaggtcgga ccttatgtgt   7740
gcatgatcaa aacccatatc gacatcattg acgacttcac ctacgccggc actgtgctcc   7800
ccctcaagga acttgctctt aagcacggtt tcttcctgtt cgaggacaga aagttcgcag   7860
atattggcaa cactgtcaag caccagtacc ggtgtcaccg aatcgccgag tggtccgata   7920
```

-continued

```
tcaccaacgc ccacggtgta cccggaaccg gaatcattgc tggcctgcga gctggtgccg   7980

aggaaactgt ctctgaacag aagaaggagg acgtctctga ctacgagaac tcccagtaca   8040

aggagttcct agtcccctct cccaacgaga agctggccag aggtctgctc atgctggccg   8100

agctgtcttg caagggctct ctggccactg gcgagtactc caagcagacc attgagcttg   8160

cccgatccga ccccgagttt gtggttggct tcattgccca gaaccgacct aagggcgact   8220

ctgaggactg gcttattctg acccccgggg tgggtcttga cgacaaggga gacgctctcg   8280

gacagcagta ccgaactgtt gaggatgtca tgtctaccgg aacggatatc ataattgtcg   8340

gccgaggtct gtacggccag aaccgagatc ctattgagga ggccaagcga taccagaagg   8400

ctggctggga ggcttaccag aagattaact gttagaggtt agactatgga tatgtaattt   8460

aactgtgtat atagagagcg tgcaagtatg gagcgcttgt tcagcttgta tgatggtcag   8520

acgacctgtc tgatcgagta tgtatgatac tgcacaacct gtgtatccgc atgatctgtc   8580

caatggggca tgttgttgtg tttctcgata cggagatgct gggtacagtg ctaatacgtt   8640

gaactactta tacttatatg aggctcgaag aaagctgact tgtgtatgac ttattctcaa   8700

ctacatcccc agtcacaata ccaccactgc actaccacta caccaaaacc atgatcaaac   8760

cacccatgga cttcctggag gcagaagaac ttgttatgga aaagctcaag agagagatca   8820

taacttcgta tagcatacat tatacgaagt tatcctgcag gtaaagg                 8867
```

<210> SEQ ID NO 21
<211> LENGTH: 34
<212> TYPE: DNA
<213> ORGANISM: Escherichia coli

<400> SEQUENCE: 21

```
ataacttcgt ataatgtatg ctatacgaag ttat                                  34
```

<210> SEQ ID NO 22
<211> LENGTH: 14655
<212> TYPE: DNA
<213> ORGANISM: Artificial Sequence
<220> FEATURE:
<223> OTHER INFORMATION: Plasmid pZKLeuN-29E3
<220> FEATURE:
<221> NAME/KEY: misc_feature
<222> LOCATION: (8822)..(8822)
<223> OTHER INFORMATION: n is a, c, g, or t
<220> FEATURE:
<221> NAME/KEY: misc_feature
<222> LOCATION: (8827)..(8830)
<223> OTHER INFORMATION: n is a, c, g, or t

<400> SEQUENCE: 22

```
cgattgttgt ctactaacta tcgtacgata acttcgtata gcatacatta tacgaagtta     60

tcgcgtcgac gagtatctgt ctgactcgtc attgccgcct ttggagtacg actccaacta    120

tgagtgtgct tggatcactt tgacgataca ttcttcgttg gaggctgtgg gtctgacagc    180

tgcgttttcg gcgcggttgg ccgacaacaa tatcagctgc aacgtcattg ctggctttca    240

tcatgatcac atttttgtcg gcaaaggcga cgcccagaga gccattgacg ttctttctaa    300

tttggaccga tagccgtata gtccagtcta tctataagtt caactaactc gtaactatta    360

ccataacata tacttcactg ccccagataa ggttccgata aaaagttctg cagactaaat    420

ttatttcagt ctcctcttca ccaccaaaat gccctcctac gaagctcgag ctaacgtcca    480

caagtccgcc tttgccgctc gagtgctcaa gctcgtggca gccaagaaaa ccaacctgtg    540

tgcttctctg gatgttacca ccaccaagga gctcattgag cttgccgata aggtcggacc    600
```

-continued

```
ttatgtgtgc atgatcaaaa cccatatcga catcattgac gacttcacct acgccggcac    660
tgtgctcccc ctcaaggaac ttgctcttaa gcacggtttc ttcctgttcg aggacagaaa    720
gttcgcagat attggcaaca ctgtcaagca ccagtaccgg tgtcaccgaa tcgccgagtg    780
gtccgatatc accaacgccc acggtgtacc cggaaccgga atcattgctg gcctgcgagc    840
tggtgccgag gaaactgtct ctgaacagaa gaaggaggac gtctctgact acgagaactc    900
ccagtacaag gagttcctag tcccctctcc caacgagaag ctggccagag gtctgctcat    960
gctggccgag ctgtcttgca agggctctct ggccactggc gagtactcca agcagaccat   1020
tgagcttgcc cgatccgacc ccgagtttgt ggttggcttc attgcccaga accgacctaa   1080
gggcgactct gaggactggc ttattctgac ccccggggtg ggtcttgacg acaagggaga   1140
cgctctcgga cagcagtacc gaactgttga ggatgtcatg tctaccggaa cggatatcat   1200
aattgtcggc cgaggtctgt acggccagaa ccgagatcct attgaggagg ccaagcgata   1260
ccagaaggct ggctgggagg cttaccagaa gattaactgt tagaggttag actatggata   1320
tgtaatttaa ctgtgtatat agagagcgtg caagtatgga gcgcttgttc agcttgtatg   1380
atggtcagac gacctgtctg atcgagtatg tatgatactg cacaacctgt gtatccgcat   1440
gatctgtcca atggggcatg ttgttgtgtt tctcgatacg gagatgctgg gtacagtgct   1500
aatacgttga actacttata cttatatgag gctcgaagaa agctgacttg tgtatgactt   1560
attctcaact acatccccag tcacaatacc accactgcac taccactaca ccaaaaccat   1620
gatcaaacca cccatggact tcctggaggc agaagaactt gttatggaaa agctcaagag   1680
agagatcata acttcgtata gcatacatta tacgaagtta tcctgcaggt aaaggaattc   1740
tggagtttct gagagaaaaa ggcaagatac gtatgtaaca aagcgacgca tggtacaata   1800
ataccggagg catgtatcat agagagttag tggttcgatg atggcactgg tgcctggtat   1860
gactttatac ggctgactac atatttgtcc tcagacatac aattacagtc aagcacttac   1920
ccttggacat ctgtaggtac cccccggcca agacgatctc agcgtgtcgt atgtcggatt   1980
ggcgtagctc cctcgctcgt caattggctc ccatctactt tcttctgctt ggctacaccc   2040
agcatgtctg ctatggctcg ttttcgtgcc ttatctatcc tcccagtatt accaactcta   2100
aatgacatga tgtgattggg tctacacttt catatcagag ataaggagta gcacagttgc   2160
ataaaaagcc caactctaat cagcttcttc ctttcttgta attagtacaa aggtgattag   2220
cgaaatctgg aagcttagtt ggccctaaaa aaatcaaaaa aagcaaaaaa cgaaaaacga   2280
aaaaccacag ttttgagaac agggaggtaa cgaaggatcg tatatatata tatatatata   2340
tatacccacg gatcccgaga ccggcctttg attcttccct acaaccaacc attctcacca   2400
ccctaattca caaccatgga gtctggaccc atgcctgctg gcattccctt ccctgagtac   2460
tatgacttct ttatggactg gaagactccc ctggccatcg ctgccaccta cactgctgcc   2520
gtcggtctct tcaaccccaa ggttggcaag gtctcccgag tggttgccaa gtcggctaac   2580
gcaaagcctg ccgagcgaac ccagtccgga gctgccatga ctgccttcgt ctttgtgcac   2640
aacctcattc tgtgtgtcta ctctggcatc accttctact acatgtttcc tgctatggtc   2700
aagaacttcc gaacccacac actgcacgaa gcctactgcg acacggatca gtccctctgg   2760
aacaacgcac ttggctactg gggttacctc ttctacctgt ccaagttcta cgaggtcatt   2820
gacaccatca tcatcatcct gaagggacga cggtcctcgc tgcttcagac ctaccaccat   2880
gctggagcca tgattaccat gtggtctggc atcaactacc aagccactcc catttggatc   2940
```

-continued

```
tttgtggtct tcaactcctt cattcacacc atcatgtact gttactatgc cttcacctct   3000

atcggattcc atcctcctgg caaaaagtac ctgacttcga tgcagattac tcagtttctg   3060

gtcggtatca ccattgccgt gtcctacctc ttcgttcctg gctgcatccg aacacccggt   3120

gctcagatgg ctgtctggat caacgtcggc tacctgtttc ccttgaccta tctgttcgtg   3180

gactttgcca agcgaaccta ctccaagcga tctgccattg ccgctcagaa aaaggctcag   3240

taagcggccg cattgatgat tggaaacaca cacatgggtt atatctaggt gagagttagt   3300

tggacagtta tatattaaat cagctatgcc aacggtaact tcattcatgt caacgaggaa   3360

ccagtgactg caagtaatat agaatttgac caccttgcca ttctcttgca ctcctttact   3420

atatctcatt tatttcttat atacaaatca cttcttcttc ccagcatcga gctcggaaac   3480

ctcatgagca ataacatcgt ggatctcgtc aatagagggc tttttggact ccttgctgtt   3540

ggccaccttg tccttgctgt ctggctcatt ctgtttcaac gccttttaat taacggagta   3600

ggtctcggtg tcggaagcga cgccagatcc gtcatcctcc tttcgctctc caaagtagat   3660

acctccgacg agctctcgga caatgatgaa gtcggtgccc tcaacgtttc ggatgggga    3720

gagatcggcg agcttgggcg acagcagctg gcagggtcgc aggttggcgt acaggttcag   3780

gtcctttcgc agcttgagga gaccctgctc gggtcgcacg tcggttcgtc cgtcgggagt   3840

ggtccatacg gtgttggcag cgcctccgac agcaccgagc ataatagagt cagcctttcg   3900

gcagatgtcg agagtagcgt cggtgatggg ctcgccctcc ttctcaatgg cagctcctcc   3960

aatgagtcgg tcctcaaaca caaactcggt gccggaggcc tcagcaacag acttgagcac   4020

cttgacggcc tcggcaatca cctcggggcc acagaagtcg ccgccgagaa gaacaatctt   4080

cttggagtca gtcttggtct tcttagtttc gggttccatt gtggatgtgt gtggttgtat   4140

gtgtgatgtg gtgtgtggag tgaaaatctg tggctggcaa acgctcttgt atatatacgc   4200

acttttgccc gtgctatgtg gaagactaaa cctccgaaga ttgtgactca ggtagtgcgg   4260

tatcggctag ggacccaaac cttgtcgatg ccgatagcat gcgacgtcgg gcccaattcg   4320

ccctatagtg agtcgtatta caattcactg gccgtcgttt tacaacgtcg tgactgggaa   4380

aaccctggcg ttacccaact taatcgcctt gcagcacatc ccccttttcgc cagctggcgt  4440

aatagcgaag aggcccgcac cgatcgccct tcccaacagt tgcgcagcct gaatggcgaa   4500

tggacgcgcc ctgtagcggc gcattaagcg cggcgggtgt ggtggttacg cgcagcgtga   4560

ccgctacact tgccagcgcc ctagcgcccg ctcctttcgc tttcttccct tcctttctcg   4620

ccacgttcgc cggctttccc cgtcaagctc taaatcgggg gctcccttta gggttccgat   4680

ttagtgcttt acggcacctc gaccccaaaa aacttgatta gggtgatggt tcacgtagtg   4740

ggccatcgcc ctgatagacg gtttttcgcc ctttgacgtt ggagtccacg ttctttaata   4800

gtggactctt gttccaaact ggaacaacac tcaaccctat ctcggtctat tcttttgatt   4860

tataagggat tttgccgatt tcggcctatt ggttaaaaaa tgagctgatt taacaaaaat   4920

ttaacgcgaa ttttaacaaa atattaacgc ttacaatttc ctgatgcggt attttctcct   4980

tacgcatctg tgcggtattt cacaccgcat caggtggcac ttttcgggga aatgtgcgcg   5040

gaacccctat ttgtttattt ttctaaatac attcaaatat gtatccgctc atgagacaat   5100

aaccctgata aatgcttcaa taatattgaa aaaggaagag tatgagtatt caacatttcc   5160

gtgtcgccct tattcccttt tttgcggcat tttgccttcc tgtttttgct cacccagaaa   5220

cgctggtgaa agtaaaagat gctgaagatc agttgggtgc acgagtgggt tacatcgaac   5280

tggatctcaa cagcggtaag atccttgaga gttttcgccc cgaagaacgt tttccaatga   5340
```

-continued

```
tgagcacttt taaagttctg ctatgtggcg cggtattatc ccgtattgac gccgggcaag   5400
agcaactcgg tcgccgcata cactattctc agaatgactt ggttgagtac tcaccagtca   5460
cagaaaagca tcttacggat ggcatgacag taagagaatt atgcagtgct gccataacca   5520
tgagtgataa cactgcggcc aacttacttc tgacaacgat cggaggaccg aaggagctaa   5580
ccgctttttt gcacaacatg ggggatcatg taactcgcct tgatcgttgg gaaccggagc   5640
tgaatgaagc cataccaaac gacgagcgtg acaccacgat gcctgtagca atggcaacaa   5700
cgttgcgcaa actattaact ggcgaactac ttactctagc ttcccggcaa caattaatag   5760
actggatgga ggcggataaa gttgcaggac cacttctgcg ctcggccctt ccggctggct   5820
ggtttattgc tgataaatct ggagccggtg agcgtgggtc tcgcggtatc attgcagcac   5880
tggggccaga tggtaagccc tcccgtatcg tagttatcta cacgacgggg agtcaggcaa   5940
ctatggatga acgaaataga cagatcgctg agataggtgc ctcactgatt aagcattggt   6000
aactgtcaga ccaagtttac tcatatatac tttagattga tttaaaactt catttttaat   6060
ttaaaaggat ctaggtgaag atcctttttg ataatctcat gaccaaaatc ccttaacgtg   6120
agttttcgtt ccactgagcg tcagaccccg tagaaaagat caaaggatct tcttgagatc   6180
cttttttct gcgcgtaatc tgctgcttgc aaacaaaaaa accaccgcta ccagcggtgg   6240
tttgtttgcc ggatcaagag ctaccaactc tttttccgaa ggtaactggc ttcagcagag   6300
cgcagatacc aaatactgtt cttctagtgt agccgtagtt aggccaccac ttcaagaact   6360
ctgtagcacc gcctacatac ctcgctctgc taatcctgtt accagtggct gctgccagtg   6420
gcgataagtc gtgtcttacc gggttggact caagacgata gttaccggat aaggcgcagc   6480
ggtcgggctg aacggggggt tcgtgcacac agcccagctt ggagcgaacg acctacaccg   6540
aactgagata cctacagcgt gagctatgag aaagcgccac gcttcccgaa gggagaaagg   6600
cggacaggta tccggtaagc ggcagggtcg gaacaggaga gcgcacgagg gagcttccag   6660
ggggaaacgc ctggtatctt tatagtcctg tcgggtttcg ccacctctga cttgagcgtc   6720
gatttttgtg atgctcgtca ggggggcgga gcctatggaa aaacgccagc aacgcggcct   6780
ttttacggtt cctggccttt tgctggcctt ttgctcacat gttctttcct gcgttatccc   6840
ctgattctgt ggataaccgt attaccgcct ttgagtgagc tgataccgct cgccgcagcc   6900
gaacgaccga gcgcagcgag tcagtgagcg aggaagcgga agagcgccca atacgcaaac   6960
cgcctctccc cgcgcgttgg ccgattcatt aatgcagctg gcgcgcccac tgagctcgtc   7020
taacggactt gatatacaac caattaaaac aaatgaaaag aaatacagtt ctttgtatca   7080
tttgtaacaa ttaccctgta caaactaagg tattgaaatc ccacaatatt cccaaagtcc   7140
acccctttcc aaattgtcat gcctacaact catataccaa gcactaacct accaaacacc   7200
actaaaaccc cacaaaatat atcttaccga atatacagta acaagctacc accacactcg   7260
ttgggtgcag tcgccagctt aaagatatct atccacatca gccacaactc ccttccttta   7320
ataaaccgac tacacccttg gctattgagg ttatgagtga atatactgta gacaagacac   7380
tttcaagaag actgtttcca aaacgtacca ctgtcctcca ctacaaacac acccaatctg   7440
cttcttctag tcaaggttgc tacaccggta aattataaat catcatttca ttagcagggc   7500
agggcccttt ttatagagtc ttatacacta gcggaccctg ccggtagacc aacccgcagg   7560
cgcgtcagtt tgctccttcc atcaatgcgt cgtagaaacg acttactcct tcttgagcag   7620
ctccttgacc ttgttggcaa caagtctccg acctcggagg tggaggaaga gcctccgata   7680
```

-continued

```
tcggcggtag tgataccagc ctcgacggac tccttgacgg cagcctcaac agcgtcaccg   7740
gcgggcttca tgttaagaga gaacttgagc atcatggcgg cagacagaat ggtggcgtac   7800
gcaactaaca tgaatgaata cgatatacat caaagactat gatacgcagt attgcacact   7860
gtacgagtaa gagcactagc cactgcactc aagtgaaacc gttgcccggg tacgagtatg   7920
agtatgtaca gtatgtttag tattgtactt ggacagtgct tgtatcgtac attctcaagt   7980
gtcaaacata aatatccgtt gctatatcct cgcaccacca cgtagctcgc tatatccctg   8040
tgttgaatcc atccatcttg gattgccaat tgtgcacaca gaaccgggca ctcacttccc   8100
catccacact tgcggccgcg cctacttaag caacgggctt gataacagcg gggggggtgc   8160
ccacgttgtt gcggttgcgg aagaacagaa cacccttacc agcaccctcg gcaccagcgc   8220
tgggctcaac ccactggcac atacgcgcac tgcggtacat ggcgcggatg aagccacgag   8280
gaccatcctg gacatcagcc cggtagtgct tgcccatgat gggcttaatg gcctcggtgg   8340
cctcgtccgc gttgtagaag gggatgctgc tgacgtagtg gtggaggaca tgagtctcga   8400
tgatgccgtg gagaaggtgg cggccgatga agcccatctc acggtcaatg gtagcagcgg   8460
caccacggac gaagttccac tcgtcgttgg tgtagtgggg aagggtaggg tcggtgtgct   8520
ggaggaaggt gatggcaacg agccagtggt taacccagag gtagggaaca aagtaccaga   8580
tggccatgtt gtagaaaccg aacttctgaa cgaggaagta cagagcagtg gccatcagac   8640
cgataccaat atcgctgagg acgatgagct tagcgtcact gttctcgtac agagggctgc   8700
ggggatcgaa gtggttaaca ccaccgccga ggccgttatg cttgcccttg ccgcgaccct   8760
cacgctggcg ctcgtggtag ttgtggccgg taacattggt gatgaggtag ttgggccagc   8820
cnacganpnn ctcagtaaga tgagcgagct cgtgggtcat ctttccgaga cgagtagcct   8880
gctgctcgcg ggttcgggga acgaagacca tgtcacgctc catgttgcca gtggccttgt   8940
ggtgctttcg gtgggagatt tgccagctga agtaggggac aaggagggaa gagtgaagaa   9000
cccagccagt aatgtcgttg atgatgcgag aatcggagaa agcaccgtga ccgcactcat   9060
gggcaataac ccagagacca gtaccgaaaa gaccctgaag aacggtgtac acggcccaca   9120
gaccagcgcg ggcgggggtg gaggggatat attcgggggt cacaaagttg taccagatgc   9180
tgaaagtggt agtcaggagg acaatgtcgc ggaggatata accgtatccc ttgagagcgg   9240
agcgcttgaa gcagtgctta gggatggcat tgtagatgtc cttgatggta aagtcgggaa   9300
cctcgaactg gttgccgtag gtgtcgagca tgacaccata ctcggacttg ggcttggcga   9360
tatcaacctc ggacatggac gagagcgatg tggaagaggc cgagtggcgg ggagagtctg   9420
aaggagagac ggcggcagac tcagaatccg tcacagtagt tgaggtgacg gtgcgtctaa   9480
gcgcagggtt ctgcttgggc agagccgaag tggacgccat ggttgatgtg tgtttaattc   9540
aagaatgaat atagagaaga gaagaagaaa aaagattcaa ttgagccggc gatgcagacc   9600
cttatataaa tgttgccttg gacagacgga gcaagcccgc ccaaacctac gttcggtata   9660
atatgttaag ctttttaaca caaaggtttg gcttggggta acctgatgtg gtgcaaaaga   9720
ccgggcgttg gcgagccatt gcgcgggcga atggggccgt gactcgtctc aaattcgagg   9780
gcgtgcctca attcgtgccc ccgtggcttt ttcccgccgt ttccgccccg tttgcaccac   9840
tgcagccgct tctttggttc ggacaccttg ctgcgagcta ggtgccttgt gctacttaaa   9900
aagtggcctc ccaacaccaa catgacatga gtgcgtgggc caagacacgt tggcggggtc   9960
gcagtcggct caatggcccg gaaaaaacgc tgctggagct ggttcggacg cagtccgccg  10020
cggcgtatgg atatccgcaa ggttccatag cgccattgcc ctccgtcggc gtctatcccg  10080
```

-continued

```
caacctctaa atagagcggg aatataaccc aagcttcttt tttttccttt aacacgcaca  10140
cccccaacta tcatgttgct gctgctgttt gactctactc tgtggagggg tgctcccacc  10200
caacccaacc tacaggtgga tccggcgctg tgattggctg ataagtctcc tatccggact  10260
aattctgacc aatgggacat gcgcgcagga cccaaatgcc gcaattacgt aaccccaacg  10320
aaatgcctac ccctctttgg agcccagcgg ccccaaatcc ccccaagcag cccggttcta  10380
ccggcttcca tctccaagca caagcagccc ggttctaccg gcttccatct ccaagcaccc  10440
ctttctccac accccacaaa aagacccgtg caggacatcc tactgcgtcg acatcattta  10500
aattccttca cttcaagttc attcttcatc tgcttctgtt ttactttgac aggcaaatga  10560
agacatggta cgacttgatg gaggccaaga acgccatttc accccgagac accgaagtgc  10620
ctgaaatcct ggctgccccc attgataaca tcggaaacta cggtattccg gaaagtgtat  10680
atagaacctt tccccagctt gtgtctgtgg atatggatgg tgtaatcccc tttgagtact  10740
cgtcttggct tctctccgag cagtatgagg ctctctaatc tagcgcattt aatatctcaa  10800
tgtatttata tatttatctt ctcatgcggc cgctcactga atctttttgg ctcccttgtg  10860
cttcctgacg atatacgttt gcacatagaa attcaagaac aaacacaaga ctgtgccaac  10920
ataaaagtaa ttgaagaacc agccaaacat cctcatccca tcttggcgat aacagggaat  10980
gttcctgtac ttccagacaa tgtagaaacc aacattgaat tgaatgatct gcattgatgt  11040
aatcagggat tttggcatgg ggaacttcag cttgatcaat ctggtccaat aataaccgta  11100
catgatccag tggatgaaac cattcaacag cacaaaaatc caaacagctt catttcggta  11160
attatagaac agccacatat ccatcggtgc ccccaaatga tggaagaatt gcaaccaggt  11220
cagaggcttg cccatcagtg gcaaatagaa ggagtcaata tactccagga acttgctcaa  11280
atagaacaac tgcgtggtga tcctgaagac gttgttgtca aaagccttct cgcagttgtc  11340
agacataaca ccgatggtgt acatggcata tgccattgag aggaatgatc ccaacgaata  11400
aatggacatg agaaggttgt aattggtgaa aacaaacttc atacgagact gacctttttgg  11460
accaaggggg ccaagagtga acttcaagat gacaaatgcg atggacaagt aaagcacctc  11520
acagtgactg gcatcactcc agagttgggc ataatcaact ggttgggtaa aacttcctgc  11580
ccaattgaga ctatttcatt caccacctcc atggccattg ctgtagatat gtcttgtgtg  11640
taagggggtt ggggtggttg tttgtgttct tgacttttgt gttagcaagg gaagacgggc  11700
aaaaaagtga gtgtggttgg gagggagaga cgagccttat atataatgct tgtttgtgtt  11760
tgtgcaagtg gacgccgaaa cgggcaggag ccaaactaaa caaggcagac aatgcgagct  11820
taattggatt gcctgatggg caggggttag ggctcgatca atgggggtgc gaagtgacaa  11880
aattgggaat taggttcgca agcaaggctg acaagacttt ggcccaaaca tttgtacgcg  11940
gtggacaaca ggagccaccc atcgtctgtc acgggctagc cggtcgtgcg tcctgtcagg  12000
ctccacctag gctccatgcc actccataca atcccactag tgtaccgcta ggccgctttt  12060
agctcccatc taagaccccc ccaaaacctc cactgtacag tgcactgtac tgtgtggcga  12120
tcaagggcaa gggaaaaaag gcgcaaacat gcacgcatgg aatgacgtag gtaaggcgtt  12180
actagactga aaagtggcac atttcggcgt gccaaagggt cctaggtgcg tttcgcgagc  12240
tgggcgccag gccaagccgc tccaaaacgc ctctccgact ccctccagcg gcctccatat  12300
ccccatccct ctccacagca atgttgttaa gccttgcaaa cgaaaaaata gaaaggctaa  12360
taagcttcca atattgtggt gtacgctgca taacgcaaca atgagcgcca aacaacacac  12420
```

-continued

```
acacacagca cacagcagca ttaaccacga tgaacagcat gacattacag gtgggtgtgt  12480
aatcagggcc ctgattgctg gtggtgggag cccccatcat gggcagatct gcgtacactg  12540
tttaaacagt gtacgcagat ctactataga ggaacattta aattgccccg gagaagacgg  12600
ccaggccgcc tagatgacaa attcaacaac tcacagctga ctttctgcca ttgccactag  12660
gggggggcct ttttatatgg ccaagccaag ctctccacgt cggttgggct gcacccaaca  12720
ataaatgggt agggttgcac caacaaaggg atgggatggg gggtagaaga tacgaggata  12780
acggggctca atggcacaaa taagaacgaa tactgccatt aagactcgtg atccagcgac  12840
tgacaccatt gcatcatcta agggcctcaa aactacctcg gaactgctgc gctgatctgg  12900
acaccacaga ggttccgagc actttaggtt gcaccaaatg tcccaccagg tgcaggcaga  12960
aaacgctgga acagcgtgta cagtttgtct taacaaaaag tgagggcgct gaggtcgagc  13020
agggtggtgt gacttgttat agcctttaga gctgcgaaag cgcgtatgga tttggctcat  13080
caggccagat tgagggtctg tggacacatg tcatgttagt gtacttcaat cgccccctgg  13140
atatagcccc gacaataggc cgtggcctca tttttttgcc ttccgcacat ttccattgct  13200
cgatacccac accttgcttc tcctgcactt gccaacctta atactggttt acattgacca  13260
acatcttaca agcggggggc ttgtctaggg tatatataaa cagtggctct cccaatcggt  13320
tgccagtctc ttttttcctt tctttcccca cagattcgaa atctaaacta cacatcacag  13380
aattccgagc cgtgagtatc cacgacaaga tcagtgtcga gacgacgcgt tttgtgtaat  13440
gacacaatcc gaaagtcgct agcaacacac actctctaca caaactaacc cagctctggt  13500
accatggagg tcgtgaacga aatcgtctcc attggccagg aggttcttcc caaggtcgac  13560
tatgctcagc tctggtctga tgcctcgcac tgcgaggtgc tgtacctctc catcgccttc  13620
gtcatcctga agttcaccct tggtcctctc ggacccaagg gtcagtctcg aatgaagttt  13680
gtgttcacca actacaacct gctcatgtcc atctactcgc tgggctcctt cctctctatg  13740
gcctacgcca tgtacaccat tggtgtcatg tccgacaact gcgagaaggc tttcgacaac  13800
aatgtcttcc gaatcaccac tcagctgttc tacctcagca agttcctcga gtacattgac  13860
tccttctatc tgcccctcat gggcaagcct ctgacctggt tgcagttctt tcaccatctc  13920
ggagctccta tggacatgtg gctgttctac aactaccgaa acgaagccgt ttggatcttt  13980
gtgctgctca acggcttcat tcactggatc atgtacggct actattggac ccgactgatc  14040
aagctcaagt tccctatgcc caagtccctg attacttcta tgcagatcat tcagttcaac  14100
gttggcttct acatcgtctg gaagtaccgg aacattccct gctaccgaca agatggaatg  14160
agaatgtttg gctggttttt caactacttc tacgttggta ctgtcctgtg tctgttcctc  14220
aacttctacg tgcagaccta catcgtccga aagcacaagg gagccaaaaa gattcagtga  14280
gcggccgcat gtacatacaa gattatttat agaaatgaat cgcgatcgaa caaagagtac  14340
gagtgtacga gtaggggatg atgataaaag tggaagaagt tccgcatctt tggatttatc  14400
aacgtgtagg acgatacttc ctgtaaaaat gcaatgtctt taccataggt tctgctgtag  14460
atgttattaa ctaccattaa catgtctact tgtacagttg cagaccagtt ggagtataga  14520
atggtacact taccaaaaag tgttgatggt tgtaactacg atatataaaa ctgttgacgg  14580
gatccccgct gatatgccta aggaacaatc aaagaggaag atattaattc agaatgctag  14640
tatacagtta gggat                                                  14655
```

<210> SEQ ID NO 23
<211> LENGTH: 777

-continued

<212> TYPE: DNA
<213> ORGANISM: Euglena gracilis
<220> FEATURE:
<221> NAME/KEY: misc_feature
<223> OTHER INFORMATION: synthetic delta-9 elongase (codon-optimized)

<400> SEQUENCE: 23

```
atggaggtcg tgaacgaaat cgtctccatt ggccaggagg ttcttcccaa ggtcgactat      60

gctcagctct ggtctgatgc ctcgcactgc gaggtgctgt acctctccat cgccttcgtc     120

atcctgaagt tcacccttgg tcctctcgga cccaagggtc agtctcgaat gaagtttgtg     180

ttcaccaact acaacctgct catgtccatc tactcgctgg gctccttcct ctctatggcc     240

tacgccatgt acaccattgg tgtcatgtcc gacaactgcg agaaggcttt cgacaacaat     300

gtcttccgaa tcaccactca gctgttctac ctcagcaagt tcctcgagta cattgactcc     360

ttctatctgc ccctcatggg caagcctctg acctggttgc agttctttca ccatctcgga     420

gctcctatgg acatgtggct gttctacaac taccgaaacg aagccgtttg gatctttgtg     480

ctgctcaacg gcttcattca ctggatcatg tacggctact attggacccg actgatcaag     540

ctcaagttcc ctatgcccaa gtccctgatt acttctatgc agatcattca gttcaacgtt     600

ggcttctaca tcgtctggaa gtaccggaac attccctgct accgacaaga tggaatgaga     660

atgtttggct ggtttttcaa ctacttctac gttggtactg tcctgtgtct gttcctcaac     720

ttctacgtgc agacctacat cgtccgaaag cacaagggag ccaaaaagat tcagtga        777
```

<210> SEQ ID NO 24
<211> LENGTH: 258
<212> TYPE: PRT
<213> ORGANISM: Euglena gracilis
<220> FEATURE:
<221> NAME/KEY: MISC_FEATURE
<222> LOCATION: (1)..(258)
<223> OTHER INFORMATION: delta-9 elongase (EgD9e)

<400> SEQUENCE: 24

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175
```

-continued

```
Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln


<210> SEQ ID NO 25
<211> LENGTH: 828
<212> TYPE: DNA
<213> ORGANISM: Mortierella alpina
<220> FEATURE:
<221> NAME/KEY: CDS
<222> LOCATION: (1)..(828)
<223> OTHER INFORMATION: synthetic C16/18 elongase (codon-optimized)

<400> SEQUENCE: 25

atg gag tct gga ccc atg cct gct ggc att ccc ttc cct gag tac tat       48
Met Glu Ser Gly Pro Met Pro Ala Gly Ile Pro Phe Pro Glu Tyr Tyr
1               5                   10                  15

gac ttc ttt atg gac tgg aag act ccc ctg gcc atc gct gcc acc tac       96
Asp Phe Phe Met Asp Trp Lys Thr Pro Leu Ala Ile Ala Ala Thr Tyr
            20                  25                  30

act gct gcc gtc ggt ctc ttc aac ccc aag gtt ggc aag gtc tcc cga      144
Thr Ala Ala Val Gly Leu Phe Asn Pro Lys Val Gly Lys Val Ser Arg
        35                  40                  45

gtg gtt gcc aag tcg gct aac gca aag cct gcc gag cga acc cag tcc      192
Val Val Ala Lys Ser Ala Asn Ala Lys Pro Ala Glu Arg Thr Gln Ser
    50                  55                  60

gga gct gcc atg act gcc ttc gtc ttt gtg cac aac ctc att ctg tgt      240
Gly Ala Ala Met Thr Ala Phe Val Phe Val His Asn Leu Ile Leu Cys
65                  70                  75                  80

gtc tac tct ggc atc acc ttc tac tac atg ttt cct gct atg gtc aag      288
Val Tyr Ser Gly Ile Thr Phe Tyr Tyr Met Phe Pro Ala Met Val Lys
                85                  90                  95

aac ttc cga acc cac aca ctg cac gaa gcc tac tgc gac acg gat cag      336
Asn Phe Arg Thr His Thr Leu His Glu Ala Tyr Cys Asp Thr Asp Gln
            100                 105                 110

tcc ctc tgg aac aac gca ctt ggc tac tgg ggt tac ctc ttc tac ctg      384
Ser Leu Trp Asn Asn Ala Leu Gly Tyr Trp Gly Tyr Leu Phe Tyr Leu
        115                 120                 125

tcc aag ttc tac gag gtc att gac acc atc atc atc atc ctg aag gga      432
Ser Lys Phe Tyr Glu Val Ile Asp Thr Ile Ile Ile Ile Leu Lys Gly
    130                 135                 140

cga cgg tcc tcg ctg ctt cag acc tac cac cat gct gga gcc atg att      480
Arg Arg Ser Ser Leu Leu Gln Thr Tyr His His Ala Gly Ala Met Ile
145                 150                 155                 160

acc atg tgg tct ggc atc aac tac caa gcc act ccc att tgg atc ttt      528
Thr Met Trp Ser Gly Ile Asn Tyr Gln Ala Thr Pro Ile Trp Ile Phe
                165                 170                 175

gtg gtc ttc aac tcc ttc att cac acc atc atg tac tgt tac tat gcc      576
Val Val Phe Asn Ser Phe Ile His Thr Ile Met Tyr Cys Tyr Tyr Ala
            180                 185                 190

ttc acc tct atc gga ttc cat cct cct ggc aaa aag tac ctg act tcg      624
Phe Thr Ser Ile Gly Phe His Pro Pro Gly Lys Lys Tyr Leu Thr Ser
```

-continued

```
        195                 200                 205

atg cag att act cag ttt ctg gtc ggt atc acc att gcc gtg tcc tac      672
Met Gln Ile Thr Gln Phe Leu Val Gly Ile Thr Ile Ala Val Ser Tyr
    210                 215                 220

ctc ttc gtt cct ggc tgc atc cga aca ccc ggt gct cag atg gct gtc      720
Leu Phe Val Pro Gly Cys Ile Arg Thr Pro Gly Ala Gln Met Ala Val
225                 230                 235                 240

tgg atc aac gtc ggc tac ctg ttt ccc ttg acc tat ctg ttc gtg gac      768
Trp Ile Asn Val Gly Tyr Leu Phe Pro Leu Thr Tyr Leu Phe Val Asp
                245                 250                 255

ttt gcc aag cga acc tac tcc aag cga tct gcc att gcc gct cag aaa      816
Phe Ala Lys Arg Thr Tyr Ser Lys Arg Ser Ala Ile Ala Ala Gln Lys
            260                 265                 270

aag gct cag taa                                                      828
Lys Ala Gln
        275


<210> SEQ ID NO 26
<211> LENGTH: 275
<212> TYPE: PRT
<213> ORGANISM: Mortierella alpina

<400> SEQUENCE: 26

Met Glu Ser Gly Pro Met Pro Ala Gly Ile Pro Phe Pro Glu Tyr Tyr
1               5                   10                  15

Asp Phe Phe Met Asp Trp Lys Thr Pro Leu Ala Ile Ala Ala Thr Tyr
            20                  25                  30

Thr Ala Ala Val Gly Leu Phe Asn Pro Lys Val Gly Lys Val Ser Arg
        35                  40                  45

Val Val Ala Lys Ser Ala Asn Ala Lys Pro Ala Glu Arg Thr Gln Ser
    50                  55                  60

Gly Ala Ala Met Thr Ala Phe Val Phe Val His Asn Leu Ile Leu Cys
65                  70                  75                  80

Val Tyr Ser Gly Ile Thr Phe Tyr Tyr Met Phe Pro Ala Met Val Lys
                85                  90                  95

Asn Phe Arg Thr His Thr Leu His Glu Ala Tyr Cys Asp Thr Asp Gln
            100                 105                 110

Ser Leu Trp Asn Asn Ala Leu Gly Tyr Trp Gly Tyr Leu Phe Tyr Leu
        115                 120                 125

Ser Lys Phe Tyr Glu Val Ile Asp Thr Ile Ile Ile Ile Leu Lys Gly
    130                 135                 140

Arg Arg Ser Ser Leu Leu Gln Thr Tyr His His Ala Gly Ala Met Ile
145                 150                 155                 160

Thr Met Trp Ser Gly Ile Asn Tyr Gln Ala Thr Pro Ile Trp Ile Phe
                165                 170                 175

Val Val Phe Asn Ser Phe Ile His Thr Ile Met Tyr Cys Tyr Tyr Ala
            180                 185                 190

Phe Thr Ser Ile Gly Phe His Pro Pro Gly Lys Lys Tyr Leu Thr Ser
        195                 200                 205

Met Gln Ile Thr Gln Phe Leu Val Gly Ile Thr Ile Ala Val Ser Tyr
    210                 215                 220

Leu Phe Val Pro Gly Cys Ile Arg Thr Pro Gly Ala Gln Met Ala Val
225                 230                 235                 240

Trp Ile Asn Val Gly Tyr Leu Phe Pro Leu Thr Tyr Leu Phe Val Asp
                245                 250                 255

Phe Ala Lys Arg Thr Tyr Ser Lys Arg Ser Ala Ile Ala Ala Gln Lys
```

-continued 260 265 270

Lys Ala Gln
275

<210> SEQ ID NO 27
<211> LENGTH: 8739
<212> TYPE: DNA
<213> ORGANISM: Artificial Sequence
<220> FEATURE:
<223> OTHER INFORMATION: Plasmid pY116

<400> SEQUENCE: 27
ggccgccacc gcggcccgag attccggcct cttcggccgc caagcgaccc gggtggacgt 60
ctagaggtac ctagcaatta acagatagtt tgccggtgat aattctctta acctcccaca 120
ctcctttgac ataacgattt atgtaacgaa actgaaattt gaccagatat tgtgtccgcg 180
gtggagctcc agcttttgtt ccctttagtg agggtttaaa cgagcttggc gtaatcatgg 240
tcatagctgt ttcctgtgtg aaattgttat ccgctcacaa ttccacacaa cgtacgagcc 300
ggaagcataa agtgtaaagc ctggggtgcc taatgagtga gctaactcac attaattgcg 360
ttgcgctcac tgcccgcttt ccagtcggga aacctgtcgt gccagctgca ttaatgaatc 420
ggccaacgcg cggggagagg cggtttgcgt attgggcgct cttccgcttc ctcgctcact 480
gactcgctgc gctcggtcgt tcggctgcgg cgagcggtat cagctcactc aaaggcggta 540
atacggttat ccacagaatc aggggataac gcaggaaaga acatgtgagc aaaaggccag 600
caaaaggcca ggaaccgtaa aaaggccgcg ttgctggcgt ttttccatag gctccgcccc 660
cctgacgagc atcacaaaaa tcgacgctca agtcagaggt ggcgaaaccc gacaggacta 720
taaagatacc aggcgtttcc ccctggaagc tccctcgtgc gctctcctgt tccgaccctg 780
ccgcttaccg gatacctgtc cgcctttctc ccttcgggaa gcgtggcgct ttctcatagc 840
tcacgctgta ggtatctcag ttcggtgtag gtcgttcgct ccaagctggg ctgtgtgcac 900
gaaccccccg ttcagcccga ccgctgcgcc ttatccggta actatcgtct tgagtccaac 960
ccggtaagac acgacttatc gccactggca gcagccactg gtaacaggat tagcagagcg 1020
aggtatgtag gcggtgctac agagttcttg aagtggtggc ctaactacgg ctacactaga 1080
aggacagtat ttggtatctg cgctctgctg aagccagtta ccttcggaaa aagagttggt 1140
agctcttgat ccggcaaaca aaccaccgct ggtagcggtg gtttttttgt ttgcaagcag 1200
cagattacgc gcagaaaaaa aggatctcaa gaagatcctt tgatcttttc tacggggtct 1260
gacgctcagt ggaacgaaaa ctcacgttaa gggattttgg tcatgagatt atcaaaaagg 1320
atcttcacct agatcctttt aaattaaaaa tgaagtttta aatcaatcta aagtatatat 1380
gagtaaactt ggtctgacag ttaccaatgc ttaatcagtg aggcacctat ctcagcgatc 1440
tgtctatttc gttcatccat agttgcctga ctccccgtcg tgtagataac tacgatacgg 1500
gagggcttac catctggccc cagtgctgca atgataccgc gagacccacg ctcaccggct 1560
ccagatttat cagcaataaa ccagccagcc ggaagggccg agcgcagaag tggtcctgca 1620
actttatccg cctccatcca gtctattaat tgttgccggg aagctagagt aagtagttcg 1680
ccagttaata gtttgcgcaa cgttgttgcc attgctacag gcatcgtggt gtcacgctcg 1740
tcgtttggta tggcttcatt cagctccggt tcccaacgat caaggcgagt tacatgatcc 1800
cccatgttgt gcaaaaaagc ggttagctcc ttcggtcctc cgatcgttgt cagaagtaag 1860
ttggccgcag tgttatcact catggttatg gcagcactgc ataattctct tactgtcatg 1920

-continued

```
ccatccgtaa gatgcttttc tgtgactggt gagtactcaa ccaagtcatt ctgagaatag   1980
tgtatgcggc gaccgagttg ctcttgcccg gcgtcaatac gggataatac cgcgccacat   2040
agcagaactt taaaagtgct catcattgga aaacgttctt cggggcgaaa actctcaagg   2100
atcttaccgc tgttgagatc cagttcgatg taacccactc gtgcacccaa ctgatcttca   2160
gcatctttta ctttcaccag cgtttctggg tgagcaaaaa caggaaggca aaatgccgca   2220
aaaaagggaa taagggcgac acggaaatgt tgaatactca tactcttcct ttttcaatat   2280
tattgaagca tttatcaggg ttattgtctc atgagcggat acatatttga atgtatttag   2340
aaaaataaac aaataggggt tccgcgcaca tttccccgaa aagtgccacc tgacgcgccc   2400
tgtagcggcg cattaagcgc ggcgggtgtg gtggttacgc gcagcgtgac cgctacactt   2460
gccagcgccc tagcgcccgc tcctttcgct ttcttccctt cctttctcgc cacgttcgcc   2520
ggctttcccc gtcaagctct aaatcggggg ctccctttag ggttccgatt tagtgcttta   2580
cggcacctcg accccaaaaa acttgattag ggtgatggtt cacgtagtgg gccatcgccc   2640
tgatagacgg tttttcgccc tttgacgttg gagtccacgt tctttaatag tggactcttg   2700
ttccaaactg gaacaacact caaccctatc tcggtctatt cttttgattt ataagggatt   2760
ttgccgattt cggcctattg gttaaaaaat gagctgattt aacaaaaatt taacgcgaat   2820
tttaacaaaa tattaacgct tacaatttcc attcgccatt caggctgcgc aactgttggg   2880
aagggcgatc ggtgcgggcc tcttcgctat tacgccagct ggcgaaaggg ggatgtgctg   2940
caaggcgatt aagttgggta acgccagggt tttcccagtc acgacgttgt aaaacgacgg   3000
ccagtgaatt gtaatacgac tcactatagg gcgaattggg taccgggccc cccctcgagg   3060
tcgatggtgt cgataagctt gatatcgaat tcatgtcaca caaaccgatc ttcgcctcaa   3120
ggaaacctaa ttctacatcc gagagactgc cgagatccag tctacactga ttaattttcg   3180
ggccaataat ttaaaaaaat cgtgttatat aatattatat gtattatata tatacatcat   3240
gatgatactg acagtcatgt cccattgcta aatagacaga ctccatctgc cgcctccaac   3300
tgatgttctc aatatttaag ggtcatctc gcattgttta ataataaaca gactccatct   3360
accgcctcca aatgatgttc tcaaaatata ttgtatgaac ttatttttat tacttagtat   3420
tattagacaa cttacttgct ttatgaaaaa cacttcctat ttaggaaaca atttataatg   3480
gcagttcgtt catttaacaa tttatgtaga ataaatgtta taaatgcgta tgggaaatct   3540
taaatatgga tagcataaat gatatctgca ttgcctaatt cgaaatcaac agcaacgaaa   3600
aaaatccctt gtacaacata aatagtcatc gagaaatatc aactatcaaa gaacagctat   3660
tcacacgtta ctattgagat tattattgga cgagaatcac acactcaact gtctttctct   3720
cttctagaaa tacaggtaca agtatgtact attctcattg ttcatacttc tagtcatttc   3780
atcccacata ttccttggat ttctctccaa tgaatgacat tctatcttgc aaattcaaca   3840
attataataa gatataccaa agtagcggta tagtggcaat caaaaagctt ctctggtgtg   3900
cttctcgtat ttatttttat tctaatgatc cattaaaggt atatatttat ttcttgttat   3960
ataatccttt tgtttattac atgggctgga tacataaagg tattttgatt taattttttg   4020
cttaaattca atcccccctc gttcagtgtc aactgtaatg gtaggaaatt accatacttt   4080
tgaagaagca aaaaaaatga aagaaaaaaa aaatcgtatt tccaggttag acgttccgca   4140
gaatctagaa tgcggtatgc ggtacattgt tcttcgaacg taaaagttgc gctccctgag   4200
atattgtaca tttttgcttt tacaagtaca agtacatcgt acaactatgt actactgttg   4260
atgcatccac aacagtttgt tttgtttttt tttgtttttt ttttttctaa tgattcatta   4320
```

-continued

```
ccgctatgta tacctacttg tacttgtagt aagccgggtt attggcgttc aattaatcat   4380
agacttatga atctgcacgg tgtgcgctgc gagttacttt tagcttatgc atgctacttg   4440
ggtgtaatat tgggatctgt tcggaaatca acggatgctc aaccgatttc gacagtaatt   4500
aattaatttg aatcgaatcg gagcctaaaa tgaacccgag tatatctcat aaaattctcg   4560
gtgagaggtc tgtgactgtc agtacaaggt gccttcatta tgccctcaac cttaccatac   4620
ctcactgaat gtagtgtacc tctaaaaatg aaatacagtg ccaaaagcca aggcactgag   4680
ctcgtctaac ggacttgata tacaaccaat taaaacaaat gaaaagaaat acagttcttt   4740
gtatcatttg taacaattac cctgtacaaa ctaaggtatt gaaatcccac aatattccca   4800
aagtccaccc ctttccaaat tgtcatgcct acaactcata taccaagcac taacctacca   4860
aacaccacta aaaccccaca aaatatatct taccgaatat acagtaacaa gctaccacca   4920
cactcgttgg gtgcagtcgc cagcttaaag atatctatcc acatcagcca caactccctt   4980
cctttaataa accgactaca cccttggcta ttgaggttat gagtgaatat actgtagaca   5040
agacactttc aagaagactg tttccaaaac gtaccactgt cctccactac aaacacaccc   5100
aatctgcttc ttctagtcaa ggttgctaca ccggtaaatt ataaatcatc atttcattag   5160
cagggcaggg cccttttttat agagtcttat acactagcgg accctgccgg tagaccaacc   5220
cgcaggcgcg tcagtttgct ccttccatca atgcgtcgta gaaacgactt actccttctt   5280
gagcagctcc ttgaccttgt tggcaacaag tctccgacct cggaggtgga ggaagagcct   5340
ccgatatcgg cggtagtgat accagcctcg acggactcct tgacggcagc ctcaacagcg   5400
tcaccggcgg gcttcatgtt aagagagaac ttgagcatca tggcggcaga cagaatggtg   5460
gcaatggggt tgaccttctg cttgccgaga tcgggggcag atccgtgaca gggctcgtac   5520
agaccgaacg cctcgttggt gtcgggcaga gaagccagag aggcggaggg cagcagaccc   5580
agagaaccgg ggatgacgga ggcctcgtcg gagatgatat cgccaaacat gttggtggtg   5640
atgatgatac cattcatctt ggagggctgc ttgatgagga tcatggcggc cgagtcgatc   5700
agctggtggt tgagctcgag ctgggggaat tcgtccttga ggactcgagt gacagtcttt   5760
cgccaaagtc gagaggaggc cagcacgttg gccttgtcaa gagaccacac gggaagaggg   5820
gggttgtgct gaagggccag gaaggcggcc attcgggcaa ttcgctcaac ctcaggaacg   5880
gagtaggtct cggtgtcgga agcgacgcca gatccgtcat cctcctttcg ctctccaaag   5940
tagatacctc cgacgagctc tcggacaatg atgaagtcgg tgccctcaac gtttcggatg   6000
ggggagagat cggcgagctt gggcgacagc agctggcagg gtcgcaggtt ggcgtacagg   6060
ttcaggtcct ttcgcagctt gaggagaccc tgctcgggtc gcacgtcggt tcgtccgtcg   6120
ggagtggtcc atacggtgtt ggcagcgcct ccgacagcac cgagcataat agagtcagcc   6180
tttcggcaga tgtcgagagt agcgtcggtg atgggctcgc cctccttctc aatggcagct   6240
cctccaatga gtcggtcctc aaacacaaac tcggtgccgg aggcctcagc aacagacttg   6300
agcaccttga cggcctcggc aatcacctcg gggccacaga agtcgccgcc gagaagaaca   6360
atcttcttgg agtcagtctt ggtcttctta gtttcgggtt ccattgtgga tgtgtgtggt   6420
tgtatgtgtg atgtggtgtg tggagtgaaa atctgtggct ggcaaacgct cttgtatata   6480
tacgcacttt tgcccgtgct atgtggaaga ctaaacctcc gaagattgtg actcaggtag   6540
tgcggtatcg gctagggacc caaaccttgt cgatgccgat agcgctatcg aacgtacccc   6600
agccggccgg gagtatgtcg gaggggacat acgagatcgt caagggtttg tggccaactg   6660
```

-continued gtatttaaat gtagctaacg gtagcaggcg aactactggt acatacctcc cccggaatat 6720
gtacaggcat aatgcgtatc tgtgggacat gtggtcgttg cgccattatg taagcagcgt 6780
gtactcctct gactgtccat atggtttgct ccatctcacc ctcatcgttt tcattgttca 6840
caggcggcca caaaaaaact gtcttctctc cttctctctt cgccttagtc tactcggacc 6900
agttttagtt tagcttggcg ccactggata aatgagacct caggccttgt gatgaggagg 6960
tcacttatga agcatgttag gaggtgcttg tatggataga gaagcaccca aaataataag 7020
aataataata aaacaggggg cgttgtcatt tcatatcgtg ttttcaccat caatacacct 7080
ccaaacaatg cccttcatgt ggccagcccc aatattgtcc tgtagttcaa ctctatgcag 7140
ctcgtatctt attgagcaag taaaactctg tcagccgata ttgcccgacc cgcgacaagg 7200
gtcaacaagg tggtgtaagg ccttcgcaga agtcaaaact gtgccaaaca aacatctaga 7260
gtctctttgg tgtttctcgc atatatttwa tcggctgtct tacgtatttg cgcctcggta 7320
ccggactaat ttcggatcat ccccaatacg ctttttcttc gcagctgtca acagtgtcca 7380
tgatctatcc acctaaatgg gtcatatgag gcgtataatt tcgtggtgct gataataatt 7440
cccatatatt tgacacaaaa cttccccccc tagacataca tctcacaatc tcacttcttg 7500
tgcttctgtc acacatctcc tccagctgac ttcaactcac acctctgccc cagttggtct 7560
acagcggtat aaggtttctc cgcatagagg tgcaccactc ctcccgatac ttgtttgtgt 7620
gacttgtggg tcacgacata tatatctaca cacattgcgc caccctttgg ttcttccagc 7680
acaacaaaaa cacgacacgc taaccatggc caatttactg accgtacacc aaaatttgcc 7740
tgcattaccg gtcgatgcaa cgagtgatga ggttcgcaag aacctgatgg acatgttcag 7800
ggatcgccag gcgttttctg agcatacctg gaaaatgctt ctgtccgttt gccggtcgtg 7860
ggcggcatgg tgcaagttga ataaccggaa atggtttccc gcagaacctg aagatgttcg 7920
cgattatctt ctatatcttc aggcgcgcgg tctggcagta aaaactatcc agcaacattt 7980
gggccagcta aacatgcttc atcgtcggtc cgggctgcca cgaccaagtg acagcaatgc 8040
tgtttcactg gttatgcggc ggatccgaaa agaaaacgtt gatgccggtg aacgtgcaaa 8100
acaggctcta gcgttcgaac gcactgattt cgaccaggtt cgttcactca tggaaaatag 8160
cgatcgctgc caggatatac gtaatctggc atttctgggg attgcttata acaccctgtt 8220
acgtatagcc gaaattgcca ggatcagggt taaagatatc tcacgtactg acggtgggag 8280
aatgttaatc catattggca gaacgaaaac gctggttagc accgcaggtg tagagaaggc 8340
acttagcctg ggggtaacta aactggtcga gcgatggatt tccgtctctg gtgtagctga 8400
tgatccgaat aactacctgt tttgccgggt cagaaaaaat ggtgttgccg cgccatctgc 8460
caccagccag ctatcaactc gcgccctgga agggattttt gaagcaactc atcgattgat 8520
ttacggcgct aaggatgact ctggtcagag atacctggcc tggtctggac acagtgcccg 8580
tgtcggagcc gcgcgagata tggcccgcgc tggagtttca ataccggaga tcatgcaagc 8640
tggtggctgg accaatgtaa atattgtcat gaactatatc cgtaacctgg atagtgaaac 8700
aggggcaatg gtgcgcctgc tggaagatgg cgattaagc 8739

<210> SEQ ID NO 28
<211> LENGTH: 15304
<212> TYPE: DNA
<213> ORGANISM: Artificial Sequence
<220> FEATURE:
<223> OTHER INFORMATION: Plasmid pKO2UF8289
<220> FEATURE:
<221> NAME/KEY: misc_feature -continued
<222> LOCATION: (5601)..(5601)
<223> OTHER INFORMATION: n is a, c, g, or t
<220> FEATURE:
<221> NAME/KEY: misc_feature
<222> LOCATION: (5606)..(5609)
<223> OTHER INFORMATION: n is a, c, g, or t

<400> SEQUENCE: 28
cgatcgagga agaggacaag cggctgcttc ttaagtttgt gacatcagta tccaaggcac 60
cattgcaagg attcaaggct ttgaacccgt catttgccat tcgtaacgct ggtagacagg 120
ttgatcggtt ccctacggcc tccacctgtg tcaatcttct caagctgcct gactatcagg 180
acattgatca acttcggaag aaacttttgt atgccattcg atcacatgct ggtttcgatt 240
tgtcttagag gaacgcatat acagtaatca tagagaataa acgatattca tttattaaag 300
tagatagttg aggtagaagt tgtaaagagt gataaatagc ggccgctcac tgaatctttt 360
tggctccctt gtgcttcctg acgatatacg tttgcacata gaaattcaag aacaaacaca 420
agactgtgcc aacataaaag taattgaaga accagccaaa catcctcatc ccatcttggc 480
gataacaggg aatgttcctg tacttccaga caatgtagaa accaacattg aattgaatga 540
tctgcattga tgtaatcagg gattttggca tggggaactt cagcttgatc aatctggtcc 600
aataataacc gtacatgatc cagtggatga aaccattcaa cagcacaaaa atccaaacag 660
cttcatttcg gtaattatag aacagccaca tatccatcgg tgcccccaaa tgatggaaga 720
attgcaacca ggtcagaggc ttgcccatca gtggcaaata gaaggagtca atatactcca 780
ggaacttgct caaatagaac aactgcgtgg tgatcctgaa gacgttgttg tcaaaagcct 840
tctcgcagtt gtcagacata acaccgatgg tgtacatggc atatgccatt gagaggaatg 900
atcccaacga ataaatggac atgagaaggt tgtaattggt gaaaacaaac ttcatacgag 960
actgaccttt tggaccaagg gggccaagag tgaacttcaa gatgacaaat gcgatggaca 1020
agtaaagcac ctcacagtga ctggcatcac tccagagttg ggcataatca actggttggg 1080
taaaacttcc tgcccaattg agactatttc attcaccacc tccatggtta gcgtgtcgtg 1140
tttttgttgt gctggaagaa ccaaagggtg gcgcaatgtg tgtagatata tatgtcgtga 1200
cccacaagtc acacaaacaa gtatcgggag gagtggtgca cctctatgcg gagaaacctt 1260
ataccgctgt agaccaactg gggcagaggt gtgagttgaa gtcagctgga ggagatgtgt 1320
gacagaagca caagaagtga gattgtgaga tgtatgtcta gggggggaag ttttgtgtca 1380
aatatatggg aattattatc agcaccacga aattatacgc ctcatatgac ccatttaggt 1440
ggatagatca tggacactgt tgacagctgc gaagaaaaag cgtattgggg atgatccgaa 1500
attagtccgg taccgaggcg caaatacgta agacagccga twaaatatat gcgagaaaca 1560
ccaaagagac tctagatgtt tgtttggcac agttttgact tctgcgaagg ccttacacca 1620
ccttgttgac ccttgtcgcg ggtcgggcaa tatcggctga cagagtttta cttgctcaat 1680
aagatacgag ctgcatagag ttgaactaca ggacaatatt ggggctggcc acatgaaggg 1740
cattgtttgg aggtgtattg atggtgaaaa cacgatatga aatgacaacg ccccctgttt 1800
tattattatt cttattattt tgggtgcttc tctatccata caagcacctc ctaacatgct 1860
tcataagtga cctcctcatc acaaggcctg aggtctcatt tatccagtgg cgccaagcta 1920
aactaaaact ggtccgagta gactaaggcg aagagagaag gagagaagac agttttttg 1980 tggccgcctg tgaacaatga aaacgatgag ggtgagatgg agcaaaccat atggtttaaa 2040
cagtcagagg agtacacgct gcttacataa tggcgcaacg accacatgtc ccacagatac 2100

-continued

```
gcatcgattc gattcaaatt aattaaaagg cgttgaaaca gaatgagcca gacagcaagg   2160

acaaggtggc caacagcaag gagtccaaaa agccctctat tgacgagatc cacgatgtta   2220

ttgctcatga ggtttccgag ctcgatgctg ggaagaagaa gtgatttgta tataagaaat   2280

aaatgagata tagtaaagga gtgcaagaga atggcaaggt ggtcaaattc tatattactt   2340

gcagtcactg gttcctcgtt gacatgaatg aagttaccgt tggcatagct gatttaatat   2400

ataactgtcc aactaactct cacctagata taacccatgt gtgtgtttcc aatcatcaat   2460

gcggccgctt actgagcctt ggcaccgggc tgcttctcgg ccattcgagc gaactgggac   2520

aggtatcgga gcaggatgac gagaccttca tggggcagag ggtttcggta ggggaggttg   2580

tgcttctggc acagctgttc cacctggtag gaaacggcag tgaggttgtg tcgaggcagg   2640

gtgggccaga gatggtgctc gatctggtag ttcaggcctc caaagaacca gtcagtaatg   2700

atgcctcgtc gaatgttcat ggtctcatgg atctgaccca cagagaagcc atgtccgtcc   2760

cagacggaat caccgatctt ctccagaggg tagtggttca tgaagaccac gatggcaatt   2820

ccgaagccac cgacgagctc ggaaacaaag aacaccagca tcgaggtcag gatggagggc   2880

ataaagaaga ggtggaacag ggtcttgaga gtccagtgca gagcgagtcc aatggcctct   2940

ttcttgtact gagatcggta gaactggttg tctcggtcct tgagggatcg aacggtcagc   3000

acagactgga aacaccagat gaatcgcagg agaatacaga tgaccaggaa atagtactgt   3060

tggaactgaa tgagctttcg ggagatggga gaagctcgag tgacatcgtc ctcggaccag   3120

gcgagcagag gcaggttatc aatgtcggga tcgtgaccct gaacgttggt agcagaatga   3180

tgggcgttgt gtctgtcctt ccaccaggtc acggagaagc cctggagtcc gttgccaaag   3240

accagaccca ggacgttatt ccagtttcgg ttcttgaagg tctggtggtg gcagatgtca   3300

tgagacagcc atcccatttg ctggtagtgc ataccgagca cgagagcacc aatgaagtac   3360

aggtggtact ggaccagcat gaagaaggca agcacgccaa gacccagggt ggtcaagatc   3420

ttgtacgagt accagagggg agaggcgtca aacatgccag tggcgatcag ctcttctcgg   3480

agctttcgga aatcctcctg agcttcgttg acggcagcct ggggaggcag ctcggaagcc   3540

tggttgatct tgggcattcg cttgagcttg tcgaaggctt cctgagagtg cataaccatg   3600

aaggcgtcag tagcatctcg tccctggtag ttctcaatga tttcagctcc accagggtgg   3660

aagttcaccc aagcggagac gtcgtacacc tttccgtcga tgacgagggg cagagcctgt   3720

cgagaagcct tcaccatggc cattgctgta gatatgtctt gtgtgtaagg gggttggggt   3780

ggttgtttgt gttcttgact tttgtgttag caagggaaga cgggcaaaaa agtgagtgtg   3840

gttgggaggg agagacgagc cttatatata atgcttgttt gtgtttgtgc aagtggacgc   3900

cgaaacgggc aggagccaaa ctaaacaagg cagacaatgc gagcttaatt ggattgcctg   3960

atgggcaggg gttagggctc gatcaatggg ggtgcgaagt gacaaaattg ggaattaggt   4020

tcgcaagcaa ggctgacaag actttggccc aaacatttgt acgcggtgga caacaggagc   4080

cacccatcgt ctgtcacggg ctagccggtc gtgcgtcctg tcaggctcca cctaggctcc   4140

atgccactcc atacaatccc actagtgtac cgctaggccg cttttagctc ccatctaaga   4200

cccccccaaa acctccactg tacagtgcac tgtactgtgt ggcgatcaag ggcaagggaa   4260

aaaaggcgca aacatgcacg catggaatga cgtaggtaag gcgttactag actgaaaagt   4320

ggcacatttc ggcgtgccaa agggtcctag gtgcgtttcg cgagctgggc gccaggccaa   4380

gccgctccaa aacgcctctc cgactccctc cagcggcctc catatcccca tccctctcca   4440

cagcaatgtt gttaagcctt gcaaacgaaa aaatagaaag gctaataagc ttccaatatt   4500
```

-continued

```
gtggtgtacg ctgcataacg caacaatgag cgccaaacaa cacacacaca cagcacacag   4560
cagcattaac cacgatgttt aaacagtgta cgcagatccc gtcaacagtt ttatatatcg   4620
tagttacaac catcaacact ttttggtaag tgtaccattc tatactccaa ctggtctgca   4680
actgtacaag tagacatgtt aatggtagtt aataacatct acagcagaac ctatggtaaa   4740
gacattgcat ttttacagga agtatcgtcc tacacgttga taaatccaaa gatgcggaac   4800
ttcttccact tttatcatca tcccctactc gtacactcgt actctttgtt cgatcgcgat   4860
tcatttctat aaataatctt gtatgtacat gcggccgcgc ctacttaagc aacgggcttg   4920
ataacagcgg ggggggtgcc cacgttgttg cggttgcgga agaacagaac acccttacca   4980
gcaccctcgg caccagcgct gggctcaacc cactggcaca tacgcgcact gcggtacatg   5040
gcgcggatga agccacgagg accatcctgg acatcagccc ggtagtgctt gcccatgatg   5100
ggcttaatgg cctcggtggc ctcgtccgcg ttgtagaagg ggatgctgct gacgtagtgg   5160
tggaggacat gagtctcgat gatgccgtgg agaaggtggc ggccgatgaa gcccatctca   5220
cggtcaatgg tagcagcggc accacggacg aagttccact cgtcgttggt gtagtgggga   5280
agggtagggt cggtgtgctg gaggaaggtg atggcaacga gccagtggtt aacccagagg   5340
tagggaacaa agtaccagat ggccatgttg tagaaaccga acttctgaac gaggaagtac   5400
agagcagtgg ccatcagacc gataccaata tcgctgagga cgatgagctt agcgtcactg   5460
ttctcgtaca gagggctgcg gggatcgaag tggttaacac caccgccgag gccgttatgc   5520
ttgcccttgc cgcgaccctc acgctggcgc tcgtggtagt tgtggccggt aacattggtg   5580
atgaggtagt tgggccagcc nacgannnnc tcagtaagat gagcgagctc gtgggtcatc   5640
tttccgagac gagtagcctg ctgctcgcgg gttcggggaa cgaagaccat gtcacgctcc   5700
atgttgccag tggccttgtg gtgctttcgg tgggagattt gccagctgaa gtaggggaca   5760
aggagggaag agtgaagaac ccagccagta atgtcgttga tgatgcgaga atcggagaaa   5820
gcaccgtgac cgcactcatg ggcaataacc cagagaccag taccgaaaag accctgaaga   5880
acggtgtaca cggcccacag accagcgcgg gcgggggtgg aggggatata ttcgggggtc   5940
acaaagttgt accagatgct gaaagtggta gtcaggagga caatgtcgcg gaggatataa   6000
ccgtatccct tgagagcgga gcgcttgaag cagtgcttag ggatggcatt gtagatgtcc   6060
ttgatggtaa agtcgggaac ctcgaactgg ttgccgtagg tgtcgagcat gacaccatac   6120
tcggacttgg gcttggcgat atcaacctcg gacatggacg agagcgatgt ggaagaggcc   6180
gagtggcggg gagagtctga aggagagacg gcggcagact cagaatccgt cacagtagtt   6240
gaggtgacgg tgcgtctaag cgcagggttc tgcttgggca gagccgaagt ggacgccatg   6300
gttgtgaatt agggtggtga gaatggttgg ttgtagggaa gaatcaaagg ccggtctcgg   6360
gatccgtggg tatatatata tatatatata tatacgatcc ttcgttacct ccctgttctc   6420
aaaactgtgg tttttcgttt ttcgtttttt gctttttttg atttttttag ggccaactaa   6480
gcttccagat ttcgctaatc acctttgtac taattacaag aaaggaagaa gctgattaga   6540
gttgggcttt ttatgcaact gtgctactcc ttatctctga tatgaaagtg tagacccaat   6600
cacatcatgt catttagagt tggtaatact gggaggatag ataaggcacg aaaacgagcc   6660
atagcagaca tgctgggtgt agccaagcag aagaaagtag atgggagcca attgacgagc   6720
gagggagcta cgccaatccg acatacgaca cgctgagatc gtcttggccg gggggtacct   6780
acagatgtcc aagggtaagt gcttgactgt aattgtatgt ctgaggacaa atatgtagtc   6840
```

-continued

```
agccgtataa agtcatacca ggcaccagtg ccatcatcga accactaact ctctatgata   6900
catgcctccg gtattattgt accatgcgtc gctttgttac atacgtatct tgcctttttc   6960
tctcagaaac tccagacttt ggctattggt cgagataagc ccggaccata gtgagtcttt   7020
cacactctac atttctccct tgctccaact atttaaattg ccccggagaa gacggccagg   7080
ccgcctagat gacaaattca acaactcaca gctgactttc tgccattgcc actagggggg   7140
ggcctttta tatggccaag ccaagctctc cacgtcggtt gggctgcacc caacaataaa   7200
tgggtagggt tgcaccaaca aagggatggg atgggggta gaagatacga ggataacggg   7260
gctcaatggc acaaataaga acgaatactg ccattaagac tcgtgatcca gcgactgaca   7320
ccattgcatc atctaagggc ctcaaaacta cctcggaact gctgcgctga tctggacacc   7380
acagaggttc cgagcacttt aggttgcacc aaatgtccca ccaggtgcag gcagaaaacg   7440
ctggaacagc gtgtacagtt tgtcttaaca aaaagtgagg gcgctgaggt cgagcagggt   7500
ggtgtgactt gttatagcct ttagagctgc gaaagcgcgt atggatttgg ctcatcaggc   7560
cagattgagg gtctgtggac acatgtcatg ttagtgtact tcaatcgccc cctggatata   7620
gccccgacaa taggccgtgg cctcattttt ttgccttccg cacatttcca ttgctcggta   7680
cccacacctt gcttctcctg cacttgccaa ccttaatact ggtttacatt gaccaacatc   7740
ttacaagcgg ggggcttgtc tagggtatat ataaacagtg gctctcccaa tcggttgcca   7800
gtctcttttt tcctttcttt ccccacagat tcgaaatcta aactacacat cacagaattc   7860
cgagccgtga gtatccacga caagatcagt gtcgagacga cgcgttttgt gtaatgacac   7920
aatccgaaag tcgctagcaa cacacactct ctacacaaac taacccagct ctggtaccat   7980
ggtgaaggct tctcgacagg ctctgcccct cgtcatcgac ggaaaggtgt acgacgtctc   8040
cgcttgggtg aacttccacc ctggtggagc tgaaatcatt gagaactacc agggacgaga   8100
tgctactgac gccttcatgg ttatgcactc tcaggaagcc ttcgacaagc tcaagcgaat   8160
gcccaagatc aaccaggctt ccgagctgcc tccccaggct gccgtcaacg aagctcagga   8220
ggatttccga aagctccgag aagagctgat cgccactggc atgtttgacg cctctcccct   8280
ctggtactcg tacaagatct tgaccaccct gggtcttggc gtgcttgcct tcttcatgct   8340
ggtccagtac cacctgtact tcattggtgc tctcgtgctc ggtatgcact accagcaaat   8400
gggatggctg tctcatgaca tctgccacca ccagaccttc aagaaccgaa actggaataa   8460
cgtcctgggt ctggtctttg gcaacggact ccagggcttc tccgtgacct ggtggaagga   8520
cagacacaac gcccatcatt ctgctaccaa cgttcagggt cacgatcccg acattgataa   8580
cctgcctctg ctcgcctggt ccgaggacga tgtcactcga gcttctccca tctcccgaaa   8640
gctcattcag ttccaacagt actatttcct ggtcatctgt attctcctgc gattcatctg   8700
gtgtttccag tctgtgctga ccgttcgatc cctcaaggac cgagacaacc agttctaccg   8760
atctcagtac aagaaagagg ccattggact cgctctgcac tggactctca agaccctgtt   8820
ccacctcttc tttatgccct ccatcctgac ctcgatgctg gtgttctttg tttccgagct   8880
cgtcggtggc ttcggaattg ccatcgtggt cttcatgaac cactaccctc tggagaagat   8940
cggtgattcc gtctgggacg gacatggctt ctctgtgggt cagatccatg agaccatgaa   9000
cattcgacga ggcatcatta ctgactggtt ctttggaggc ctgaactacc agatcgagca   9060
ccatctctgg cccaccctgc ctcgacacaa cctcactgcc gtttcctacc aggtggaaca   9120
gctgtgccag aagcacaacc tcccctaccg aaaccctctg ccccatgaag gtctcgtcat   9180
cctgctccga tacctgtccc agttcgctcg aatggccgag aagcagcccg gtgccaaggc   9240
```

-continued

```
tcagtaagcg gccgcaagtg tggatgggga agtgagtgcc cggttctgtg tgcacaattg   9300
gcaatccaag atggatggat tcaacacagg gatatagcga gctacgtggt ggtgcgagga   9360
tatagcaacg gatatttatg tttgacactt gagaatgtac gatacaagca ctgtccaagt   9420
acaatactaa acatactgta catactcata ctcgtacccg ggcaacggtt tcacttgagt   9480
gcagtggcta gtgctcttac tcgtacagtg tgcaatactg cgtatcatag tctttgatgt   9540
atatcgtatt cattcatgtt agttgcgtac gggtgaagct tccactggtc ggcgtggtag   9600
tggggcagag tggggtcggt gtgctgcagg taggtgatgg ccacgagcca gtggttgacc   9660
cacaggtagg ggatcaggta gtagagggtg acggaagcca ggccccatcg gttgatggag   9720
tatgcgatga cggacatggt gataccaata ccgacgttag agatccagat gttgaaccag   9780
tccttcttct caaacagcgg ggcgttgggg ttgaagtggt tgacagccca tttgttgagc   9840
ttggggtact tctgtccggt aacgtaagac agcagataca gaggccatcc aaacacctgc   9900
tgggtgatga ggccgtagag ggtcatgagg ggagcgtcct cagcaagctc agaccagtca   9960
tgggcgcctc ggttctccat aaactccttt cggtccttgg gcacaaacac catatcacgg  10020
gtgaggtgac cagtggactt gtggtgcatg gagtgggtca gcttccaggc gtagtaaggg  10080
accagcatgg aggagtgcag aacccatccg gtgacgttgt tgacggtgtt agagtcggag  10140
aaagcagagt ggccacactc gtgggcaaga acccacagac cggtgccaaa cagaccctgg  10200
acaatggagt acatggccca ggccacagct cggccggaag ccgagggaat aagaggcagg  10260
tacgcgtagg ccatgtaggc aaaaacggcg ataaagaagc aggcgcgcca gctgcattaa  10320
tgaatcggcc aacgcgcggg gagaggcggt ttgcgtattg ggcgctcttc cgcttcctcg  10380
ctcactgact cgctgcgctc ggtcgttcgg ctgcggcgag cggtatcagc tcactcaaag  10440
gcggtaatac ggttatccac agaatcaggg gataacgcag gaaagaacat gtgagcaaaa  10500
ggccagcaaa aggccaggaa ccgtaaaaag gccgcgttgc tggcgttttt ccataggctc  10560
cgcccccctg acgagcatca caaaaatcga cgctcaagtc agaggtggcg aaacccgaca  10620
ggactataaa gataccaggc gtttccccct ggaagctccc tcgtgcgctc tcctgttccg  10680
accctgccgc ttaccggata cctgtccgcc tttctccctt cgggaagcgt ggcgctttct  10740
catagctcac gctgtaggta tctcagttcg gtgtaggtcg ttcgctccaa gctgggctgt  10800
gtgcacgaac cccccgttca gcccgaccgc tgcgccttat ccggtaacta tcgtcttgag  10860
tccaacccgg taagacacga cttatcgcca ctggcagcag ccactggtaa caggattagc  10920
agagcgaggt atgtaggcgg tgctacagag ttcttgaagt ggtggcctaa ctacggctac  10980
actagaagaa cagtatttgg tatctgcgct ctgctgaagc cagttacctt cggaaaaaga  11040
gttggtagct cttgatccgg caaacaaacc accgctggta gcggtggttt ttttgtttgc  11100
aagcagcaga ttacgcgcag aaaaaaagga tctcaagaag atcctttgat cttttctacg  11160
gggtctgacg ctcagtggaa cgaaaactca cgttaaggga ttttggtcat gagattatca  11220
aaaaggatct tcacctagat ccttttaaat taaaaatgaa gttttaaatc aatctaaagt  11280
atatatgagt aaacttggtc tgacagttac caatgcttaa tcagtgaggc acctatctca  11340
gcgatctgtc tatttcgttc atccatagtt gcctgactcc ccgtcgtgta gataactacg  11400
atacgggagg gcttaccatc tggccccagt gctgcaatga taccgcgaga cccacgctca  11460
ccggctccag atttatcagc aataaaccag ccagccggaa gggccgagcg cagaagtggt  11520
cctgcaactt tatccgcctc catccagtct attaattgtt gccgggaagc tagagtaagt  11580
```

-continued

```
agttcgccag ttaatagttt gcgcaacgtt gttgccattg ctacaggcat cgtggtgtca  11640
cgctcgtcgt ttggtatggc ttcattcagc tccggttccc aacgatcaag gcgagttaca  11700
tgatccccca tgttgtgcaa aaaagcggtt agctccttcg gtcctccgat cgttgtcaga  11760
agtaagttgg ccgcagtgtt atcactcatg gttatggcag cactgcataa ttctcttact  11820
gtcatgccat ccgtaagatg cttttctgtg actggtgagt actcaaccaa gtcattctga  11880
gaatagtgta tgcggcgacc gagttgctct tgcccggcgt caatacggga taataccgcg  11940
ccacatagca gaactttaaa agtgctcatc attggaaaac gttcttcggg gcgaaaactc  12000
tcaaggatct taccgctgtt gagatccagt tcgatgtaac ccactcgtgc acccaactga  12060
tcttcagcat cttttacttt caccagcgtt tctgggtgag caaaaacagg aaggcaaaat  12120
gccgcaaaaa agggaataag ggcgacacgg aaatgttgaa tactcatact cttccttttt  12180
caatattatt gaagcattta tcagggttat tgtctcatga gcggatacat atttgaatgt  12240
atttagaaaa ataaacaaat aggggttccg cgcacatttc cccgaaaagt gccacctgat  12300
gcggtgtgaa ataccgcaca gatgcgtaag gagaaaatac cgcatcagga aattgtaagc  12360
gttaatattt tgttaaaatt cgcgttaaat ttttgttaaa tcagctcatt ttttaaccaa  12420
taggccgaaa tcggcaaaat cccttataaa tcaaaagaat agaccgagat agggttgagt  12480
gttgttccag tttggaacaa gagtccacta ttaaagaacg tggactccaa cgtcaaaggg  12540
cgaaaaaccg tctatcaggg cgatggccca ctacgtgaac catcacccta atcaagtttt  12600
ttggggtcga ggtgccgtaa agcactaaat cggaacccta aagggagccc ccgatttaga  12660
gcttgacggg gaaagccggc gaacgtggcg agaaaggaag ggaagaaagc gaaaggagcg  12720
ggcgctaggg cgctggcaag tgtagcggtc acgctgcgcg taaccaccac acccgccgcg  12780
cttaatgcgc cgctacaggg cgcgtccatt cgccattcag gctgcgcaac tgttgggaag  12840
ggcgatcggt gcgggcctct tcgctattac gccagctggc gaaaggggga tgtgctgcaa  12900
ggcgattaag ttgggtaacg ccagggtttt cccagtcacg acgttgtaaa acgacggcca  12960
gtgaattgta atacgactca ctatagggcg aattgggccc gacgtcgcat gcttgaatct  13020
acaagtagga gggttggagt gattaagtga aacttcttta acggctctat gccagttcta  13080
ttgatatccg aaacatcagt atgaaggtct gataagggtg acttcttccc acagattcgt  13140
atcagtacga gtacgagacc ggtacttgta acagtattga tactaaaggg aaactacaac  13200
ggttgtcagc gtaatgtgac ttcgcccatg aacgcagaca cgcagtgccg agtgcggtga  13260
tatcgcctac tcgttacgtc catggactac acaacccctc ggcttcgctt ggcttagcct  13320
cgggctcggt gctgttcagt taaaacacaa tcaaataaca tttctacttt ttagaaggca  13380
ggccgtcagg agcaactccg actccattga cgtttctaaa catctgaatg ccttccttac  13440
cttcaacaaa ctggcaggtt cgggcgacag tgtaaagaga cttgatgaag ttggtgtcgt  13500
cgtgtcggta gtgcttgccc atgaccttct tgatcttctc agtggcgatt cgggcgttgt  13560
agaagggaat tcctttacct gcaggataac ttcgtataat gtatgctata cgaagttatg  13620
atctctctct tgagcttttc cataacaagt tcttctgcct ccaggaagtc catgggtggt  13680
ttgatcatgg ttttggtgta gtggtagtgc agtggtggta ttgtgactgg ggatgtagtt  13740
gagaataagt catacacaag tcagctttct tcgagcctca tataagtata agtagttcaa  13800
cgtattagca ctgtacccag catctccgta tcgagaaaca caacaacatg ccccattgga  13860
cagatcatgc ggatacacag gttgtgcagt atcatacata ctcgatcaga caggtcgtct  13920
gaccatcata caagctgaac aagcgctcca tacttgcacg ctctctatat acacagttaa  13980
```

-continued

```
attacatatc catagtctaa cctctaacag ttaatcttct ggtaagcctc ccagccagcc  14040

ttctggtatc gcttggcctc ctcaatagga tctcggttct ggccgtacag acctcggccg  14100

acaattatga tatccgttcc ggtagacatg acatcctcaa cagttcggta ctgctgtccg  14160

agagcgtctc ccttgtcgtc aagacccacc ccgggggtca gaataagcca gtcctcagag  14220

tcgcccttag gtcggttctg ggcaatgaag ccaaccacaa actcggggtc ggatcgggca  14280

agctcaatgg tctgcttgga gtactcgcca gtggccagag agcccttgca agacagctcg  14340

gccagcatga gcagacctct ggccagcttc tcgttgggag aggggactag gaactccttg  14400

tactgggagt tctcgtagtc agagacgtcc tccttcttct gttcagagac agtttcctcg  14460

gcaccagctc gcaggccagc aatgattccg gttccgggta caccgtgggc gttggtgata  14520

tcggaccact cggcgattcg gtgacaccgg tactggtgct tgacagtgtt gccaatatct  14580

gcgaactttc tgtcctcgaa caggaagaaa ccgtgcttaa gagcaagttc cttgaggggg  14640

agcacagtgc cggcgtaggt gaagtcgtca atgatgtcga tatgggtttt gatcatgcac  14700

acataaggtc cgaccttatc ggcaagctca atgagctcct tggtggtggt aacatccaga  14760

gaagcacaca ggttggtttt cttggctgcc acgagcttga gcactcgagc ggcaaaggcg  14820

gacttgtgga cgttagctcg agcttcgtag gagggcattt tggtggtgaa gaggagactg  14880

aaataaattt agtctgcaga actttttatc ggaaccttat ctggggcagt gaagtatatg  14940

ttatggtaat agttacgagt tagttgaact tatagataga ctggactata cggctatcgg  15000

tccaaattag aaagaacgtc aatggctctc tgggcgtcgc ctttgccgac aaaaatgtga  15060

tcatgatgaa agccagcaat gacgttgcag ctgatattgt tgtcggccaa ccgcgccgaa  15120

aacgcagctg tcagacccac agcctccaac gaagaatgta tcgtcaaagt gatccaagca  15180

cactcatagt tggagtcgta ctccaaaggc ggcaatgacg agtcagacag atactcgtcg  15240

acgcgataac ttcgtataat gtatgctata cgaagttatc gtacgatagt tagtagacaa  15300

caat                                                              15304
```

<210> SEQ ID NO 29
<211> LENGTH: 1272
<212> TYPE: DNA
<213> ORGANISM: Artificial Sequence
<220> FEATURE:
<223> OTHER INFORMATION: mutant EgD8S-23
<220> FEATURE:
<221> NAME/KEY: misc_feature
<222> LOCATION: (2)..(1270)
<223> OTHER INFORMATION: mutant EgD8S-23 delta-8 desaturase CDS

<400> SEQUENCE: 29

```
catggtgaag gcttctcgac aggctctgcc cctcgtcatc gacggaaagg tgtacgacgt    60

ctccgcttgg gtgaacttcc accctggtgg agctgaaatc attgagaact accagggacg   120

agatgctact gacgccttca tggttatgca ctctcaggaa gccttcgaca agctcaagcg   180

aatgcccaag atcaaccagg cttccgagct gcctccccag gctgccgtca acgaagctca   240

ggaggatttc cgaaagctcc gagaagagct gatcgccact ggcatgtttg acgcctctcc   300

cctctggtac tcgtacaaga tcttgaccac cctgggtctt ggcgtgcttg ccttcttcat   360

gctggtccag taccacctgt acttcattgg tgctctcgtg ctcggtatgc actaccagca   420

aatgggatgg ctgtctcatg acatctgcca ccaccagacc ttcaagaacc gaaactggaa   480

taacgtcctg ggtctggtct ttggcaacgg actccagggc ttctccgtga cctggtggaa   540
```

-continued

```
ggacagacac aacgcccatc attctgctac caacgttcag ggtcacgatc ccgacattga    600

taacctgcct ctgctcgcct ggtccgagga cgatgtcact cgagcttctc ccatctcccg    660

aaagctcatt cagttccaac agtactattt cctggtcatc tgtattctcc tgcgattcat    720

ctggtgtttc cagtctgtgc tgaccgttcg atccctcaag gaccgagaca accagttcta    780

ccgatctcag tacaagaaag aggccattgg actcgctctg cactggactc tcaagaccct    840

gttccacctc ttctttatgc cctccatcct gacctcgatg ctggtgttct ttgtttccga    900

gctcgtcggt ggcttcggaa ttgccatcgt ggtcttcatg aaccactacc ctctggagaa    960

gatcggtgat tccgtctggg acggacatgg cttctctgtg ggtcagatcc atgagaccat   1020

gaacattcga cgaggcatca ttactgactg gttctttgga ggcctgaact accagatcga   1080

gcaccatctc tggcccaccc tgcctcgaca caacctcact gccgtttcct accaggtgga   1140

acagctgtgc cagaagcaca acctccccta ccgaaaccct ctgccccatg aaggtctcgt   1200

catcctgctc cgatacctgt cccagttcgc tcgaatggcc gagaagcagc ccggtgccaa   1260

ggctcagtaa gc                                                       1272
```

<210> SEQ ID NO 30
<211> LENGTH: 422
<212> TYPE: PRT
<213> ORGANISM: Artificial Sequence
<220> FEATURE:
<223> OTHER INFORMATION: mutant EgD8S-23, comprising M1, M2, M3, M8,
      M12, M15, M16, M18, M21, M26, M45, M46, M68 and M70 mutation sites

<400> SEQUENCE: 30

```
Met Val Lys Ala Ser Arg Gln Ala Leu Pro Leu Val Ile Asp Gly Lys
1               5                   10                  15

Val Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Gln Ala Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Leu Thr Thr Leu Gly
            100                 105                 110

Leu Gly Val Leu Ala Phe Phe Met Leu Val Gln Tyr His Leu Tyr Phe
        115                 120                 125

Ile Gly Ala Leu Val Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Val Leu Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220
```

-continued

```
Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Met Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ser Gln Phe Ala Arg Met Ala Glu Lys Gln
                405                 410                 415

Pro Gly Ala Lys Ala Gln
            420


<210> SEQ ID NO 31
<211> LENGTH: 777
<212> TYPE: DNA
<213> ORGANISM: Euglena gracilis
<220> FEATURE:
<221> NAME/KEY: misc_feature
<223> OTHER INFORMATION: delta-9 elongase

<400> SEQUENCE: 31

atggaggtgg tgaatgaaat agtctcaatt gggcaggaag ttttacccaa agttgattat      60

gcccaactct ggagtgatgc cagtcactgt gaggtgcttt acttgtccat cgcatttgtc     120

atcttgaagt tcactcttgg ccccccttggt ccaaaaggtc agtctcgtat gaagtttgtt     180

ttcaccaatt acaaccttct catgtccatt tattcgttgg gatcattcct ctcaatggca     240

tatgccatgt acaccatcgg tgttatgtct gacaactgcg agaaggcttt tgacaacaac     300

gtcttcagga tcaccacgca gttgttctat ttgagcaagt tcctggagta tattgactcc     360

ttctatttgc cactgatggg caagcctctg acctggttgc aattcttcca tcatttgggg     420

gcaccgatgg atatgtggct gttctataat taccgaaatg aagctgtttg gatttttgtg     480

ctgttgaatg gtttcatcca ctggatcatg tacggttatt attggaccag attgatcaag     540

ctgaagttcc ccatgccaaa atccctgatt acatcaatgc agatcattca attcaatgtt     600

ggtttctaca ttgtctggaa gtacaggaac attccctgtt atcgccaaga tgggatgagg     660

atgtttggct ggttcttcaa ttacttttat gttggcacag tcttgtgttt gttcttgaat     720

ttctatgtgc aaacgtatat cgtcaggaag cacaagggag ccaaaaagat tcagtga        777


<210> SEQ ID NO 32
<211> LENGTH: 13707
```

-continued

<212> TYPE: DNA
<213> ORGANISM: Artificial Sequence
<220> FEATURE:
<223> OTHER INFORMATION: Plasmid pZKSL-555R

<400> SEQUENCE: 32

```
aaacagtgta cgcagatctg cccatgatgg gggctcccac caccagcaat cagggccctg     60
attacacacc cacctgtaat gtcatgctgt tcatcgtggt taatgctgct gtgtgctgtg    120
tgtgtgtgtt gtttggcgct cattgttgcg ttatgcagcg tacaccacaa tattggaagc    180
ttattagcct ttctattttt tcgtttgcaa ggcttaacaa cattgctgtg gagagggatg    240
gggatatgga ggccgctgga gggagtcgga gaggcgtttt ggagcggctt ggcctggcgc    300
ccagctcgcg aaacgcacct aggacccttt ggcacgccga aatgtgccac ttttcagtct    360
agtaacgcct tacctacgtc attccatgcg tgcatgtttg cgcctttttt cccttgccct    420
tgatcgccac acagtacagt gcactgtaca gtggaggttt tgggggggtc ttagatggga    480
gctaaaagcg gcctagcggt acactagtgg gattgtatgg agtggcatgg agcctaggtg    540
gagcctgaca ggacgcacga ccggctagcc cgtgacagac gatgggtggc tcctgttgtc    600
caccgcgtac aaatgtttgg gccaaagtct tgtcagcctt gcttgcgaac ctaattccca    660
attttgtcac ttcgcacccc cattgatcga gccctaaccc ctgcccatca ggcaatccaa    720
ttaagctcgc attgtctgcc ttgtttagtt tggctcctgc ccgtttcggc gtccacttgc    780
acaaacacaa acaagcatta tatataaggc tcgtctctcc ctcccaacca cactcacttt    840
tttgcccgtc ttcccttgct aacacaaaag tcaagaacac aaacaaccac cccaaccccc    900
ttacacacaa gacatatcta cagcaatggc catggctctc tcccttacta ccgagcagct    960
gctcgagcga cccgacctgg ttgccatcga cggcattctc tacgatctgg aaggtcttgc   1020
caaggtccat cccggaggcg acttgatcct cgcttctggt gcctccgatg cttctcctct   1080
gttctactcc atgcaccctt acgtcaagcc cgagaactcg aagctgcttc aacagttcgt   1140
gcgaggcaag cacgaccgaa cctccaagga cattgtctac acctacgact ctccctttgc   1200
acaggacgtc aagcgaacta tgcgagaggt catgaaaggt cggaactggt atgccacacc   1260
tggattctgg ctgcgaaccg ttggcatcat tgctgtcacc gccttttgcg agtggcactg   1320
ggctactacc ggaatggtgc tgtggggtct cttgactgga ttcatgcaca tgcagatcgg   1380
cctgtccatt cagcacgatg cctctcatgg tgccatcagc aaaaagccct gggtcaacgc   1440
tctctttgcc tacggcatcg acgtcattgg atcgtccaga tggatctggc tgcagtctca   1500
catcatgcga catcacacct acaccaatca gcatggtctc gacctggatg ccgagtccgc   1560
agaaccattc cttgtgttcc acaactaccc tgctgccaac actgctcgaa agtggtttca   1620
ccgattccag gcctggtaca tgtacctcgt gcttggagcc tacggcgttt cgctggtgta   1680
caaccctctc tacatcttcc gaatgcagca caacgacacc attcccgagt ctgtcacagc   1740
catgcgagag aacggctttc tgcgacggta ccgaaccctt gcattcgtta tgcgagcttt   1800
cttcatcttt cgaaccgcct tcttgccctg gtatctcact ggaacctccc tgctcatcac   1860
cattcctctg gtgcccactg ctaccggtgc cttcctcacc ttctttttca tcttgtctca   1920
caacttcgat ggctcggagc gaatccccga caagaactgc aaggtcaaga gctccgagaa   1980
ggacgttgaa gccgatcaga tcgactggta cagagctcag gtggagacct cttccaccta   2040
cggtggaccc attgccatgt tctttactgg cggtctcaac ttccagatcg agcatcacct   2100
ctttcctcga atgtcgtctt ggcactatcc cttcgtgcag caagctgtcc gagagtgttg   2160
```

-continued cgaacgacac ggagttcggt acgtcttcta ccctaccatt gtgggcaaca tcatttccac 2220
cctcaagtac atgcacaaag tcggtgtggt tcactgtgtc aaggacgctc aggattccta 2280
agcggccgca agtgtggatg gggaagtgag tgcccggttc tgtgtgcaca attggcaatc 2340
caagatggat ggattcaaca cagggatata gcgagctacg tggtggtgcg aggatatagc 2400
aacggatatt tatgtttgac acttgagaat gtacgataca agcactgtcc aagtacaata 2460
ctaaacatac tgtacatact catactcgta cccgggcaac ggtttcactt gagtgcagtg 2520
gctagtgctc ttactcgtac agtgtgcaat actgcgtatc atagtctttg atgtatatcg 2580
tattcattca tgttagttgc gtacgctgtg ttgttgtatg tggtgaagct tgacaatgga 2640
tggtgtgtcg tatcaggctg gggaacaatt gtgcttaagt atgctgcagt tgagtaagag 2700
tcatcgctcc accaaaataa agtttgccat tagggttgga gagagagatg gtggctggaa 2760
gaattaaatg acatcaagct gaggattgtg ggtgtgcaat aacacatgtt aggggtgacc 2820
tgtggctcga aatctgataa ttattttgta actttatgat tattcttaga tttttttaata 2880 ttcctctata taacacataa gtagctgtcg tctagttgtt catagcctga ctcctgcaat 2940
agattagtgc agagtgattt tgtgcaattg agagccacgg ttgagtcaag tgactttgtg 3000
tgtgaagtca tcttacgttt caagtctcac aggttactca attggttggt tgtctgccct 3060
ttacagatat ttacagtacc tgagcgtaaa gtcgttcatc cacggaatga ctgttcctgt 3120
cacgcagtca tgatcatgga tgtggctggt caggaaccat tttggatagg agacttaggg 3180
attggactat tattgaaaaa actgagccga atatgatata gttctatttg aatgcagaac 3240
ttctgatggt caattcactt atttcaggca tatcggtcat ggtggcagct gccacgatgt 3300
tatctcgttg gaaacctcgg cgcgccagct gcattaatga atcggccaac gcgcggggag 3360
aggcggtttg cgtattgggc gctcttccgc ttcctcgctc actgactcgc tgcgctcggt 3420
cgttcggctg cggcgagcgg tatcagctca ctcaaaggcg gtaatacggt tatccacaga 3480
atcaggggat aacgcaggaa agaacatgtg agcaaaaggc cagcaaaagg ccaggaaccg 3540
taaaaaggcc gcgttgctgg cgtttttcca taggctccgc ccccctgacg agcatcacaa 3600
aaatcgacgc tcaagtcaga ggtggcgaaa cccgacagga ctataaagat accaggcgtt 3660
tccccctgga agctccctcg tgcgctctcc tgttccgacc ctgccgctta ccggatacct 3720
gtccgccttt ctcccttcgg gaagcgtggc gctttctcat agctcacgct gtaggtatct 3780
cagttcggtg taggtcgttc gctccaagct gggctgtgtg cacgaacccc ccgttcagcc 3840
cgaccgctgc gccttatccg gtaactatcg tcttgagtcc aacccggtaa gacacgactt 3900
atcgccactg gcagcagcca ctggtaacag gattagcaga gcgaggtatg taggcggtgc 3960
tacagagttc ttgaagtggt ggcctaacta cggctacact agaagaacag tatttggtat 4020
ctgcgctctg ctgaagccag ttaccttcgg aaaaagagtt ggtagctctt gatccggcaa 4080
acaaaccacc gctggtagcg gtggtttttt tgtttgcaag cagcagatta cgcgcagaaa 4140
aaaaggatct caagaagatc ctttgatctt ttctacgggg tctgacgctc agtggaacga 4200
aaactcacgt taagggattt tggtcatgag attatcaaaa aggatcttca cctagatcct 4260
tttaaattaa aaatgaagtt ttaaatcaat ctaaagtata tatgagtaaa cttggtctga 4320
cagttaccaa tgcttaatca gtgaggcacc tatctcagcg atctgtctat ttcgttcatc 4380
catagttgcc tgactccccg tcgtgtagat aactacgata cgggagggct taccatctgg 4440
ccccagtgct gcaatgatac cgcgagaccc acgctcaccg gctccagatt tatcagcaat 4500
aaaccagcca gccggaaggg ccgagcgcag aagtggtcct gcaactttat ccgcctccat 4560

-continued

```
ccagtctatt aattgttgcc gggaagctag agtaagtagt tcgccagtta atagtttgcg   4620
caacgttgtt gccattgcta caggcatcgt ggtgtcacgc tcgtcgtttg gtatggcttc   4680
attcagctcc ggttcccaac gatcaaggcg agttacatga tcccccatgt tgtgcaaaaa   4740
agcggttagc tccttcggtc ctccgatcgt tgtcagaagt aagttggccg cagtgttatc   4800
actcatggtt atggcagcac tgcataattc tcttactgtc atgccatccg taagatgctt   4860
ttctgtgact ggtgagtact caaccaagtc attctgagaa tagtgtatgc ggcgaccgag   4920
ttgctcttgc ccggcgtcaa tacgggataa taccgcgcca catagcagaa ctttaaaagt   4980
gctcatcatt ggaaaacgtt cttcggggcg aaaactctca aggatcttac cgctgttgag   5040
atccagttcg atgtaaccca ctcgtgcacc caactgatct tcagcatctt ttactttcac   5100
cagcgtttct gggtgagcaa aaacaggaag gcaaaatgcc gcaaaaaagg gaataagggc   5160
gacacggaaa tgttgaatac tcatactctt cctttttcaa tattattgaa gcatttatca   5220
gggttattgt ctcatgagcg gatacatatt tgaatgtatt tagaaaaata aacaaatagg   5280
ggttccgcgc acatttcccc gaaaagtgcc acctgatgcg gtgtgaaata ccgcacagat   5340
gcgtaaggag aaaataccgc atcaggaaat tgtaagcgtt aatattttgt taaaattcgc   5400
gttaaatttt tgttaaatca gctcattttt taaccaatag gccgaaatcg gcaaaatccc   5460
ttataaatca aaagaataga ccgagatagg gttgagtgtt gttccagttt ggaacaagag   5520
tccactatta aagaacgtgg actccaacgt caaagggcga aaaaccgtct atcagggcga   5580
tggcccacta cgtgaaccat caccctaatc aagttttttg gggtcgaggt gccgtaaagc   5640
actaaatcgg aaccctaaag ggagcccccg atttagagct tgacggggaa agccggcgaa   5700
cgtggcgaga aaggaaggga agaaagcgaa aggagcgggc gctagggcgc tggcaagtgt   5760
agcggtcacg ctgcgcgtaa ccaccacacc cgccgcgctt aatgcgccgc tacagggcgc   5820
gtccattcgc cattcaggct gcgcaactgt tgggaagggc gatcggtgcg ggcctcttcg   5880
ctattacgcc agctggcgaa aggggggatgt gctgcaaggc gattaagttg ggtaacgcca   5940
gggttttccc agtcacgacg ttgtaaaacg acggccagtg aattgtaata cgactcacta   6000
tagggcgaat tgggcccgac gtcgcatgca ttccatagcc acacctttgc ctatggcttc   6060
acaaccgaag gcaattcgag aggtcgcgct tatggaatcg actcgtataa agctgaaggg   6120
aaagggagac gttccgagcg ctcagatgca atagtcgtcc agctaatgtg gattcaaaaa   6180
caaccccaac agtaatcttg aaaatttgaa cggatcaatc tgaacactct tgctccaggt   6240
cattcttcta acgcacatcc ccagagtcta gagggagttg tgttgtgaac atcctaataa   6300
acaatgcaat ggattcggga tatcttctgt ctcgcccccct actcgatgtc gagtaaaccg   6360
atcaccaact aacaatactc ctccgcgttc tgccattgac tctcaaacag acatcgctat   6420
caacggaaca gcatatttta gcttcttagg acaataaata ttgataatgc cggctctccc   6480
tcggtatatt aagcaatcca ttcatacact cattcatcag gttaatttta tatatataat   6540
ttgtctattc aaacaccgta aattactggt accatcatct cctcctttc aaatacacgt   6600
ctatttgcat taatgaaatt actcgccaat tcgcagaacg tgtttgtcga acagagcctt   6660
agctcgggtc cagacaggag cagtgtctcg ctgaggaagc tgcaggagag ttaattaact   6720
cacctgcagg attgagacta tgaatggatt cccgtgcccg tattactcta ctaatttgat   6780
cttggaacgc gaaaatacgt ttctaggact ccaaagaatc tcaactcttg tccttactaa   6840
atatactacc catagttgat ggtttacttg aacagagagg acatgttcac ttgacccaaa   6900
```

-continued

```
gtttctcgca tctcttggat atttgaacaa cggcgtccac tgaccgtcag ttatccagtc   6960
acaaaacccc cacattcata cattcccatg tacgtttaca aagttctcaa ttccatcgtg   7020
caaatcaaaa tcacatctat tcattcatca tatataaacc catcatgtct actaacactc   7080
acaactccat agaaaacatc gactcagaac acacgctcca tgcggccgct taggaatcct   7140
gtgcgtcctt cacgcagtgg acgacaccca ccttatgcat gtacttcagg gtggagatga   7200
tgttgccgac gatggtaggg tagaaaacat atcgcactcc atgtcgttcg caacactccc   7260
ggaccgcctg ctggacgaag ggtagtgcc aagacgacat ccggggaaag aggtggtgct    7320
cgatctggaa attgagaccg ccagtgaaga acatggcgat ggggccaccg tatgtggagg   7380
acgtctccac ctgcgcccga taccagtcaa tttggtcagc ctcaacgtcc ttctcagatc   7440
gcttaacctt gcagttcttg tcggggatcc gttcggagcc atcaaaattg tgggacaaaa   7500
tgaagaagaa cgtcaagaag gcaccagttg cggtgggcac cagaggaatg gtgatcagca   7560
atgaggtccc agtgaggtac cagggcaaga atgcggtccg gaagatgaag aaagctcgca   7620
tcacgaatgc aagtgtgcgg tagcgccgca gaaagccatt ttcccgcatg gccgtgacag   7680
actctgggat ggtgtcattg tgctgcatcc ggaaaatgta gagcgggttg tacaccagcg   7740
ataccccgta tgcccccagc acaaggtaca tgtaccaagc ctggaagcgg tggaaccact   7800
ttcgggcggt gtttgcggcg gggtagttgt ggaacaccag gaacggctct gccgactccg   7860
catccaggtc gaggccgtgc tggttggtgt aggtgtggtg ccgcatgatg tgcgactgca   7920
gccaaatcca ccgggacgat ccgatgacgt caatgccgta ggcgaagagg gcgttgaccc   7980
aaggcttctt gctgatggcc ccgtgggacg catcatgctg gatggataag ccgatctgca   8040
tgtgcatgaa tccagtcaac aggccccaca gcaccatccc cgtggtagcc cagtgccact   8100
cgcaaaaggc cgtcacggcg atgatcccaa cggtgcgcag ccagaagcca ggggttgcgt   8160
accagttcct ccctttcatc acctcgcgca ttgtccgctt aacgtcttgt gcgaagggag   8220
aatcatacgt gtagacaatg tccttcgagg tgcggtcatg cttccctcgg acgaactgtt   8280
gaagcaattt ggagttctcc ggtttgacgt atggatgcat tgaataaaag agaggggagg   8340
catcagaggc accagaagcg agaatcaaat ctcctcctgg atgaactttg gcaagccctt   8400
caaggtcgta gaggatgcca tcaatcgcaa ccaaatcagg gcgttctaac agctgttctg   8460
tggtaagact gagagccatg gagagctggg ttagtttgtg tagagagtgt gtgttgctag   8520
cgactttcgg attgtgtcat tacacaaaac gcgtcgtctc gacactgatc ttgtcgtgga   8580
tactcacggc tcggacatcg tcgccgacga tgacaccgga ctttcgctta aggacgtcag   8640
taacaggcat tgtgtgatgt gtagtttaga tttcgaatct gtggggaaag aaaggaaaaa   8700
agagactggc aaccgattgg gagagccact gtttatatat accctagaca agccccccgc   8760
ttgtaagatg ttggtcaatg taaaccagta ttaaggttgg caagtgcagg agaagcaagg   8820
tgtgggtacc gagcaatgga aatgtgcgga aggcaaaaaa atgaggccac ggcctattgt   8880
cggggctata tccagggggc gattgaagta cactaacatg acatgtgtcc acagaccctc   8940
aatctggcct gatgagccaa atccatacgc gctttcgcag ctctaaaggc tataacaagt   9000
cacaccaccc tgctcgacct cagcgccctc actttttgtt aagacaaact gtacacgctg   9060
ttccagcgtt ttctgcctgc acctggtggg acatttggtg caacctaaag tgctcggaac   9120
ctctgtggtg tccagatcag cgcagcagtt ccgaggtagt tttgaggccc ttagatgatg   9180
caatggtgtc agtcgctgga tcacgagtct taatggcagt attcgttctt atttgtgcca   9240
ttgagccccg ttatcctcgt atcttctacc ccccatccca tccctttgtt ggtgcaaccc   9300
```

-continued

```
tacccattta ttgttgggtg cagcccaacc gacgtggaga gcttggcttg gccatataaa   9360
aaggcccccc cctagtggca atggcagaaa gtcagctgtg agttgttgaa tttgtcatct   9420
aggcggcctg gccgtcttct ccggggcaat tggggctgtt ttttgggaca caaatacgcc   9480
gccaacccgg tctctcctga attccgtcgt cgcctgagtc gacatcattt atttaccagt   9540
tggccacaaa cccttgacga tctcgtatgt cccctccgac atactcccgg ccggctgggg   9600
tacgttcgat agcgctatcg gcatcgacaa ggtttgggtc cctagccgat accgcactac   9660
ctgagtcaca atcttcggag gtttagtctt ccacatagca cgggcaaaag tgcgtatata   9720
tacaagagcg tttgccagcc acagattttc actccacaca ccacatcaca catacaacca   9780
cacacatcca caatggaacc cgaaactaag aagaccaaga ctgactccaa gaagattgtt   9840
cttctcggcg gcgacttctg tggccccgag gtgattgccg aggccgtcaa ggtgctcaag   9900
tctgttgctg aggcctccgg caccgagttt gtgtttgagg accgactcat tggaggagct   9960
gccattgaga aggagggcga gcccatcacc gacgctactc tcgacatctg ccgaaaggct  10020
gactctatta tgctcggtgc tgtcggaggc gctgccaaca ccgtatggac cactcccgac  10080
ggacgaaccg acgtgcgacc cgagcagggt ctcctcaagc tgcgaaagga cctgaacctg  10140
tacgccaacc tgcgaccctg ccagctgctg tcgcccaagc tcgccgatct ctcccccatc  10200
cgaaacgttg agggcaccga cttcatcatt gtccgagagc tcgtcggagg tatctacttt  10260
ggagagcgaa aggaggatga cggatctggc gtcgcttccg acaccgagac ctactccgtt  10320
cctgaggttg agcgaattgc ccgaatggcc gccttcctgg cccttcagca caacccccct  10380
cttcccgtgt ggtctcttga caaggccaac gtgctggcct cctctcgact ttggcgaaag  10440
actgtcactc gagtcctcaa ggacgaactc ccccagctcg agctcaacca ccagctgatc  10500
gactcggccg ccatgatcct catcaagcag ccctccaaga tgaatggtat catcatcacc  10560
accaacatgt ttggcgatat catctccgac gaggcctccg tcatccccgg ttctctgggt  10620
ctgctgccct ccgcctctct ggcttctctg cccgacacca acgaggcgtt cggtctgtac  10680
gagccctgtc acggatctgc ccccgatctc ggcaagcaga aggtcaaccc cattgccacc  10740
attctgtctg ccgccatgat gctcaagttc tctcttaaca tgaagcccgc cggtgacgct  10800
gttgaggctg ccgtcaagga gtccgtcgag gctggtatca ctaccgccga tatcggaggc  10860
tcttcctcca cctccgaggt cggagacttg ttgccaacaa ggtcaaggag ctgctcaaga  10920
aggagtaagt cgtttctacg acgcattgat ggaaggagca aactgacgcg cctgcgggtt  10980
ggtctaccgg cagggtccgc tagtgtataa gactctataa aaagggccct gccctgctaa  11040
tgaaatgatg atttataatt taccggtgta gcaaccttga ctagaagaag cagattgggt  11100
gtgtttgtag tggaggacag tggtacgttt tggaaacagt cttcttgaaa gtgtcttgtc  11160
tacagtatat tcactcataa cctcaatagc caagggtgta gtcggtttat taaaggaagg  11220
gagttgtggc tgatgtggat atcgatagtt ggagcaaggg agaaatgtag agtgtgaaag  11280
actcactatg gtccgggctt atctcgacca atagccaaag tctggagttt ctgagagaaa  11340
aaggcaagat acgtatgtaa caaagcgacg catggtacaa taataccgga ggcatgtatc  11400
atagagagtt agtggttcga tgatggcact ggtgcctggt atgactttat acggctgact  11460
acatatttgt cctcagacat acaattacag tcaagcactt accettggac atctgtaggt  11520
acccccggc caagacgatc tcagcgtgtc gtatgtcgga ttggcgtagc tccctcgctc  11580
gtcaattggc tcccatctac tttcttctgc ttggctacac ccagcatgtc tgctatggct  11640
```

-continued

```
cgttttcgtg ccttatctat cctcccagta ttaccaactc taaatgacat gatgtgattg  11700

ggtctacact ttcatatcag agataaggag tagcacagtt gcataaaaag cccaactcta  11760

atcagcttct tcctttcttg taattagtac aaaggtgatt agcgaaatct ggaagcttag  11820

ttggccctaa aaaaatcaaa aaaagcaaaa aacgaaaaac gaaaaaccac agttttgaga  11880

acagggaggt aacgaaggat cgtatatata tatatatata tatataccca cggatcccga  11940

gaccggcctt tgattcttcc ctacaaccaa ccattctcac caccctaatt cacaaccatg  12000

gctcccgacg ccgacaagct gcgacagcga aaggctcagt ccatccagga cactgccgat  12060

tctcaggcta ccgagctcaa gattggcacc ctgaagggtc tccaaggcac cgagatcgtc  12120

attgatggcg acatctacga catcaaagac ttcgatcacc ctggaggcga atccatcatg  12180

acctttggtg gcaacgacgt tactgccacc tacaagatga ttcatcccta ccactcgaag  12240

catcacctgg agaagatgaa aaaggtcggt cgagtgcccg actacacctc cgagtacaag  12300

ttcgatactc ccttcgaacg agagatcaaa caggaggtct tcaagattgt gcgaagaggt  12360

cgagagtttg gaacacctgg ctacttcttt cgagccttct gctacatcgg tctcttcttt  12420

tacctgcagt atctctgggt taccactcct accactttcg cccttgctat cttctacggt  12480

gtgtctcagg ccttcattgg cctgaacgtc cagcacgacg ccaaccacgg agctgcctcc  12540

aaaaagccct ggatcaacaa tttgctcggc ctgggtgccg actttatcgg aggctccaag  12600

tggctctgga tgaaccagca ctggacccat cacacttaca ccaaccatca cgagaaggat  12660

cccgacgccc tgggtgcaga gcctatgctg ctcttcaacg actatccctt gggtcacccc  12720

aagcgaaccc tcattcatca cttccaagcc ttctactatc tgtttgtcct tgctggctac  12780

tgggtgtctt cggtgttcaa ccctcagatc ctggacctcc agcaccgagg tgcccaggct  12840

gtcggcatga agatggagaa cgactacatt gccaagtctc gaaagtacgc tatcttcctg  12900

cgactcctgt acatctacac caacattgtg gctcccatcc agaaccaagg cttttcgctc  12960

accgtcgttg ctcacattct tactatgggt gtcgcctcca gcctgaccct cgctactctg  13020

ttcgccctct cccacaactt cgagaacgca gatcgggatc ccacctacga ggctcgaaag  13080

ggaggcgagc ctgtctgttg gttcaagtcg caggtggaaa cctcctctac ttacggtggc  13140

ttcatttccg gttgccttac aggcggactc aactttcagg tcgagcatca cctgtttcct  13200

cgaatgtcct ctgcctggta cccctacatc gctcctaccg ttcgagaggt ctgcaaaaag  13260

cacggcgtca agtacgccta ctatccctgg gtgtggcaga acctcatctc gaccgtcaag  13320

tacctgcatc agtccggaac tggctcgaac tggaagaacg gtgccaatcc ctactctggc  13380

aagctgtaag cggccgcatg tacatacaag attatttata gaaatgaatc gcgatcgaac  13440

aaagagtacg agtgtacgag taggggatga tgataaaagt ggaagaagtt ccgcatcttt  13500

ggatttatca acgtgtagga cgatacttcc tgtaaaaatg caatgtcttt accataggtt  13560

ctgctgtaga tgttattaac taccattaac atgtctactt gtacagttgc agaccagttg  13620

gagtatagaa tggtacactt accaaaaagt gttgatggtt gtaactacga tatataaaac  13680

tgttgacggg atctgcgtac actgttt                                      13707
```

```
<210> SEQ ID NO 33
<211> LENGTH: 1350
<212> TYPE: DNA
<213> ORGANISM: Euglena gracilis
<220> FEATURE:
<221> NAME/KEY: misc_feature
<223> OTHER INFORMATION: synthetic delta-5 desaturase (codon-optimized)
      for Yarrowia lipolytica
```

-continued

<400> SEQUENCE: 33

```
atggctctct cccttactac cgagcagctg ctcgagcgac ccgacctggt tgccatcgac      60
ggcattctct acgatctgga aggtcttgcc aaggtccatc ccggaggcga cttgatcctc     120
gcttctggtg cctccgatgc ttctcctctg ttctactcca tgcaccctta cgtcaagccc     180
gagaactcga agctgcttca acagttcgtg cgaggcaagc acgaccgaac ctccaaggac     240
attgtctaca cctacgactc tccctttgca caggacgtca agcgaactat gcgagaggtc     300
atgaaaggtc ggaactggta tgccacacct ggattctggc tgcgaaccgt tggcatcatt     360
gctgtcaccg ccttttgcga gtggcactgg gctactaccg gaatggtgct gtggggtctc     420
ttgactggat tcatgcacat gcagatcggc ctgtccattc agcacgatgc ctctcatggt     480
gccatcagca aaaagccctg ggtcaacgct ctctttgcct acggcatcga cgtcattgga     540
tcgtccagat ggatctggct gcagtctcac atcatgcgac atcacaccta caccaatcag     600
catggtctcg acctggatgc cgagtccgca gaaccattcc ttgtgttcca caactaccct     660
gctgccaaca ctgctcgaaa gtggtttcac cgattccagg cctggtacat gtacctcgtg     720
cttggagcct acggcgtttc gctggtgtac aaccctctct acatcttccg aatgcagcac     780
aacgacacca ttcccgagtc tgtcacagcc atgcgagaga acggctttct gcgacggtac     840
cgaacccttg cattcgttat gcgagctttc ttcatctttc gaaccgcctt cttgccctgg     900
tatctcactg gaacctccct gctcatcacc attcctctgg tgcccactgc taccggtgcc     960
ttcctcacct tctttttcat cttgtctcac aacttcgatg gctcggagcg aatccccgac    1020
aagaactgca aggtcaagag ctccgagaag gacgttgaag ccgatcagat cgactggtac    1080
agagctcagg tggagacctc ttccacctac ggtggaccca ttgccatgtt ctttactggc    1140
ggtctcaact tccagatcga gcatcacctc tttcctcgaa tgtcgtcttg gcactatccc    1200
ttcgtgcagc aagctgtccg agagtgttgc gaacgacacg gagttcggta cgtcttctac    1260
cctaccattg tgggcaacat catttccacc ctcaagtaca tgcacaaagt cggtgtggtt    1320
cactgtgtca aggacgctca ggattcctaa                                     1350
```

<210> SEQ ID NO 34
<211> LENGTH: 449
<212> TYPE: PRT
<213> ORGANISM: Euglena gracilis

<400> SEQUENCE: 34

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
```

-continued

```
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser
```

<210> SEQ ID NO 35
<211> LENGTH: 1392
<212> TYPE: DNA
<213> ORGANISM: Peridinium sp. CCMP626
<220> FEATURE:
<221> NAME/KEY: misc_feature
<223> OTHER INFORMATION: synthetic delta-5 desaturase (codon-optimized)
for Yarrowia lipolytica

<400> SEQUENCE: 35

```
atggctcccg acgccgacaa gctgcgacag cgaaaggctc agtccatcca ggacactgcc      60

gattctcagg ctaccgagct caagattggc accctgaagg gtctccaagg caccgagatc     120
```

-continued

```
gtcattgatg gcgacatcta cgacatcaaa gacttcgatc accctggagg cgaatccatc    180
atgacctttg gtggcaacga cgttactgcc acctacaaga tgattcatcc ctaccactcg    240
aagcatcacc tggagaagat gaaaaaggtc ggtcgagtgc ccgactacac ctccgagtac    300
aagttcgata ctcccttcga acgagagatc aaacaggagg tcttcaagat tgtgcgaaga    360
ggtcgagagt ttggaacacc tggctacttc tttcgagcct tctgctacat cggtctcttc    420
ttttacctgc agtatctctg ggttaccact cctaccactt tcgcccttgc tatcttctac    480
ggtgtgtctc aggccttcat tggcctgaac gtccagcacg acgccaacca cggagctgcc    540
tccaaaaagc cctggatcaa caatttgctc ggcctgggtg ccgactttat cggaggctcc    600
aagtggctct ggatgaacca gcactggacc catcacactt acaccaacca tcacgagaag    660
gatcccgacg ccctgggtgc agagcctatg ctgctcttca acgactatcc cttgggtcac    720
cccaagcgaa ccctcattca tcacttccaa gccttctact atctgtttgt ccttgctggc    780
tactgggtgt cttcggtgtt caaccctcag atcctggacc tccagcaccg aggtgcccag    840
gctgtcggca tgaagatgga gaacgactac attgccaagt ctcgaaagta cgctatcttc    900
ctgcgactcc tgtacatcta caccaacatt gtggctccca tccagaacca aggcttttcg    960
ctcaccgtcg ttgctcacat tcttactatg ggtgtcgcct ccagcctgac cctcgctact   1020
ctgttcgccc tctcccacaa cttcgagaac gcagatcggg atcccaccta cgaggctcga   1080
aagggaggcg agcctgtctg ttggttcaag tcgcaggtgg aaacctcctc tacttacggt   1140
ggcttcattt ccggttgcct tacaggcgga ctcaactttc aggtcgagca tcacctgttt   1200
cctcgaatgt cctctgcctg gtacccctac atcgctccta ccgttcgaga ggtctgcaaa   1260
aagcacggcg tcaagtacgc ctactatccc tgggtgtggc agaacctcat ctcgaccgtc   1320
aagtacctgc atcagtccgg aactggctcg aactggaaga acggtgccaa tccctactct   1380
ggcaagctgt aa                                                       1392
```

<210> SEQ ID NO 36
<211> LENGTH: 463
<212> TYPE: PRT
<213> ORGANISM: Peridinium sp. CCMP626

<400> SEQUENCE: 36

```
Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140
```

-continued

```
Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
    210                 215                 220

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Ser Val Phe Asn Pro Gln Ile Leu
            260                 265                 270

Asp Leu Gln His Arg Gly Ala Gln Ala Val Gly Met Lys Met Glu Asn
        275                 280                 285

Asp Tyr Ile Ala Lys Ser Arg Lys Tyr Ala Ile Phe Leu Arg Leu Leu
    290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp
        355                 360                 365

Phe Lys Ser Gln Val Glu Thr Ser Ser Thr Tyr Gly Gly Phe Ile Ser
    370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
        435                 440                 445

Gly Ser Asn Trp Lys Asn Gly Ala Asn Pro Tyr Ser Gly Lys Leu
    450                 455                 460


<210> SEQ ID NO 37
<211> LENGTH: 1350
<212> TYPE: DNA
<213> ORGANISM: Euglena gracilis
<220> FEATURE:
<221> NAME/KEY: misc_feature
<222> LOCATION: (1)..(1350)
<223> OTHER INFORMATION: delta-5 desaturase

<400> SEQUENCE: 37

atggctctca gtcttaccac agaacagctg ttagaacgcc ctgatttggt tgcgattgat      60

ggcatcctct acgaccttga agggcttgcc aaagttcatc caggaggaga tttgattctc     120

gcttctggtg cctctgatgc ctcccctctc ttttattcaa tgcatccata cgtcaaaccg     180
```

-continued

```
gagaattcca aattgcttca acagttcgtc cgagggaagc atgaccgcac ctcgaaggac    240

attgtctaca cgtatgattc tcccttcgca caagacgtta agcggacaat gcgcgaggtg    300

atgaaaggga ggaactggta cgcaacccct ggcttctggc tgcgcaccgt tgggatcatc    360

gccgtgacgg ccttttgcga gtggcactgg gctaccacgg ggatggtgct gtggggcctg    420

ttgactggat tcatgcacat gcagatcggc ttatccatcc agcatgatgc gtcccacggg    480

gccatcagca agaagccttg ggtcaacgcc ctcttcgcct acggcattga cgtcatcgga    540

tcgtcccggt ggatttggct gcagtcgcac atcatgcggc accacaccta caccaaccag    600

cacggcctcg acctggatgc ggagtcggca gagccgttcc tggtgttcca caactacccc    660

gccgcaaaca ccgcccgaaa gtggttccac cgcttccaag cttggtacat gtaccttgtg    720

ctgggggcat acggggtatc gctggtgtac aacccgctct acattttccg gatgcagcac    780

aatgacacca tcccagagtc tgtcacggcc atgcgggaga atggctttct gcggcgctac    840

cgcacacttg cattcgtgat gcgagctttc ttcatcttcc ggaccgcatt cttgccctgg    900

tacctcactg ggacctcatt gctgatcacc attcctctgg tgcccactgc aactggtgcc    960

ttcttgacgt tcttcttcat tttgtcccac aattttgatg gctccgaacg gatccccgac   1020

aagaactgca aggttaagag ctctgagaag gacgttgagg ctgaccaaat tgactggtat   1080

cgggcgcagg tggagacgtc ctccacatac ggtggcccca tcgccatgtt cttcactggc   1140

ggtctcaatt tccagatcga gcaccacctc tttccccgga tgtcgtcttg gcactacccc   1200

ttcgtccagc aggcggtccg ggagtgttgc gaacgccatg gagtgcgata tgttttctac   1260

cctaccatcg tcggcaacat catctccacc ctgaagtaca tgcataaggt gggtgtcgtc   1320

cactgcgtga aggacgcaca ggattcctga                                    1350
```

```
<210> SEQ ID NO 38
<211> LENGTH: 3806
<212> TYPE: DNA
<213> ORGANISM: Artificial Sequencec
<220> FEATURE:
<223> OTHER INFORMATION: Plasmid pPrD17S

<400> SEQUENCE: 38
```

```
ggccgcatcg gatcccgggc ccgtcgactg cagaggcctg catgcaagct tggcgtaatc     60

atggtcatag ctgtttcctg tgtgaaattg ttatccgctc acaattccac acaacatacg    120

agccggaagc ataaagtgta aagcctgggg tgcctaatga gtgagctaac tcacattaat    180

tgcgttgcgc tcactgcccg ctttccagtc gggaaacctg tcgtgccagc tgcattaatg    240

aatcggccaa cgcgcgggga gaggcggttt gcgtattggg cgctcttccg cttcctcgct    300

cactgactcg ctgcgctcgg tcgttcggct gcggcgagcg gtatcagctc actcaaaggc    360

ggtaatacgg ttatccacag aatcagggga taacgcagga aagaacatgt gagcaaaagg    420

ccagcaaaag gccaggaacc gtaaaaaggc cgcgttgctg gcgtttttcc ataggctccg    480

cccccctgac gagcatcaca aaaatcgacg ctcaagtcag aggtggcgaa acccgacagg    540

actataaaga taccaggcgt ttccccctgg aagctccctc gtgcgctctc ctgttccgac    600

cctgccgctt accggatacc tgtccgcctt tctcccttcg ggaagcgtgg cgctttctca    660

tagctcacgc tgtaggtatc tcagttcggt gtaggtcgtt cgctccaagc tgggctgtgt    720

gcacgaaccc cccgttcagc ccgaccgctg cgccttatcc ggtaactatc gtcttgagtc    780

caacccggta agacacgact tatcgccact ggcagcagcc actggtaaca ggattagcag    840

agcgaggtat gtaggcggtg ctacagagtt cttgaagtgg tggcctaact acggctacac    900
```

-continued

```
tagaagaaca gtatttggta tctgcgctct gctgaagcca gttaccttcg gaaaaagagt    960
tggtagctct tgatccggca aacaaaccac cgctggtagc ggtggttttt ttgtttgcaa   1020
gcagcagatt acgcgcagaa aaaaaggatc tcaagaagat cctttgatct tttctacggg   1080
gtctgacgct cagtggaacg aaaactcacg ttaagggatt ttggtcatga gattatcaaa   1140
aaggatcttc acctagatcc ttttaaatta aaaatgaagt tttaaatcaa tctaaagtat   1200
atatgagtaa acttggtctg acagttacca atgcttaatc agtgaggcac ctatctcagc   1260
gatctgtcta tttcgttcat ccatagttgc ctgactcccc gtcgtgtaga taactacgat   1320
acgggagggc ttaccatctg gccccagtgc tgcaatgata ccgcgagacc cacgctcacc   1380
ggctccagat ttatcagcaa taaaccagcc agccggaagg gccgagcgca gaagtggtcc   1440
tgcaacttta tccgcctcca tccagtctat taattgttgc cgggaagcta gagtaagtag   1500
ttcgccagtt aatagtttgc gcaacgttgt tgccattgct acaggcatcg tggtgtcacg   1560
ctcgtcgttt ggtatggctt cattcagctc cggttcccaa cgatcaaggc gagttacatg   1620
atcccccatg ttgtgcaaaa aagcggttag ctccttcggt cctccgatcg ttgtcagaag   1680
taagttggcc gcagtgttat cactcatggt tatggcagca ctgcataatt ctcttactgt   1740
catgccatcc gtaagatgct tttctgtgac tggtgagtac tcaaccaagt cattctgaga   1800
atagtgtatg cggcgaccga gttgctcttg cccggcgtca atacgggata ataccgcgcc   1860
acatagcaga actttaaaag tgctcatcat tggaaaacgt tcttcggggc gaaaactctc   1920
aaggatctta ccgctgttga gatccagttc gatgtaaccc actcgtgcac ccaactgatc   1980
ttcagcatct tttactttca ccagcgtttc tgggtgagca aaaacaggaa ggcaaaatgc   2040
cgcaaaaaag ggaataaggg cgacacggaa atgttgaata ctcatactct tcctttttca   2100
atattattga agcatttatc agggttattg tctcatgagc ggatacatat ttgaatgtat   2160
ttagaaaaat aaacaaatag gggttccgcg cacatttccc cgaaaagtgc cacctgacgt   2220
ctaagaaacc attattatca tgacattaac ctataaaaat aggcgtatca cgaggccctt   2280
tcgtctcgcg cgtttcggtg atgacggtga aaacctctga cacatgcagc tcccggagac   2340
ggtcacagct tgtctgtaag cggatgccgg gagcagacaa gcccgtcagg gcgcgtcagc   2400
gggtgttggc gggtgtcggg gctggcttaa ctatgcggca tcagagcaga ttgtactgag   2460
agtgcaccat atgcggtgtg aaataccgca cagatgcgta aggagaaaat accgcatcag   2520
gcgccattcg ccattcaggc tgcgcaactg ttgggaaggg cgatcggtgc gggcctcttc   2580
gctattacgc cagctggcga aagggggatg tgctgcaagg cgattaagtt gggtaacgcc   2640
agggttttcc cagtcacgac gttgtaaaac gacggccagt gaattcgagc tcggtacctc   2700
gcgaatgcat ctagatccat ggctaccaag cagccctacc agttccctac tctgaccgag   2760
atcaagcgat ctcttccctc cgagtgcttt gaagcctcgg tccctctgtc cttgtactac   2820
accgtgcgaa tcgtcgctat tgccgttgct ctggccttcg gactcaacta cgctcgagcc   2880
cttcccgtgg tcgagtctct gtgggcactc gacgctgccc tttgttgcgg ttacgttctg   2940
ctccaaggca ttgtcttctg gggattcttt accgtgggtc acgatgctgg acatggtgcc   3000
ttctctcgat accacctgct caactttgtc gttggcacct ttatccactc cctcattctt   3060
actcccttcg agtcgtggaa gctcacacat cgacaccatc acaagaacac cggaaacatc   3120
gaccgagacg aaatcttcta ccctcagcga aaggccgacg atcatcctct gtctcgaaac   3180
ctcgtcctgg ctctcggtgc cgcttggttt gcctaccttg tcgagggctt tcctccccga   3240
```

-continued aaggtcaacc acttcaaccc cttcgaacct ctgtttgtgc gacaggtggc tgccgttgtc 3300
atttccctct ctgctcactt cgccgtcctg gcactgtccg tgtatctgag ctttcagttc 3360
ggtctcaaga caatggctct gtactactat ggacccgtct tcgtgttcgg ctccatgctc 3420
gtcattacta cctttctgca tcacaatgac gaggaaactc cttggtacgg agattccgac 3480
tggacctacg tcaagggcaa cttgtcttcc gtggaccgat cttacggtgc cttcatcgac 3540
aacctctcgc acaacattgg cacacaccag atccaccatc tgtttcccat cattcctcac 3600
tacaagctca accgagccac cgctgccttc caccaggcct ttcccgaact tgtccgaaag 3660
agcgacgagc ccattctcaa ggctttctgg agagttggtc gactttacgc caactacgga 3720
gtcgtggatc ccgacgcaaa gctgtttact ctcaaggagg ccaaagctgc ctccgaggct 3780
gccaccaaga ccaaggctac ttaagc 3806

<210> SEQ ID NO 39
<211> LENGTH: 8165
<212> TYPE: DNA
<213> ORGANISM: Artificial Sequencec
<220> FEATURE:
<223> OTHER INFORMATION: Plasmid pZUF17

<400> SEQUENCE: 39
gtacgagccg gaagcataaa gtgtaaagcc tggggtgcct aatgagtgag ctaactcaca 60
ttaattgcgt tgcgctcact gcccgctttc cagtcgggaa acctgtcgtg ccagctgcat 120
taatgaatcg gccaacgcgc ggggagaggc ggtttgcgta ttgggcgctc ttccgcttcc 180
tcgctcactg actcgctgcg ctcggtcgtt cggctgcggc gagcggtatc agctcactca 240
aaggcggtaa tacggttatc cacagaatca ggggataacg caggaaagaa catgtgagca 300
aaaggccagc aaaaggccag gaaccgtaaa aaggccgcgt tgctggcgtt tttccatagg 360
ctccgccccc ctgacgagca tcacaaaaat cgacgctcaa gtcagaggtg gcgaaacccg 420
acaggactat aaagatacca ggcgtttccc cctggaagct ccctcgtgcg ctctcctgtt 480
ccgaccctgc cgcttaccgg atacctgtcc gcctttctcc cttcgggaag cgtggcgctt 540
tctcatagct cacgctgtag gtatctcagt tcggtgtagg tcgttcgctc caagctgggc 600
tgtgtgcacg aaccccccgt tcagcccgac cgctgcgcct tatccggtaa ctatcgtctt 660
gagtccaacc cggtaagaca cgacttatcg ccactggcag cagccactgg taacaggatt 720
agcagagcga ggtatgtagg cggtgctaca gagttcttga agtggtggcc taactacggc 780
tacactagaa ggacagtatt tggtatctgc gctctgctga agccagttac cttcggaaaa 840
agagttggta gctcttgatc cggcaaacaa accaccgctg gtagcggtgg tttttttgtt 900
tgcaagcagc agattacgcg cagaaaaaaa ggatctcaag aagatccttt gatcttttct 960
acggggtctg acgctcagtg gaacgaaaac tcacgttaag ggattttggt catgagatta 1020
tcaaaaagga tcttcaccta gatcctttta aattaaaaat gaagttttaa atcaatctaa 1080
agtatatatg agtaaacttg gtctgacagt taccaatgct taatcagtga ggcacctatc 1140
tcagcgatct gtctatttcg ttcatccata gttgcctgac tccccgtcgt gtagataact 1200
acgatacggg agggcttacc atctggcccc agtgctgcaa tgataccgcg agacccacgc 1260
tcaccggctc cagatttatc agcaataaac cagccagccg gaagggccga gcgcagaagt 1320
ggtcctgcaa ctttatccgc ctccatccag tctattaatt gttgccggga agctagagta 1380
agtagttcgc cagttaatag tttgcgcaac gttgttgcca ttgctacagg catcgtggtg 1440
tcacgctcgt cgtttggtat ggcttcattc agctccggtt cccaacgatc aaggcgagtt 1500

```
acatgatccc ccatgttgtg caaaaaagcg gttagctcct tcggtcctcc gatcgttgtc   1560

agaagtaagt tggccgcagt gttatcactc atggttatgg cagcactgca taattctctt   1620

actgtcatgc catccgtaag atgcttttct gtgactggtg agtactcaac caagtcattc   1680

tgagaatagt gtatgcggcg accgagttgc tcttgcccgg cgtcaatacg ggataatacc   1740

gcgccacata gcagaacttt aaaagtgctc atcattggaa aacgttcttc ggggcgaaaa   1800

ctctcaagga tcttaccgct gttgagatcc agttcgatgt aacccactcg tgcacccaac   1860

tgatcttcag catcttttac tttcaccagc gtttctgggt gagcaaaaac aggaaggcaa   1920

aatgccgcaa aaaagggaat aagggcgaca cggaaatgtt gaatactcat actcttcctt   1980

tttcaatatt attgaagcat ttatcagggt tattgtctca tgagcggata catatttgaa   2040

tgtatttaga aaaataaaca aataggggtt ccgcgcacat ttccccgaaa agtgccacct   2100

gacgcgccct gtagcggcgc attaagcgcg gcgggtgtgg tggttacgcg cagcgtgacc   2160

gctacacttg ccagcgccct agcgcccgct cctttcgctt tcttcccttc ctttctcgcc   2220

acgttcgccg gctttccccg tcaagctcta aatcgggggc tccctttagg gttccgattt   2280

agtgctttac ggcacctcga ccccaaaaaa cttgattagg gtgatggttc acgtagtggg   2340

ccatcgccct gatagacggt ttttcgccct ttgacgttgg agtccacgtt ctttaatagt   2400

ggactcttgt tccaaactgg aacaacactc aaccctatct cggtctattc ttttgattta   2460

taagggattt tgccgatttc ggcctattgg ttaaaaaatg agctgattta acaaaaattt   2520

aacgcgaatt ttaacaaaat attaacgctt acaatttcca ttcgccattc aggctgcgca   2580

actgttggga agggcgatcg gtgcgggcct cttcgctatt acgccagctg gcgaaagggg   2640

gatgtgctgc aaggcgatta agttgggtaa cgccagggtt ttcccagtca cgacgttgta   2700

aaacgacggc cagtgaattg taatacgact cactataggg cgaattgggt accgggcccc   2760

ccctcgaggt cgatggtgtc gataagcttg atatcgaatt catgtcacac aaaccgatct   2820

tcgcctcaag gaaacctaat tctacatccg agagactgcc gagatccagt ctacactgat   2880

taattttcgg gccaataatt taaaaaaatc gtgttatata atattatatg tattatatat   2940

atacatcatg atgatactga cagtcatgtc ccattgctaa atagacagac tccatctgcc   3000

gcctccaact gatgttctca atatttaagg ggtcatctcg cattgtttaa taataaacag   3060

actccatcta ccgcctccaa atgatgttct caaaatatat tgtatgaact tattttatt    3120

acttagtatt attagacaac ttacttgctt tatgaaaaac acttcctatt taggaaacaa   3180

tttataatgg cagttcgttc atttaacaat ttatgtagaa taaatgttat aaatgcgtat   3240

gggaaatctt aaatatggat agcataaatg atatctgcat tgcctaattc gaaatcaaca   3300

gcaacgaaaa aaatcccttg tacaacataa atagtcatcg agaaatatca actatcaaag   3360

aacagctatt cacacgttac tattgagatt attattggac gagaatcaca cactcaactg   3420

tctttctctc ttctagaaat acaggtacaa gtatgtacta ttctcattgt tcatacttct   3480

agtcatttca tcccacatat tccttggatt tctctccaat gaatgacatt ctatcttgca   3540

aattcaacaa ttataataag atataccaaa gtagcggtat agtggcaatc aaaaagcttc   3600

tctggtgtgc ttctcgtatt tatttttatt ctaatgatcc attaaaggta tatatttatt   3660

tcttgttata taatcctttt gtttattaca tgggctggat acataaaggt attttgattt   3720

aattttttgc ttaaattcaa tcccccctcg ttcagtgtca actgtaatgg taggaaatta   3780

ccatactttt gaagaagcaa aaaaaatgaa agaaaaaaaa aatcgtattt ccaggttaga   3840
```

-continued

```
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc    4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact tttatcgga accttatctg gggcagtgaa    5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
```

-continued gtggtgtgac ttgttatagc ctttagagct gcgaaagcgc gtatggattt ggctcatcag 6300
gccagattga gggtctgtgg acacatgtca tgttagtgta cttcaatcgc cccctggata 6360
tagccccgac aataggccgt ggcctcattt ttttgccttc cgcacatttc cattgctcgg 6420
tacccacacc ttgcttctcc tgcacttgcc aaccttaata ctggtttaca ttgaccaaca 6480
tcttacaagc ggggggcttg tctagggtat atataaacag tggctctccc aatcggttgc 6540
cagtctcttt tttcctttct ttccccacag attcgaaatc taaactacac atcacacaat 6600
gcctgttact gacgtcctta agcgaaagtc cggtgtcatc gtcggcgacg atgtccgagc 6660
cgtgagtatc cacgacaaga tcagtgtcga gacgacgcgt tttgtgtaat gacacaatcc 6720
gaaagtcgct agcaacacac actctctaca caaactaacc cagctctcca tggctgagga 6780
taagaccaag gtcgagttcc ctaccctgac tgagctgaag cactctatcc ctaacgcttg 6840
ctttgagtcc aacctcggac tctcgctcta ctacactgcc cgagcgatct tcaacgcatc 6900
tgcctctgct gctctgctct acgctgcccg atctactccc ttcattgccg ataacgttct 6960
gctccacgct ctggtttgcg ccacctacat ctacgtgcag ggtgtcatct tctggggttt 7020
ctttaccgtc ggtcacgact gtggtcactc tgccttctcc cgataccact ccgtcaactt 7080
catcattggc tgcatcatgc actctgccat tctgactccc ttcgagtcct ggcgagtgac 7140
ccaccgacac catcacaaga acactggcaa cattgataag gacgagatct tctaccctca 7200
tcggtccgtc aaggacctcc aggacgtgcg acaatgggtc tacaccctcg gaggtgcttg 7260
gtttgtctac ctgaaggtcg gatatgctcc tcgaaccatg tcccactttg accccctgga 7320
ccctctcctg cttcgacgag cctccgctgt catcgtgtcc ctcggagtct gggctgcctt 7380
cttcgctgcc tacgcctacc tcacatactc gctcggcttt gccgtcatgg gcctctacta 7440
ctatgctcct ctctttgtct ttgcttcgtt cctcgtcatt actaccttct tgcatcacaa 7500
cgacgaagct actccctggt acggtgactc ggagtggacc tacgtcaagg gcaacctgag 7560
ctccgtcgac cgatcgtacg gagctttcgt ggacaacctg tctcaccaca ttggcaccca 7620
ccaggtccat cacttgttcc ctatcattcc ccactacaag ctcaacgaag ccaccaagca 7680
ctttgctgcc gcttaccctc acctcgtgag acgtaacgac gagcccatca ttactgcctt 7740
cttcaagacc gctcacctct ttgtcaacta cggagctgtg cccgagactg ctcagatttt 7800
caccctcaaa gagtctgccg ctgcagccaa ggccaagagc gactaagcgg ccgcaagtgt 7860
ggatggggaa gtgagtgccc ggttctgtgt gcacaattgg caatccaaga tggatggatt 7920
caacacaggg atatagcgag ctacgtggtg gtgcgaggat atagcaacgg atatttatgt 7980
ttgacacttg agaatgtacg atacaagcac tgtccaagta caatactaaa catactgtac 8040
atactcatac tcgtacccgg gcaacggttt cacttgagtg cagtggctag tgctcttact 8100
cgtacagtgt gcaatactgc gtatcatagt ctttgatgta tatcgtattc attcatgtta 8160
gttgc 8165

<210> SEQ ID NO 40
<211> LENGTH: 8174
<212> TYPE: DNA
<213> ORGANISM: Artificial Sequencec
<220> FEATURE:
<223> OTHER INFORMATION: Plasmid pZUFPrD17S

<400> SEQUENCE: 40
catggctacc aagcagccct accagttccc tactctgacc gagatcaagc gatctcttcc 60

-continued

```
ctccgagtgc tttgaagcct cggtccctct gtccttgtac tacaccgtgc gaatcgtcgc    120
tattgccgtt gctctggcct tcggactcaa ctacgctcga gcccttcccg tggtcgagtc    180
tctgtgggca ctcgacgctg ccctttgttg cggttacgtt ctgctccaag gcattgtctt    240
ctggggattc tttaccgtgg gtcacgatgc tggacatggt gccttctctc gataccacct    300
gctcaacttt gtcgttggca cctttatcca ctccctcatt cttactccct tcgagtcgtg    360
gaagctcaca catcgacacc atcacaagaa caccggaaac atcgaccgag acgaaatctt    420
ctaccctcag cgaaaggccg acgatcatcc tctgtctcga aacctcgtcc tggctctcgg    480
tgccgcttgg tttgcctacc ttgtcgaggg ctttcctccc cgaaaggtca accacttcaa    540
ccccttcgaa cctctgtttg tgcgacaggt ggctgccgtt gtcatttccc tctctgctca    600
cttcgccgtc ctggcactgt ccgtgtatct gagctttcag ttcggtctca agacaatggc    660
tctgtactac tatggacccg tcttcgtgtt cggctccatg ctcgtcatta ctacctttct    720
gcatcacaat gacgaggaaa ctccttggta cggagattcc gactggacct acgtcaaggg    780
caacttgtct tccgtggacc gatcttacgg tgccttcatc gacaacctct cgcacaacat    840
tggcacacac cagatccacc atctgtttcc catcattcct cactacaagc tcaaccgagc    900
caccgctgcc ttccaccagg cctttcccga acttgtccga aagagcgacg agcccattct    960
caaggctttc tggagagttg gtcgacttta cgccaactac ggagtcgtgg atcccgacgc   1020
aaagctgttt actctcaagg aggccaaagc tgcctccgag gctgccacca agaccaaggc   1080
tacttaagcg gccgcaagtg tggatgggga agtgagtgcc cggttctgtg tgcacaattg   1140
gcaatccaag atggatggat tcaacacagg gatatagcga gctacgtggt ggtgcgagga   1200
tatagcaacg gatatttatg tttgacactt gagaatgtac gatacaagca ctgtccaagt   1260
acaatactaa acatactgta catactcata ctcgtacccg ggcaacggtt tcacttgagt   1320
gcagtggcta gtgctcttac tcgtacagtg tgcaatactg cgtatcatag tctttgatgt   1380
atatcgtatt cattcatgtt agttgcgtac gagccggaag cataaagtgt aaagcctggg   1440
gtgcctaatg agtgagctaa ctcacattaa ttgcgttgcg ctcactgccc gctttccagt   1500
cgggaaacct gtcgtgccag ctgcattaat gaatcggcca acgcgcgggg agaggcggtt   1560
tgcgtattgg gcgctcttcc gcttcctcgc tcactgactc gctgcgctcg gtcgttcggc   1620
tgcggcgagc ggtatcagct cactcaaagg cggtaatacg gttatccaca gaatcagggg   1680
ataacgcagg aaagaacatg tgagcaaaag gccagcaaaa ggccaggaac cgtaaaaagg   1740
ccgcgttgct ggcgtttttc cataggctcc gcccccctga cgagcatcac aaaaatcgac   1800
gctcaagtca gaggtggcga aacccgacag gactataaag ataccaggcg tttccccctg   1860
gaagctccct cgtgcgctct cctgttccga ccctgccgct taccggatac ctgtccgcct   1920
ttctcccttc gggaagcgtg gcgctttctc atagctcacg ctgtaggtat ctcagttcgg   1980
tgtaggtcgt tcgctccaag ctgggctgtg tgcacgaacc ccccgttcag cccgaccgct   2040
gcgccttatc cggtaactat cgtcttgagt ccaacccggt aagacacgac ttatcgccac   2100
tggcagcagc cactggtaac aggattagca gagcgaggta tgtaggcggt gctacagagt   2160
tcttgaagtg gtggcctaac tacggctaca ctagaaggac agtatttggt atctgcgctc   2220
tgctgaagcc agttaccttc ggaaaaagag ttggtagctc ttgatccggc aaacaaacca   2280
ccgctggtag cggtggtttt tttgtttgca agcagcagat tacgcgcaga aaaaaaggat   2340
ctcaagaaga tcctttgatc ttttctacgg ggtctgacgc tcagtggaac gaaaactcac   2400
gttaagggat tttggtcatg agattatcaa aaggatctt cacctagatc cttttaaatt    2460
```

-continued

```
aaaaatgaag ttttaaatca atctaaagta tatatgagta aacttggtct gacagttacc   2520
aatgcttaat cagtgaggca cctatctcag cgatctgtct atttcgttca tccatagttg   2580
cctgactccc cgtcgtgtag ataactacga tacgggaggg cttaccatct ggccccagtg   2640
ctgcaatgat accgcgagac ccacgctcac cggctccaga tttatcagca ataaaccagc   2700
cagccggaag ggccgagcgc agaagtggtc ctgcaacttt atccgcctcc atccagtcta   2760
ttaattgttg ccgggaagct agagtaagta gttcgccagt taatagtttg cgcaacgttg   2820
ttgccattgc tacaggcatc gtggtgtcac gctcgtcgtt tggtatggct tcattcagct   2880
ccggttccca acgatcaagg cgagttacat gatcccccat gttgtgcaaa aaagcggtta   2940
gctccttcgg tcctccgatc gttgtcagaa gtaagttggc cgcagtgtta tcactcatgg   3000
ttatggcagc actgcataat tctcttactg tcatgccatc cgtaagatgc ttttctgtga   3060
ctggtgagta ctcaaccaag tcattctgag aatagtgtat gcggcgaccg agttgctctt   3120
gcccggcgtc aatacgggat aataccgcgc cacatagcag aactttaaaa gtgctcatca   3180
ttggaaaacg ttcttcgggg cgaaaactct caaggatctt accgctgttg agatccagtt   3240
cgatgtaacc cactcgtgca cccaactgat cttcagcatc ttttactttc accagcgttt   3300
ctgggtgagc aaaaacagga aggcaaaatg ccgcaaaaaa gggaataagg gcgacacgga   3360
aatgttgaat actcatactc ttcctttttc aatattattg aagcatttat cagggttatt   3420
gtctcatgag cggatacata tttgaatgta tttagaaaaa taaacaaata ggggttccgc   3480
gcacatttcc ccgaaaagtg ccacctgacg cgccctgtag cggcgcatta agcgcggcgg   3540
gtgtggtggt tacgcgcagc gtgaccgcta cacttgccag cgccctagcg cccgctcctt   3600
tcgctttctt cccttccttt ctcgccacgt tcgccggctt tccccgtcaa gctctaaatc   3660
gggggctccc tttagggttc cgatttagtg ctttacggca cctcgacccc aaaaaacttg   3720
attagggtga tggttcacgt agtgggccat cgccctgata gacggttttt cgccctttga   3780
cgttggagtc cacgttcttt aatagtggac tcttgttcca aactggaaca acactcaacc   3840
ctatctcggt ctattctttt gatttataag ggattttgcc gatttcggcc tattggttaa   3900
aaaatgagct gatttaacaa aaatttaacg cgaattttaa caaaatatta acgcttacaa   3960
tttccattcg ccattcaggc tgcgcaactg ttgggaaggg cgatcggtgc gggcctcttc   4020
gctattacgc cagctggcga aagggggatg tgctgcaagg cgattaagtt gggtaacgcc   4080
agggttttcc cagtcacgac gttgtaaaac gacggccagt gaattgtaat acgactcact   4140
atagggcgaa ttgggtaccg ggcccccccct cgaggtcgat ggtgtcgata agcttgatat   4200
cgaattcatg tcacacaaac cgatcttcgc ctcaaggaaa cctaattcta catccgagag   4260
actgccgaga tccagtctac actgattaat tttcgggcca ataatttaaa aaaatcgtgt   4320
tatataatat tatatgtatt atatatatac atcatgatga tactgacagt catgtcccat   4380
tgctaaatag acagactcca tctgccgcct ccaactgatg ttctcaatat ttaaggggtc   4440
atctcgcatt gtttaataat aaacagactc catctaccgc ctccaaatga tgttctcaaa   4500
atatattgta tgaacttatt tttattactt agtattatta gacaacttac ttgctttatg   4560
aaaaacactt cctatttagg aaacaattta taatggcagt tcgttcattt aacaatttat   4620
gtagaataaa tgttataaat gcgtatggga aatcttaaat atggatagca taaatgatat   4680
ctgcattgcc taattcgaaa tcaacagcaa cgaaaaaaat cccttgtaca acataaatag   4740
tcatcgagaa atatcaacta tcaaagaaca gctattcaca cgttactatt gagattatta   4800
```

-continued

```
ttggacgaga atcacacact caactgtctt tctctcttct agaaatacag gtacaagtat   4860
gtactattct cattgttcat acttctagtc atttcatccc acatattcct tggatttctc   4920
tccaatgaat gacattctat cttgcaaatt caacaattat aataagatat accaaagtag   4980
cggtatagtg gcaatcaaaa agcttctctg gtgtgcttct cgtatttatt tttattctaa   5040
tgatccatta aaggtatata tttatttctt gttatataat ccttttgttt attacatggg   5100
ctggatacat aaaggtattt tgatttaatt ttttgcttaa attcaatccc ccctcgttca   5160
gtgtcaactg taatggtagg aaattaccat acttttgaag aagcaaaaaa aatgaaagaa   5220
aaaaaaaatc gtatttccag gttagacgtt ccgcagaatc tagaatgcgg tatgcggtac   5280
attgttcttc gaacgtaaaa gttgcgctcc ctgagatatt gtacattttt gcttttacaa   5340
gtacaagtac atcgtacaac tatgtactac tgttgatgca tccacaacag tttgttttgt   5400
tttttttgt ttttttttt tctaatgatt cattaccgct atgtatacct acttgtactt   5460
gtagtaagcc gggttattgg cgttcaatta atcatagact tatgaatctg cacggtgtgc   5520
gctgcgagtt acttttagct tatgcatgct acttgggtgt aatattggga tctgttcgga   5580
aatcaacgga tgctcaatcg atttcgacag taattaatta agtcatacac aagtcagctt   5640
tcttcgagcc tcatataagt ataagtagtt caacgtatta gcactgtacc cagcatctcc   5700
gtatcgagaa acacaacaac atgccccatt ggacagatca tgcggataca caggttgtgc   5760
agtatcatac atactcgatc agacaggtcg tctgaccatc atacaagctg aacaagcgct   5820
ccatacttgc acgctctcta tatacacagt taaattacat atccatagtc taacctctaa   5880
cagttaatct tctggtaagc ctcccagcca gccttctggt atcgcttggc ctcctcaata   5940
ggatctcggt tctggccgta cagacctcgg ccgacaatta tgatatccgt tccggtagac   6000
atgacatcct caacagttcg gtactgctgt ccgagagcgt ctcccttgtc gtcaagaccc   6060
accccggggg tcagaataag ccagtcctca gagtcgccct taggtcggtt ctgggcaatg   6120
aagccaacca caaactcggg gtcggatcgg gcaagctcaa tggtctgctt ggagtactcg   6180
ccagtggcca gagagccctt gcaagacagc tcggccagca tgagcagacc tctggccagc   6240
ttctcgttgg gagaggggac taggaactcc ttgtactggg agttctcgta gtcagagacg   6300
tcctccttct tctgttcaga gacagtttcc tcggcaccag ctcgcaggcc agcaatgatt   6360
ccggttccgg gtacaccgtg ggcgttggtg atatcggacc actcggcgat tcggtgacac   6420
cggtactggt gcttgacagt gttgccaata tctgcgaact ttctgtcctc gaacaggaag   6480
aaaccgtgct taagagcaag ttccttgagg gggagcacag tgccggcgta ggtgaagtcg   6540
tcaatgatgt cgatatgggt tttgatcatg cacacataag gtccgacctt atcggcaagc   6600
tcaatgagct ccttggtggt ggtaacatcc agagaagcac acaggttggt tttcttggct   6660
gccacgagct tgagcactcg agcggcaaag gcggacttgt ggacgttagc tcgagcttcg   6720
taggagggca ttttggtggt gaagaggaga ctgaaataaa tttagtctgc agaacttttt   6780
atcggaacct tatctggggc agtgaagtat atgttatggt aatagttacg agttagttga   6840
acttatagat agactggact atacggctat cggtccaaat tagaaagaac gtcaatggct   6900
ctctgggcgt cgcctttgcc gacaaaaatg tgatcatgat gaaagccagc aatgacgttg   6960
cagctgatat tgttgtcggc caaccgcgcc gaaaacgcag ctgtcagacc cacagcctcc   7020
aacgaagaat gtatcgtcaa agtgatccaa gcacactcat agttggagtc gtactccaaa   7080
ggcggcaatg acgagtcaga cagatactcg tcgactcagg cgacgacgga attcctgcag   7140
cccatctgca gaattcagga gagaccgggt tggcggcgta tttgtgtccc aaaaaacagc   7200
```

-continued

```
cccaattgcc ccggagaaga cggccaggcc gcctagatga caaattcaac aactcacagc   7260

tgactttctg ccattgccac tagggggggg cctttttata tggccaagcc aagctctcca   7320

cgtcggttgg gctgcaccca acaataaatg ggtagggttg caccaacaaa gggatgggat   7380

gggggtaga agatacgagg ataacggggc tcaatggcac aaataagaac gaatactgcc   7440

attaagactc gtgatccagc gactgacacc attgcatcat ctaagggcct caaaactacc   7500

tcggaactgc tgcgctgatc tggacaccac agaggttccg agcactttag gttgcaccaa   7560

atgtcccacc aggtgcaggc agaaaacgct ggaacagcgt gtacagtttg tcttaacaaa   7620

aagtgagggc gctgaggtcg agcagggtgg tgtgacttgt tatagccttt agagctgcga   7680

aagcgcgtat ggatttggct catcaggcca gattgagggt ctgtggacac atgtcatgtt   7740

agtgtacttc aatcgccccc tggatatagc cccgacaata ggccgtggcc tcattttttt   7800

gccttccgca catttccatt gctcggtacc cacaccttgc ttctcctgca cttgccaacc   7860

ttaatactgg tttacattga ccaacatctt acaagcgggg ggcttgtcta gggtatatat   7920

aaacagtggc tctcccaatc ggttgccagt ctctttttc ctttctttcc ccacagattc   7980

gaaatctaaa ctacacatca cacaatgcct gttactgacg tccttaagcg aaagtccggt   8040

gtcatcgtcg gcgacgatgt ccgagccgtg agtatccacg acaagatcag tgtcgagacg   8100

acgcgttttg tgtaatgaca caatccgaaa gtcgctagca acacacactc tctacacaaa   8160

ctaacccagc tctc                                                      8174
```